US012779057B2

(12) United States Patent
Cui et al.

(10) Patent No.: US 12,779,057 B2
(45) Date of Patent: Nov. 3, 2026

(54) HEPARANASE COMPOUNDS AND METHODS OF USE

(71) Applicant: University of Florida Research Foundation, Incorporated, Gainesville, FL (US)

(72) Inventors: Lina Cui, Gainesville, FL (US); Kelton Schleyer, Gainesville, FL (US); Jun Liu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1302 days.

(21) Appl. No.: 17/605,144

(22) PCT Filed: Apr. 23, 2020

(86) PCT No.: PCT/US2020/029627
§ 371 (c)(1),
(2) Date: Oct. 20, 2021

(87) PCT Pub. No.: WO2020/219753
PCT Pub. Date: Oct. 29, 2020

(65) Prior Publication Data

US 2022/0202964 A1 Jun. 30, 2022

Related U.S. Application Data

(60) Provisional application No. 62/838,235, filed on Apr. 24, 2019.

(51) Int. Cl.

| | |
|---|---|
| ***A61K 31/425*** | (2006.01) |
| ***A61B 5/055*** | (2006.01) |
| ***A61B 6/03*** | (2006.01) |
| ***A61K 49/08*** | (2006.01) |
| ***A61K 49/10*** | (2006.01) |
| ***A61K 51/04*** | (2006.01) |
| ***C07H 17/075*** | (2006.01) |
| ***C12Q 1/40*** | (2006.01) |
| ***G01N 21/64*** | (2006.01) |

(52) U.S. Cl.
CPC .......... *A61K 51/0491* (2013.01); *A61B 5/055* (2013.01); *A61B 6/037* (2013.01); *A61K 49/085* (2013.01); *A61K 49/106* (2013.01); *A61K 49/108* (2013.01); *C07H 17/075* (2013.01); *C12Q 1/40* (2013.01); *C12Y 302/01166* (2013.01); *G01N 21/6428* (2013.01)

(58) Field of Classification Search
None
See application file for complete search history.

(56) References Cited

U.S. PATENT DOCUMENTS

| | | | | |
|---|---|---|---|---|
| 8,901,160 B2 | 12/2014 | Iriyama et al. | | |
| 9,889,226 B2 | 2/2018 | Campisi et al. | | |
| 2007/0185176 A1 | 8/2007 | Van Gelder et al. | | |
| 2015/0196672 A1* | 7/2015 | Cesati .................. | C07D 237/14 424/9.1 | |

FOREIGN PATENT DOCUMENTS

WO WO 2018/107200 A1 6/2018

OTHER PUBLICATIONS

Pearson et al (Synthesis of simple heparanase substrates. Org. Biomol. Chem., 2011, 9, 4614-4625). (Year: 2011).*
Pearson et al., Synthesis of simple heparanase substrates. Org. Biomol. Chem. 2011;9:4614-25. Epub Feb. 25, 2011.
International Search Report and Written Opinion for PCT/US2020/029627 mailed Sep. 24, 2020.
International Preliminary Report on Patentabilty for PCT/US2020/029627 mailed Nov. 4, 2021.
Invitation to Pay Additional Fees for PCT/US2020/029627 mailed Jul. 7, 2020.
PubChem CID 53309756. Aug. 15, 2011.
Mckenzie, Heparanase: a target for drug discovery in cancer and inflammation. Br J Pharmacol. May 2007;151(1):1-14. doi: 10.1038/sj.bjp.0707182. Epub Mar. 5, 2007.
Rivara et al., Heparanase: a rainbow pharmacological target associated to multiple pathologies including rare diseases. Future Med Chem. Apr. 2016;8(6):647-80. doi: 10.4155/fmc-2016-0012. Epub Apr. 8, 2016.
Sasisekharan et al., Roles of heparan-sulphate glycosaminoglycans in cancer. Nat Rev Cancer. Jul. 2002;2(7):521-8. doi: 10.1038/nrc842.
Wu et al., Structural characterization of human heparanase reveals insights into substrate recognition. Nat Struct Mol Biol. Dec. 2015;22(12):1016-22. doi: 10.1038/nsmb.3136. Epub Nov. 16, 2015. Erratum in: Nat Struct Mol Biol. Jan. 2016;23(1):91. doi: 10.1038/nsmb0116-91. Author manuscript, 20 pages total.
Masola et al., Heparanase as a target in cancer therapy. Curr Cancer Drug Targets. Feb. 2014;14(3):286-93. doi: 10.2174/1568009614666140224155124.

* cited by examiner

*Primary Examiner* — Jake M Vu
(74) *Attorney, Agent, or Firm* — Wolf, Greenfield & Sacks, P.C.

(57) ABSTRACT

The invention relates to compounds that interact with heparanase, uses in heparanase screening, uses in in vitro and in vivo imaging (e.g., positron emission tomography (PET) and magnetic resonance imaging (MRI)), methods of synthesis, methods of modulating heparanase activity, and methods of treating disease and disorders associated with heparanase. The compounds of the invention are also useful in treating one or more diseases or disorders associated with the function of heparanase.

19 Claims, 12 Drawing Sheets

1 2 3

HEPARANASE COMPOUNDS AND METHODS OF USE

RELATED APPLICATION

This application is a national stage filing under 35 U.S.C. 371 of International Patent Application Serial No. PCT/US2020/029627, filed Apr. 23, 2020, which claims priority under 35 U.S.C. 119(e) to U.S. Provisional Application, U.S. Ser. No. 62/838,235, filed Apr. 24, 2019. The entire contents of these applications are incorporated herein by reference in their entirety.

STATEMENT OF GOVERNMENT SUPPORT

This invention was made with government support under Grant No. W81XWH-17-1-0529, awarded by the Defense Health Agency, Medical Research and Development Branch; and Grant No. GM124963, awarded by the National Institutes of Health. The government has certain rights in the invention.

BACKGROUND

Heparanase, an endo-β-glucuronidase of the glycoside hydrolase 79 (GH79) family is responsible for the cleavage of heparan sulfate (HS) chain of heparan sulfate proteoglycans (HSPG) [Rivara, S.; Milazzo, F. M.; Giannini, G., Heparanase: a rainbow pharmacological target associated to multiple pathologies including rare diseases. *Future Med Chem* 2016, 8 (6), 647-680; Wu, L.; Viola, C. M.; Brzozowski, A. M.; Davies, G. J., Structural characterization of human heparanase reveals insights into substrate recognition. *Nat Struct Mol Biol* 2015, 22 (12), 1016-22; Li, J. P.; Vlodaysky, I., Heparin, heparan sulfate and heparanase in inflammatory reactions. *Thromb Haemost* 2009, 102 (5), 823-8]. Heparanase is overexpressed in many human tumors such as head and neck, pancreatic carcinoma, hepatocellular carcinoma [Doweck, I.; Kaplan-Cohen, V.; Naroditsky, I.; Sabo, E.; Ilan, N.; Vlodaysky, I., Heparanase localization and expression by head and neck cancer: Correlation with tumor progression and patient survival. *Neoplasia* 2006, 8 (12), 1055-1061; Cohen-Kaplan, V.; Doweck, I.; Naroditsky, I.; Vlodaysky, I.; Ilan, N., Heparanase Augments Epidermal Growth Factor Receptor Phosphorylation: Correlation with Head and Neck Tumor Progression. *Cancer Res* 2008, 68 (24), 10077-10085; Quiros, R. M.; Rao, G.; Plate, J.; Harris, J. E.; Brunn, G. J.; Platt, J. L.; Gattuso, P.; Prinz, R. A.; Xu, X. L., Elevated serum heparanase-1 levels in patients with pancreatic carcinoma are associated with poor survival. *Cancer* 2006, 106 (3), 532-540; Xiao, Y.; Kleeff, J.; Shi, X.; Buchler, M. W.; Friess, H., Heparanase expression in hepatocellular carcinoma and the cirrhotic liver. *Hepatol Res* 2003, 26 (3), 192-198]. Consequently, heparanase modulates the cellular events and exhibits diversified biological functions, such as angiogenesis, metastasis, and inflammation [Sanderson, R. D.; Elkin, M.; Rapraeger, A. C.; Ilan, N.; Vlodaysky, I., Heparanase regulation of cancer, autophagy and inflammation: new mechanisms and targets for therapy. *Febs J* 2017, 284 (1), 42-55; Elkin, M., Heparanase as mediator of angiogenesis: mode of action. *The FASEB Journal* 2001; Goldshmidt, O.; Zcharia, E.; Abramovitch, R.; Metzger, S.; Aingorn, H.; Friedmann, Y.; Schirrmacher, V.; Mitrani, E.; Vlodaysky, I., Cell surface expression and secretion of heparanase markedly promote tumor angiogenesis and metastasis. *Proc Natl Acad Sci USA* 2002, 99 (15), 10031-6; Zcharia, E.; Zilka, R.; Yaar, A.; Yacoby-Zeevi, O.; Zetser, A.; Metzger, S.; Sarid, R.; Naggi, A.; Casu, B.; Ilan, N.; Vlodaysky, I.; Abramovitch, R., Heparanase accelerates wound angiogenesis and wound healing in mouse and rat models. Faseb J 2005, 19 (2), 211-21; Vlodaysky, I.; Goldshmidt, O.; Zcharia, E.; Atzmon, R.; Rangini-Guatta, Z.; Elkin, M.; Peretz, T.; Friedmann, Y., Mammalian heparanase: involvement in cancer metastasis, angiogenesis and normal development. Seminars in cancer biology 2002, 12 (2), 121-9; Sasisekharan, R.; Shriver, Z.; Venkataraman, G.; Narayanasami, U., Roles of heparan-sulphate glycosaminoglycans in cancer. *Nature reviews. Cancer* 2002, 2 (7), 521-8; McKenzie, E. A., Heparanase: a target for drug discovery in cancer and inflammation. *Br J Pharmacol* 2007, 151 (1), 1-14; Masola, V.; Secchi, M. F.; Gambaro, G.; Onisto, M., Heparanase as a Target in Cancer Therapy. *Curr Cancer Drug Tar* 2014, 14 (3), 286-293]. Thus, heparanase has been considered as a drug target for cancer and inflammation.

Herein, a series of structure-defined heparanase probes for heparanase detection and imaging are described.

BRIEF SUMMARY OF THE INVENTION

In some aspects, the invention is directed toward compounds that interact with heparanase, uses in heparanase screening, uses in in vitro and in vivo imaging (e.g., positron emission tomography (PET) and magnetic resonance imaging (MRI)), methods of synthesis, methods of modulating heparanase activity, and methods of treating disease and disorders associated with heparanase. In some aspects, provided herein are compounds for use in treating one or more diseases or disorders associated with the function of heparanase.

In one aspect, the invention is directed to a compound of Formula (I):

(I)

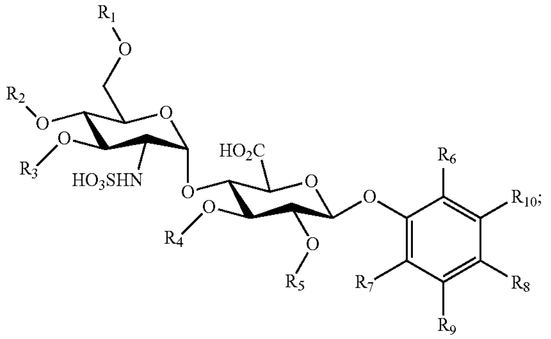

or a salt thereof;

wherein each of $R_1$, $R_2$, $R_3$, $R_4$, and $R_5$ is independently H, $—SO_3H$, or $—PO_3H$;

each of $R_6$ and $R_7$ is independently H, fluoro, chloro, bromo, nitro, cyano, trifluoromethyl, $—CO_2H$, $—OSO_3H$, or $—SO_3H$;

$R_8$ is optionally substituted alkyl, optionally substituted alkenyl, or optionally substituted alkynyl;

each $R_9$ and $R_{10}$ is independently H or alkyl;

or $R_8$ and $R_9$, and the carbon atoms to which they are attached form an optionally substituted heterocyclic or heteroaryl moiety;

or $R_8$ and $R_{10}$, and the carbon atoms to which they are attached form an optionally substituted heterocyclic or heteroaryl moiety;

provided that the compound is not:

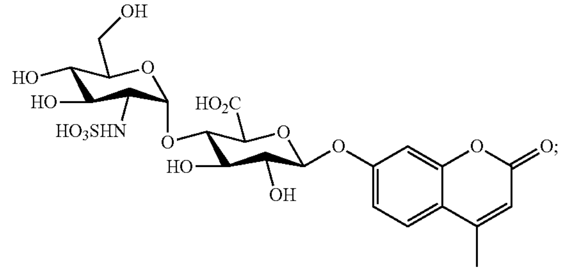

;

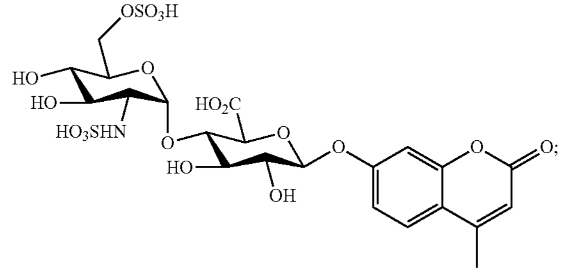

;

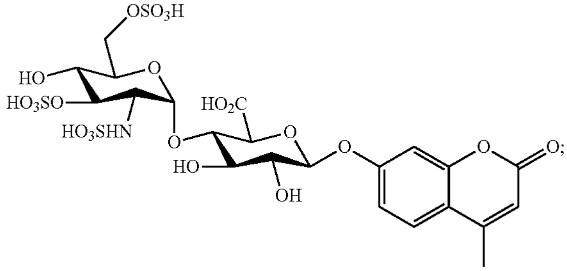

;

or a salt thereof.

In another aspect, the invention is directed to a composition comprising a compound of any of the formulae presented herein, or a salt thereof.

In another aspect, the invention is directed to a pharmaceutical composition comprising a compound of any of the formulae presented herein, or a salt thereof, and a pharmaceutically acceptable carrier.

In another aspect, the invention is directed to a method for screening heparanase inhibitors, the method comprising:

a. incubating heparanase with a heparanase inhibitor;

b. adding a compound of any of the formulae presented herein, or a salt thereof; and c. measuring the fluorescence of the mixture from step b. In another aspect, the method further comprises plotting the fluorescence from step c.

In another aspect, the invention is directed to a method of performing positron emission tomography (PET) in a subject, the method comprising administering to the subject a compound of any of the formulae presented herein, or a salt thereof. In another aspect, the method further comprises subjecting the subject to the positron emission tomography (PET) scan.

In another aspect, the invention is directed to a method of performing magnetic resonance imaging (MRI) in a subject, the method comprising administering to the subject a compound of any of the formulae presented herein, or a salt thereof. In another aspect, the method further comprises subjecting the subject to the magnetic resonance imaging (MRI) scan.

In another aspect, the invention is directed to a kit comprising a compound of any of the formulae presented herein, or a salt thereof, and instructions for screening heparanase inhibitors.

In another aspect, the invention is directed to a kit comprising a compound of any of the formulae presented herein, or a salt thereof, and instructions for performing positron emission tomography (PET) in a subject.

In another aspect, the invention is directed to a kit comprising a compound of any of the formulae presented herein, or a salt thereof, and instructions for performing magnetic resonance imaging (MRI) in a subject.

The details of one or more embodiments of the invention are set forth in the accompanying Figures, the Detailed Description, and the Examples. Other features, objects, and advantages of the invention will be apparent from the description and the claims.

BRIEF DESCRIPTION OF THE DRAWINGS

The present invention is further described below with reference to the following non-limiting examples and with reference to the following figures, in which:

FIG. 4.

FIG. 5.

FIG. 6.

FIG. 8.

DEFINITIONS

Figure 1:
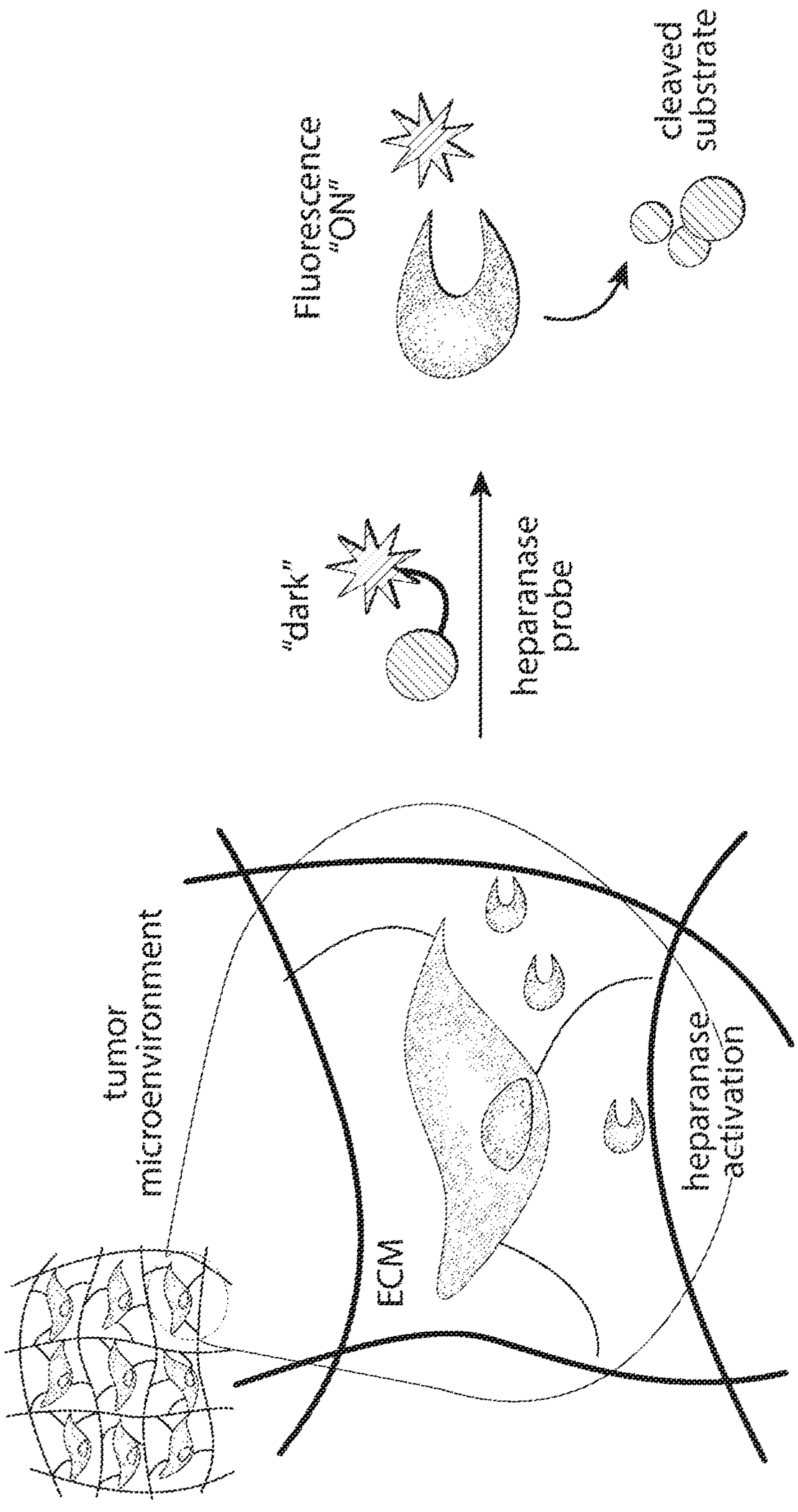
FIG. 1 shows a schematic of the heparanase screening assay.
Figure 2:
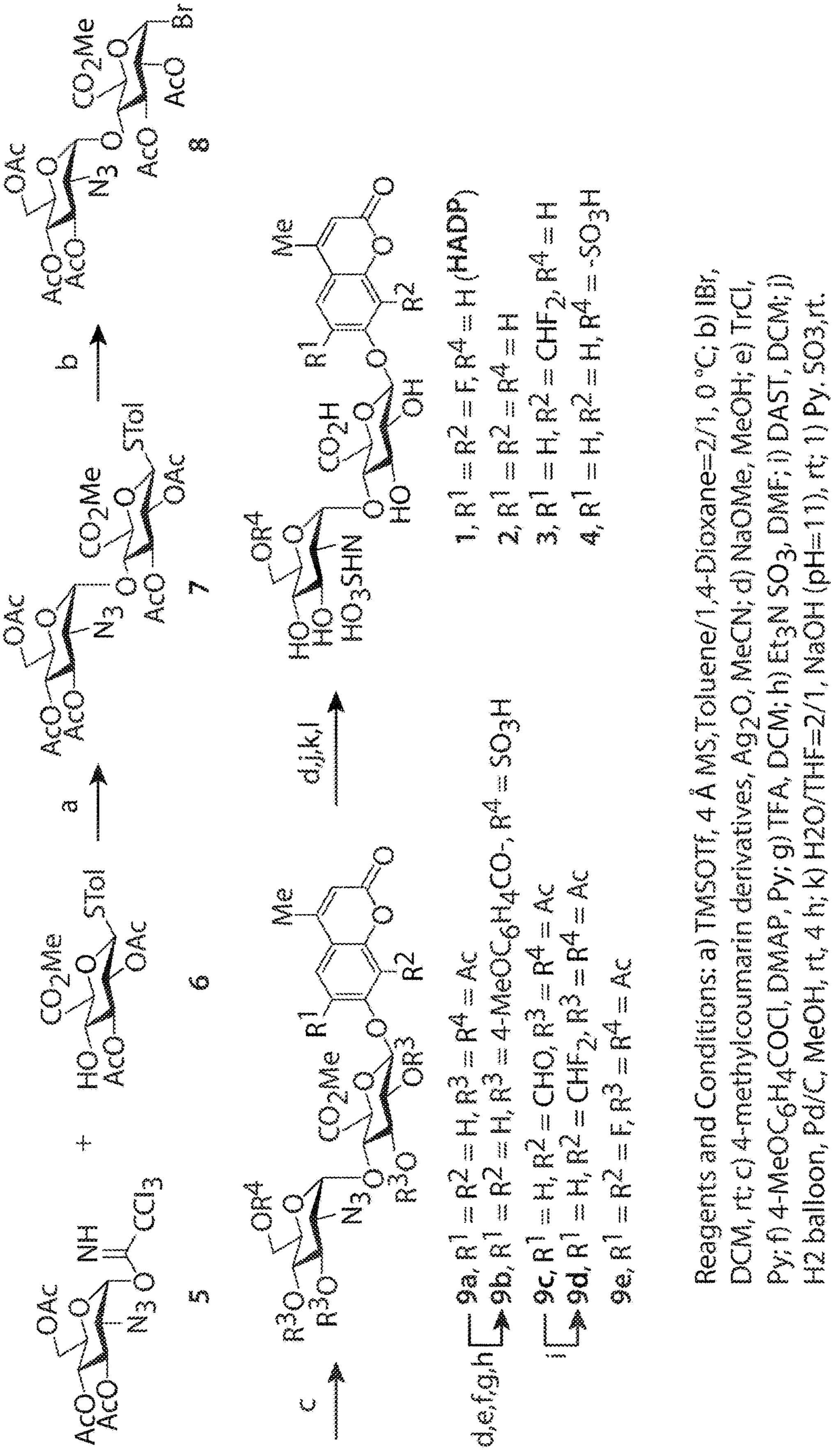
FIG. 2 shows the synthesis of Compounds 1-4.

Before further description of the present invention, and in order that the invention may be more readily understood, certain terms are first defined and collected here for convenience.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

An "imaging agent" refers to a substance administered to enhance contrast in images of the inside of the body obtained using X-rays, γ-rays, sound waves, radio waves (MRI), or radioactive particles in order to diagnose disease The term "protein" refers to series of amino acid residues connected one to the other by peptide bonds between the alpha-amino and carboxy groups of adjacent residues.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "screening effective amount" refers to that amount of the compound being administered sufficient to performing a screen.

The term "imaging effective amount" refers to that amount of the compound being administered sufficient to perform the imaging activities.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents. The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions. Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)$CF_3$), sulfonates (e.g., mesyl, tosyl), acetamides (e.g., —NHC(O)Me), carbamates (e.g., N(Me)C(O)Ot-Bu), phosphonates (e.g., —OP(O)$(OEt)_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

DETAILED DESCRIPTION OF THE INVENTION

In some aspects, the invention is directed toward compounds that interact with heparanase, uses in heparanase screening, uses in in vitro and in vivo imaging (e.g., positron emission tomography (PET) and magnetic resonance imaging (MRI)), methods of synthesis, methods of modulating heparanase activity, and methods of treating disease and disorders associated with heparanase. In some aspects, provided herein are compounds for use in treating one or more diseases or disorders associated with the function of heparanase.

In one aspect, the invention is directed to a compound of Formula (I):

(I)

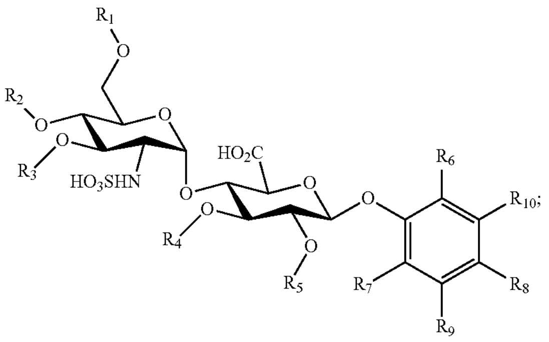

or a salt thereof;

wherein each of $R_1$, $R_2$, $R_3$, $R_4$, and $R_5$ is independently H, —$SO_3H$, or —$PO_3H$;

each of $R_6$ and $R_7$ is independently H, fluoro, chloro, bromo, nitro, cyano, trifluoromethyl, —$CO_2H$, —$OSO_3H$, or —$SO_3H$;

$R_8$ is optionally substituted alkyl, optionally substituted alkenyl, or optionally substituted alkynyl;

each $R_9$ and $R_{10}$ is independently H, fluoro, chloro, bromo, nitro, cyano, trifluoromethyl, —$CO_2H$, —$OSO_3H$, or —$SO_3H$;

or $R_8$ and $R_9$, and the carbon atoms to which they are attached form an optionally substituted heterocyclic or heteroaryl moiety;

or $R_8$ and $R_{10}$, and the carbon atoms to which they are attached form an optionally substituted heterocyclic or heteroaryl moiety;

provided that the compound is not:

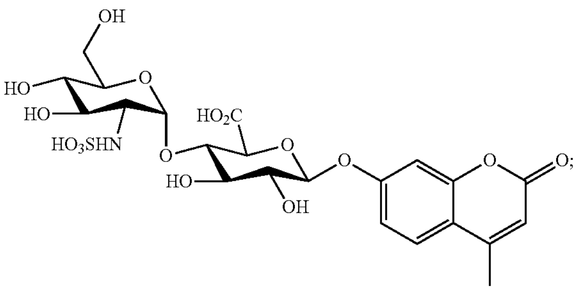

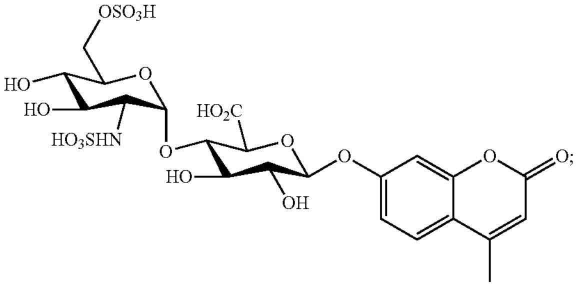

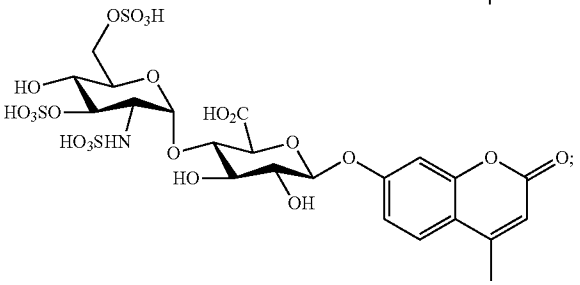

or a salt thereof.

In one aspect, the invention is directed to a compound of Formula (I):

(I)

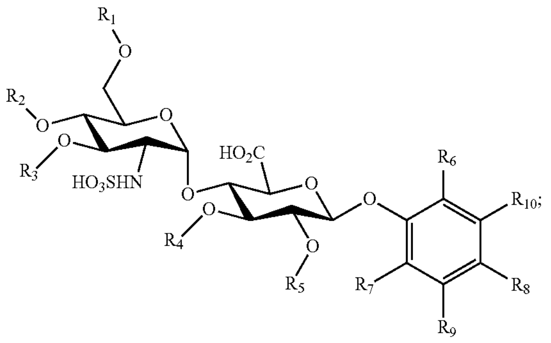

or a salt thereof;

wherein each of $R_1$, $R_2$, $R_3$, $R_4$, and $R_5$ is independently H, —$SO_3H$, or —$PO_3H$;

each of $R_6$ and $R_7$ is independently H, fluoro, chloro, bromo, nitro, cyano, trifluoromethyl, —$CO_2H$, —$OSO_3H$, or —$SO_3H$;

$R_8$ is optionally substituted alkyl, optionally substituted alkenyl, or optionally substituted alkynyl;

each $R_9$ and $R_{10}$ is independently H or alkyl;

or $R_8$ and $R_9$, and the carbon atoms to which they are attached form an optionally substituted heterocyclic or heteroaryl moiety;

or $R_8$ and $R_{10}$, and the carbon atoms to which they are attached form an optionally substituted heterocyclic or heteroaryl moiety;

provided that the compound is not:

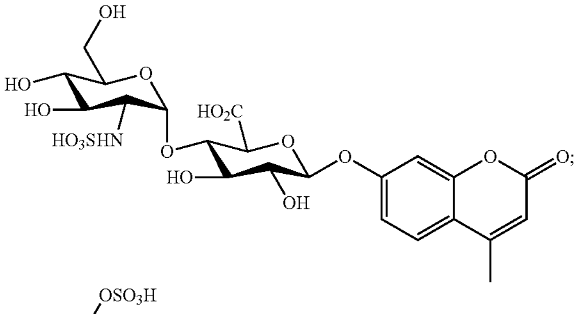

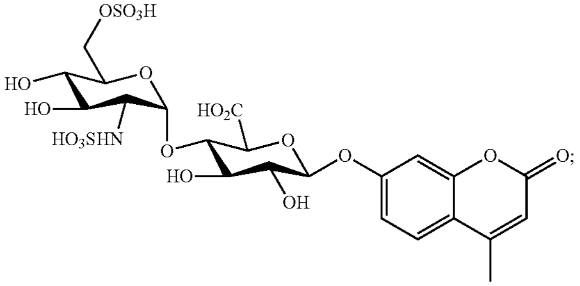

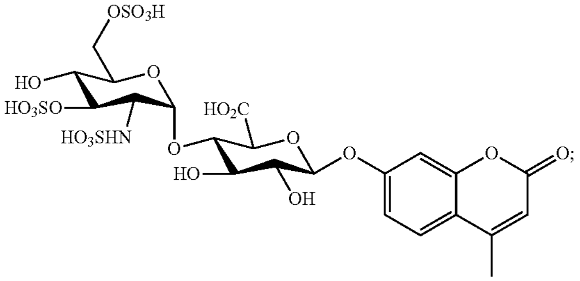

or a salt thereof.

In another aspect, the compound of Formula (I), or a salt thereof, is according to Formula (II):

(II)

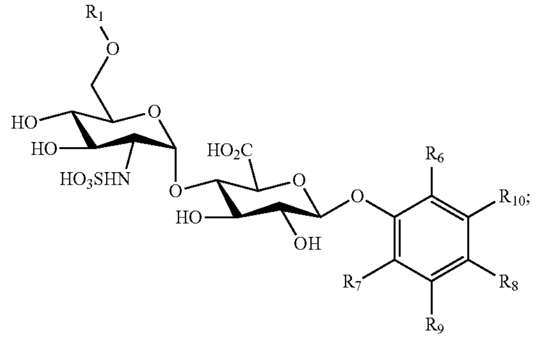

or a salt thereof.

In any of the embodiments presented herein, $R_1$ is H or —$SO_3H$.

In any of the embodiments presented herein, $R_6$, $R_7$, $R_9$, and $R_{10}$ are each independently H, fluoro, chloro, bromo, nitro, —$OSO_3H$, or —$SO_3H$. In any of the embodiments presented herein, $R_6$, $R_7$, $R_9$, and $R_{10}$ are each independently H, fluoro, nitro, —$OSO_3H$, or —$SO_3H$. In any of the embodiments presented herein, $R_6$, $R_7$, $R_9$, and $R_{10}$ are each independently H, fluoro, chloro, or bromo (e.g., H or fluoro). In any of the embodiments presented herein, $R_6$, $R_7$, $R_9$, and $R_{10}$ are each independently H or fluoro. In any of the embodiments presented herein, $R_6$, $R_7$, $R_9$, and $R_{10}$ are each independently H or —$SO_3H$.

In any of the embodiments presented herein, $R_6$ and $R_7$ are each independently H, fluoro, chloro, or bromo (e.g., H or fluoro).

In any of the embodiments presented herein, $R_6$ is fluoro. In any of the embodiments presented herein, $R_7$ is fluoro. In any of the embodiments presented herein, $R_6$ and $R_7$ are fluoro.

In any of the embodiments presented herein,

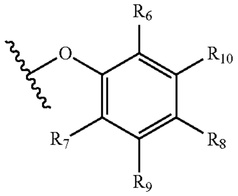 is 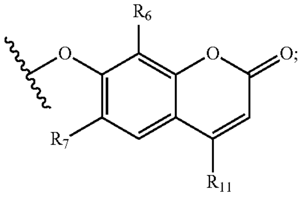

wherein $R_{11}$ is H or alkyl (e.g., methyl).

In any of the embodiments presented herein,

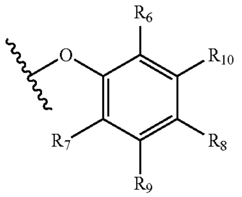

is

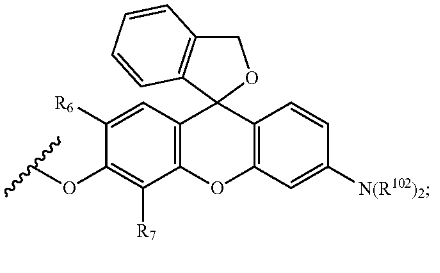

wherein each $R^{102}$ is independently optionally substituted alkyl, optionally substituted alkenyl, or optionally substituted alkynyl.

In any of the embodiments presented herein,

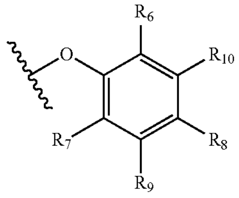

is

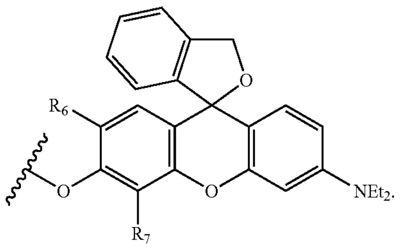

In any of the embodiments presented herein,

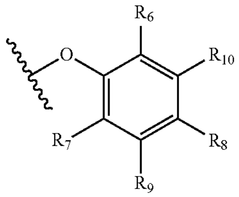

is

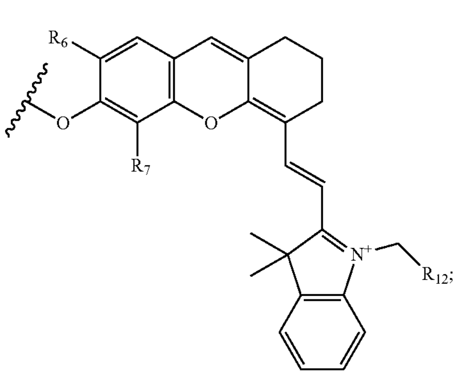

wherein $R_{12}$ is H, alkyl, or alkyl substituted with —$SO_3H$ (e.g., H, ethyl, or —$CH_2CH_2SO_3H$).

In any of the embodiments presented herein,

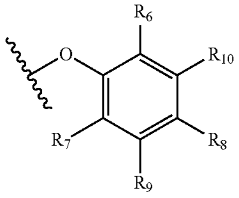

is

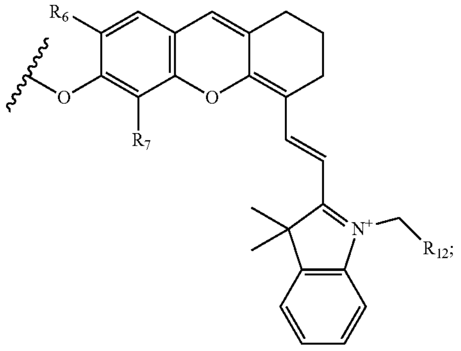

wherein $R_{12}$ is optionally substituted alkyl, optionally substituted alkenyl, optionally substituted alkynyl, optionally substituted aryl, optionally substituted heteroaryl, H, or alkyl substituted with —$SO_3H$ (e.g., H, ethyl, or —$CH_2CH_2SO_3H$).

In any of the embodiments presented herein,

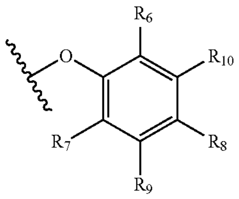

is

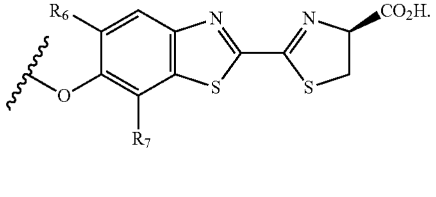

In any of the embodiments presented herein, $R_8$ is

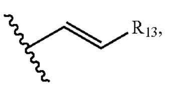

wherein $R_{13}$ is optionally substituted heterocyclyl. In another aspect, $R_{13}$ is

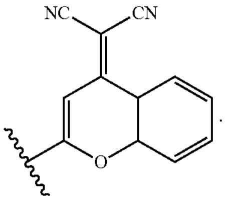 [SMILES: *C1=CC(=C(C#N)C#N)C2C=CC=CC2O1]

In another aspect, $R_{13}$ is

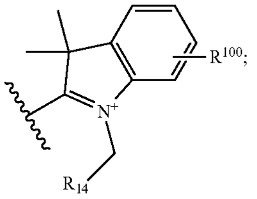

wherein $R_{14}$ is H, alkyl, or alkyl substituted with $SO_3H$ (e.g., H, ethyl, or $—CH_2CH_2SO_3H$); and $R^{100}$ is optionally substituted alkyl, optionally substituted alkenyl, optionally substituted alkynyl, optionally substituted aryl, or optionally substituted heteroaryl. In another aspect, $R_{13}$ is

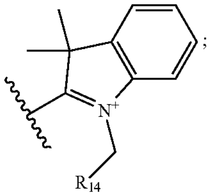

wherein $R_{14}$ is H, alkyl, or alkyl substituted with $SO_3H$ (e.g., H, ethyl, or $—CH_2CH_2SO_3H$).

In any of the embodiments presented herein, $R_8$ is

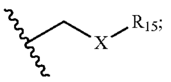

X is O or NH; and $R_{15}$ is optionally substituted aryl or heteroaryl. In another aspect, $R_{15}$ is optionally substituted aryl, optionally substituted heteroaryl, $—(C{=}O)OR_{103}$, $—(C{=}O)N(R_{102})_2$, $—(C{=}S)OR^{103}$, or $—(C{=}S)N(R_{102})_2$, wherein each $R^{102}$ is independently hydrogen or optionally substituted alkyl, and $R^{103}$ is hydrogen or optionally substituted alkyl. In another aspect, $R_{15}$ is

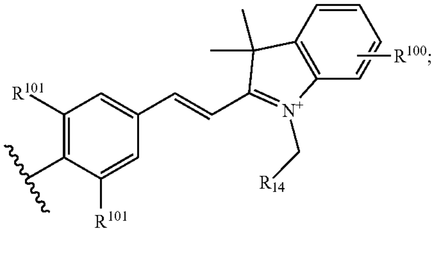

wherein $R_{14}$ is optionally substituted alkyl, optionally substituted alkenyl, optionally substituted alkynyl, optionally substituted aryl, H, or alkyl substituted with $SO_3H$ (e.g., H, ethyl, or $—CH_2CH_2SO_3H$); $R^{100}$ is optionally substituted alkyl, optionally substituted alkenyl, optionally substituted alkynyl, optionally substituted aryl, or optionally substituted heteroaryl; and each $R^{101}$ is independently hydrogen or haloalkyl (e.g., $CHF_2$, $CH_2F$).

In another aspect, $R_{15}$ is

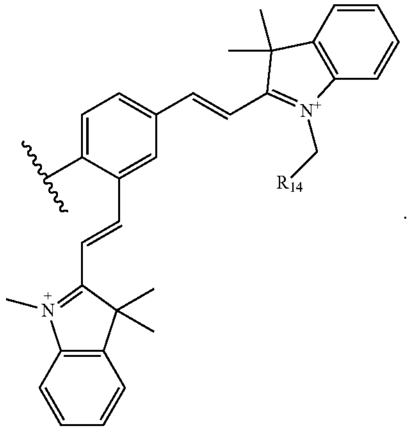

In another aspect, $R_{15}$ is

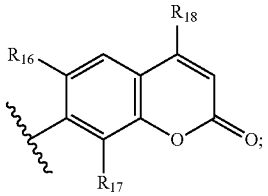

wherein each of $R_{16}$ and $R_{17}$ is independently H or haloalkyl (e.g., H, $—CHF_2$, or $—CH_2F$); and $R_{18}$ is H or alkyl (e.g., methyl). In another aspect, each of $R_{16}$ and $R_{17}$ is independently H, $—CHF_2$, or $—CH_2F$; and $R_{18}$ is methyl. In another aspect, $R_{15}$ is

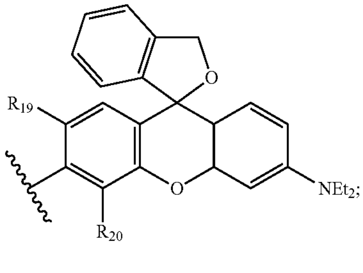

wherein each of $R_{19}$ and $R_{20}$ is independently H or haloalkyl (e.g., H, $—CHF_2$, or $—CH_2F$). In another aspect, $R_{15}$ is

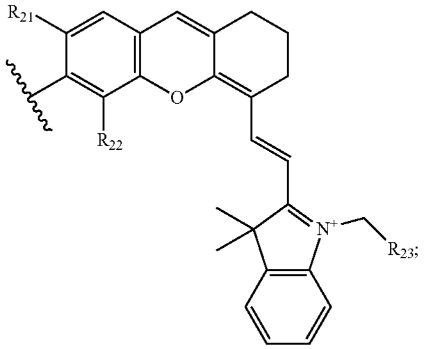

wherein each of $R_{21}$ and $R_{22}$ is independently H or haloalkyl (e.g., H, —$CHF_2$, or —$CH_2F$); and $R_{23}$ is H, alkyl, or alkyl substituted with $SO_3H$ (e.g., H, ethyl, or —$CH_2CH_2SO_3H$). In another aspect, each of $R_{21}$ and $R_{22}$ is independently H, —$CHF_2$, or —$CH_2F$; and $R_{23}$ is H, ethyl, or —$CH_2CH_2SO_3H$. In another aspect, $R_{15}$ is

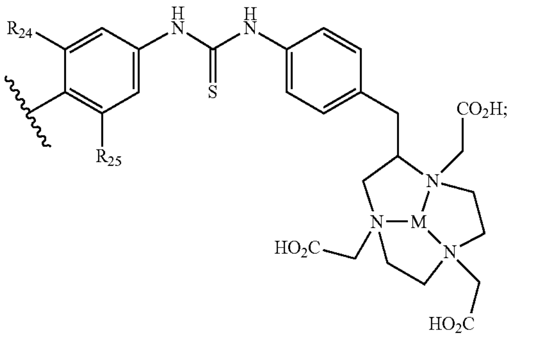

wherein each of $R_{24}$ and $R_{25}$ is independently H or haloalkyl (e.g., H, —$CHF_2$, or —$CH_2F$); and M is $Cu_{64}$ or $AlF_{18}$. In another aspect, $R_{15}$ is

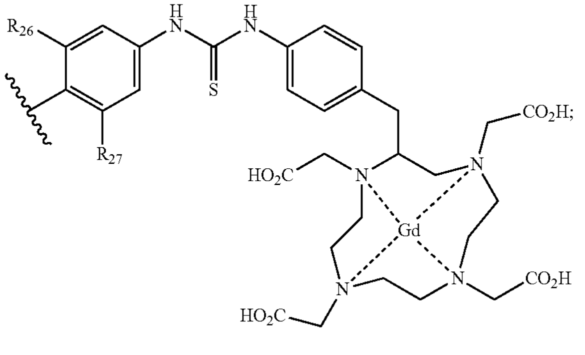

wherein each of $R_{26}$ and $R_{27}$ is independently H or haloalkyl (e.g., H, —$CHF_2$, or —$CH_2F$). In another aspect, $R_{15}$ is

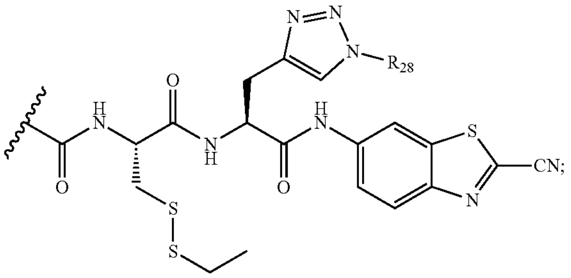

wherein $R_{28}$ is H, alkyl, or an imaging agent. In another aspect, $R_{15}$ is

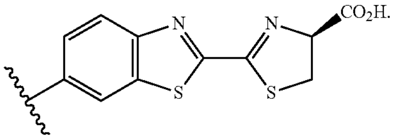 [SMILES: *c1ccc2nc(C3=N[C@@H](C(=O)O)CS3)sc2c1]

In another aspect, $R_{15}$ is

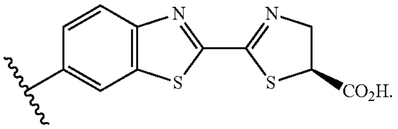 [SMILES: *c1ccc2nc(C3=NC[C@@H](C(=O)O)S3)sc2c1]

In another aspect, $R_{15}$ is

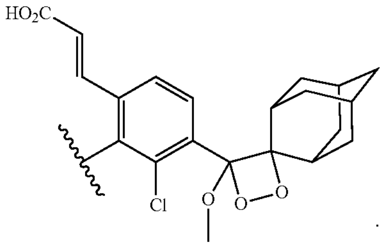 [SMILES: *c1c(/C=C/C(=O)O)ccc(C2(OC)OOC23C2CC4CC(C2)CC3C4)c1Cl]

In any of the embodiments presented herein, $R_8$ is

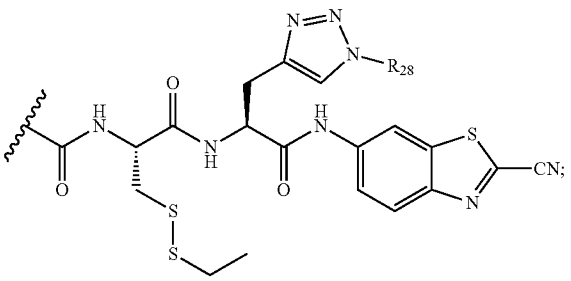

wherein $R_{28}$ is H, alkyl, or an imaging agent.

In another aspect, the imaging agent is:
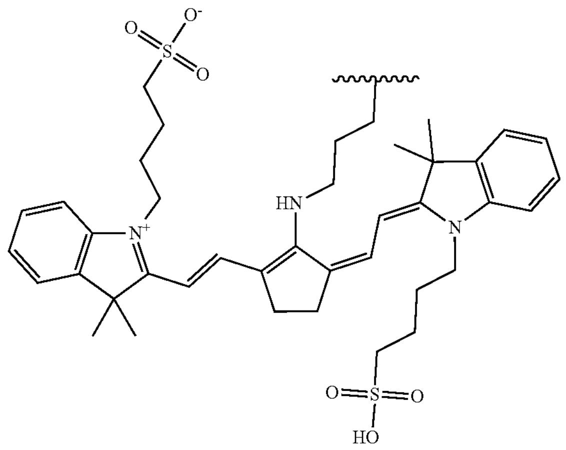
;
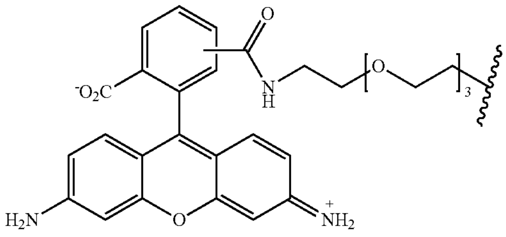
;
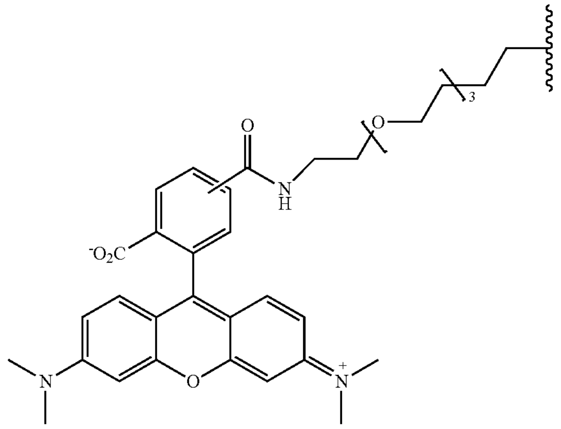
;
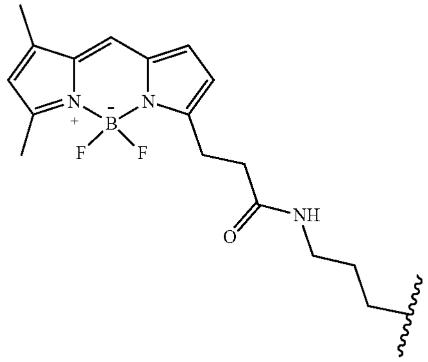
;
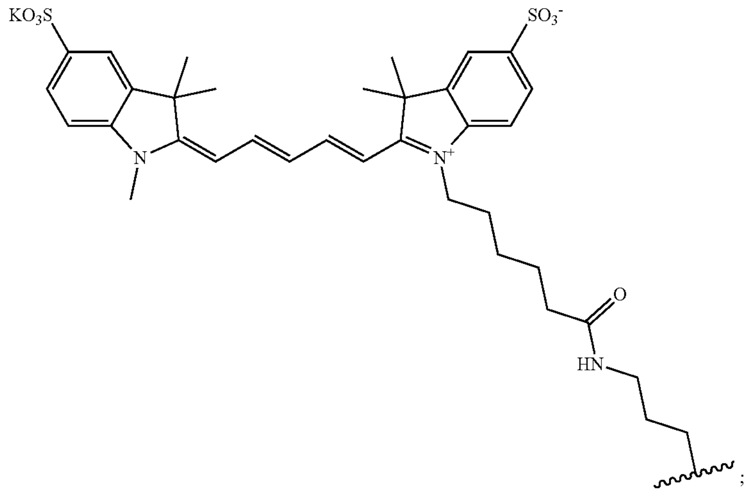
;

-continued
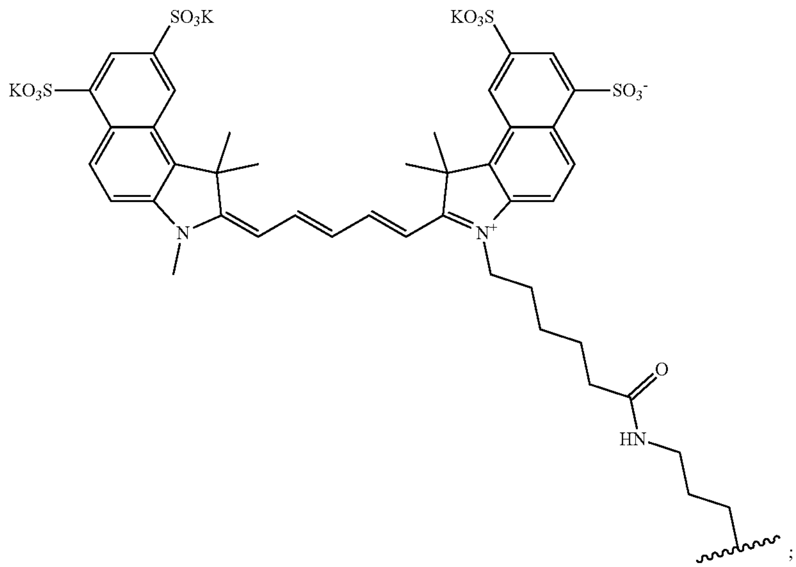
;
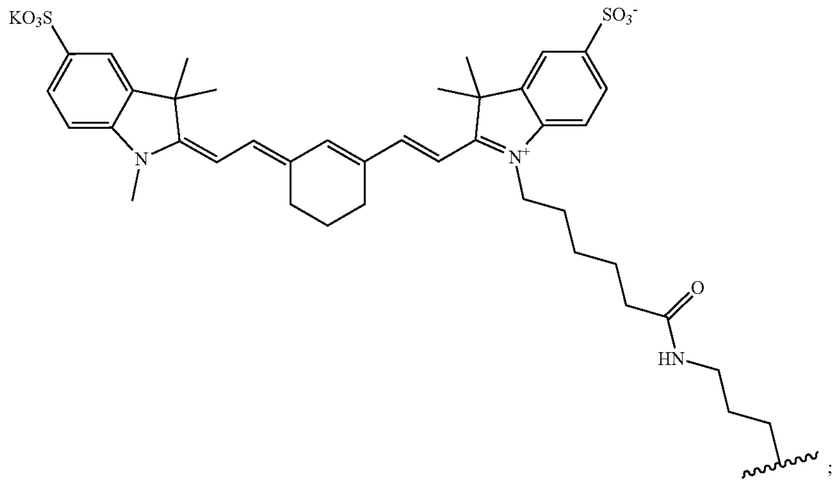
;
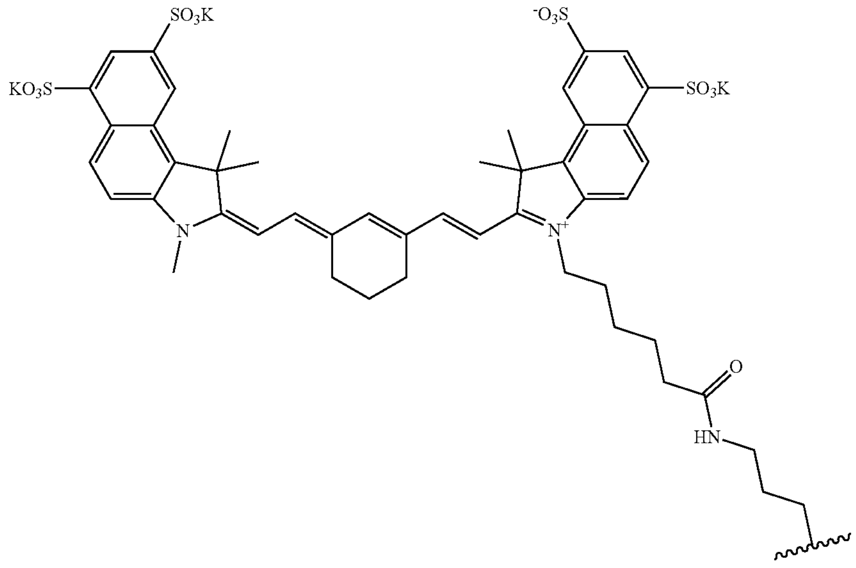
;

-continued
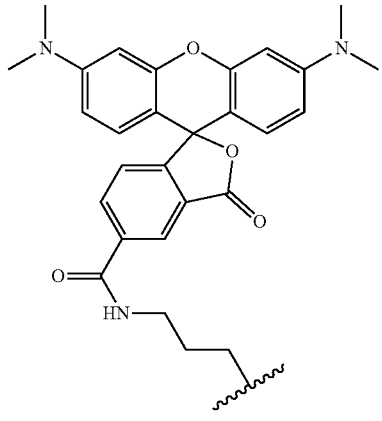
;
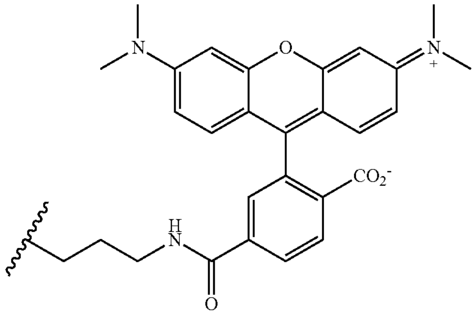
;
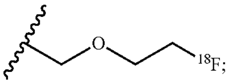
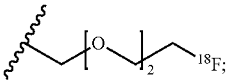
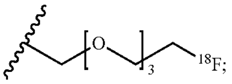
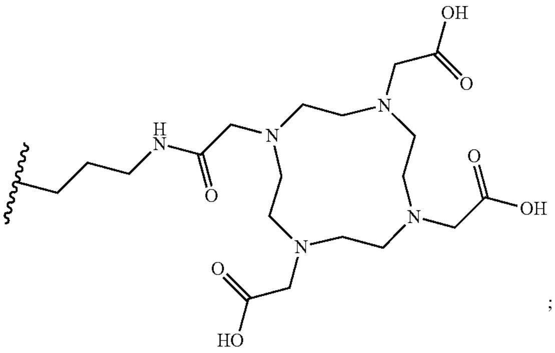
; or
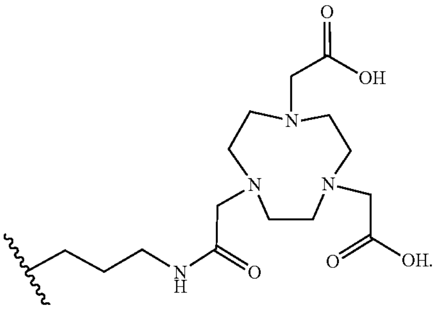
In another aspect, the compound of any of the formulae presented herein is
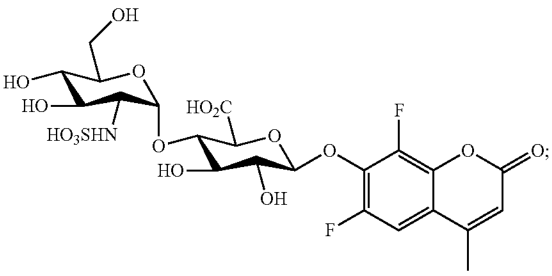
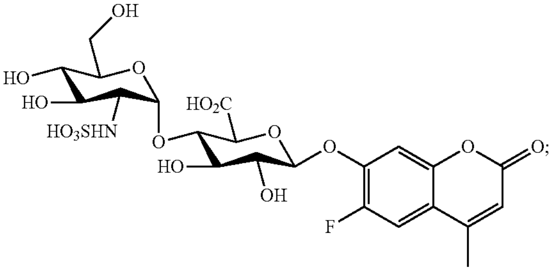
-continued
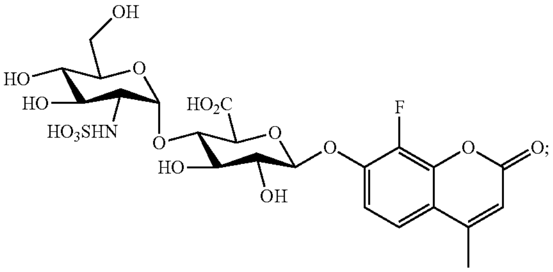
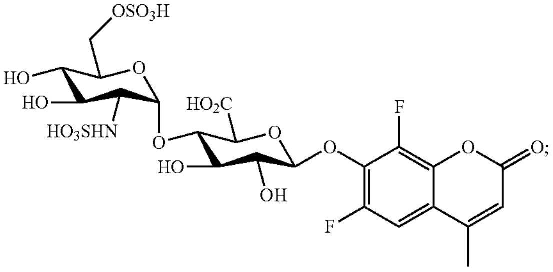

-continued

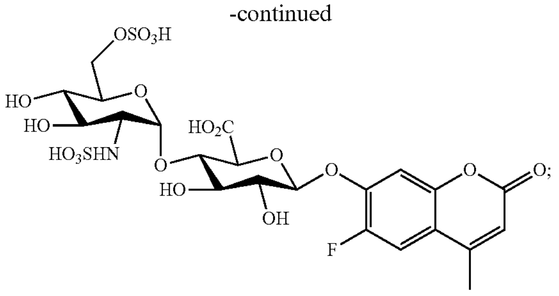

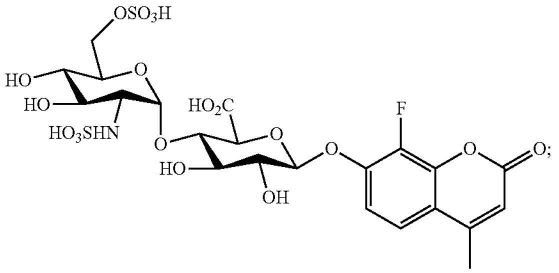

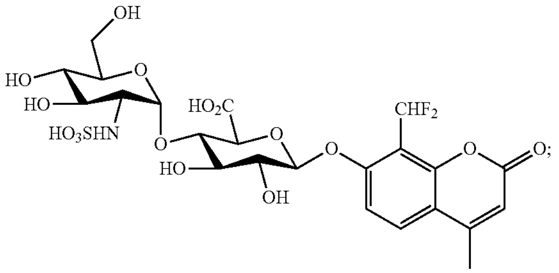

or a salt thereof.

In another aspect, the invention is directed to a composition comprising a compound of any of the formulae presented herein, or a salt thereof.

In another aspect, the invention is directed to a pharmaceutical composition comprising a compound of any of the formulae presented herein, or a salt thereof, and a pharmaceutically acceptable carrier.

In another aspect, the invention is directed to a method for screening heparanase inhibitors, the method comprising:

a. incubating heparanase with a heparanase inhibitor;

b. adding a compound of any of the formulae presented herein, or a salt thereof; and c. measuring the fluorescence of the mixture from step b. In another aspect, the method further comprises plotting the fluorescence from step c.

In another aspect, the invention is directed to a method of performing positron emission tomography (PET) in a subject, the method comprising administering to the subject a compound of any of the formulae presented herein, or a salt thereof. In another aspect, the method further comprises subjecting the subject to the positron emission tomography (PET) scan. In another aspect, the compound comprises $R_{15}$ =

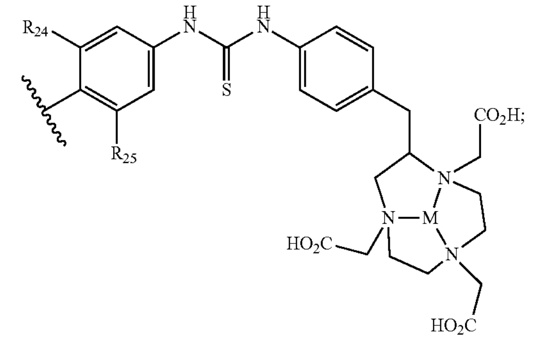

wherein each of $R_{24}$ and $R_{25}$ is independently H or haloalkyl (e.g., H, $—CHF_2$, or $—CH_2F$); and M is $Cu_{64}$ or $AlF_{18}$.

In another aspect, the invention is directed to a method of performing magnetic resonance imaging (MRI) in a subject, the method comprising administering to the subject a compound of any of the formulae presented herein, or a salt thereof. In another aspect, the method further comprises subjecting the subject to the magnetic resonance imaging (MRI) scan. In another aspect, the compound comprises $R_{15}$ =

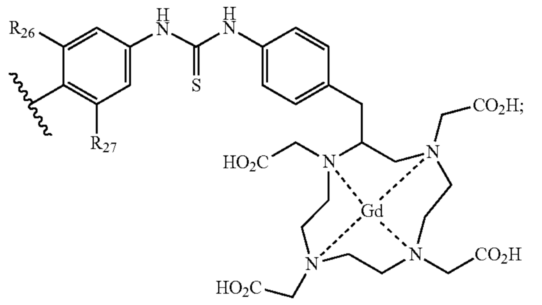

wherein each of $R_{26}$ and $R_{27}$ is independently H or haloalkyl (e.g., H, $—CHF_2$, or $—CH_2F$).

In another aspect, the invention is directed to a kit comprising a compound of any of the formulae presented herein, or a salt thereof, and instructions for screening heparanase inhibitors.

In another aspect, the invention is directed to a kit comprising a compound of any of the formulae presented herein, or a salt thereof, and instructions for performing positron emission tomography (PET) in a subject.

In another aspect, the invention is directed to a kit comprising a compound of any of the formulae presented herein, or a salt thereof, and instructions for performing magnetic resonance imaging (MRI) in a subject.

The details of one or more embodiments of the invention are set forth in the accompanying Figures, the Detailed Description, and the Examples. Other features, objects, and advantages of the invention will be apparent from the description and the claims.

Compounds delineated herein include salts, hydrates, solvates, and prodrugs thereof. In certain embodiments, compounds delineated herein include hydrate and solvates thereof. Compounds described herein may be derivatized to produce a salt form or prodrug form that may be more useful in one or more of the procedures and/or methods (e.g., methods of treatment) described herein. All compounds delineated in schemes herein are contemplated and included, whether intermediate or final compounds in a process.

Compounds of the invention can be made or modified by means known in the art of organic synthesis. Methods for optimizing reaction conditions, if necessary minimizing competing by-products, are known in the art. Additional reaction schemes, optimization, scale-up, and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In certain embodiments, the compounds are formulated for oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for intravenous administration.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

A composition or pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein.

Kits and Methods of Use

In another aspect, the invention is directed to a composition comprising a compound of any of the formulae presented herein, or a salt thereof.

In another aspect, the invention is directed to a method for screening heparanase inhibitors, the method comprising:

a. incubating heparanase with a heparanase inhibitor;
b. adding a compound of any of the formulae presented herein, or a salt thereof; and
c. measuring the fluorescence of the mixture from step b. In another aspect, the method further comprises plotting the fluorescence from step c.

In another aspect, the invention is directed to a method of performing positron emission tomography (PET) in a subject, the method comprising administering to the subject a compound of any of the formulae presented herein, or a salt thereof. In another aspect, the method further comprises subjecting the subject to the positron emission tomography (PET) scan. In another aspect, the compound comprises $R_{15}$ =

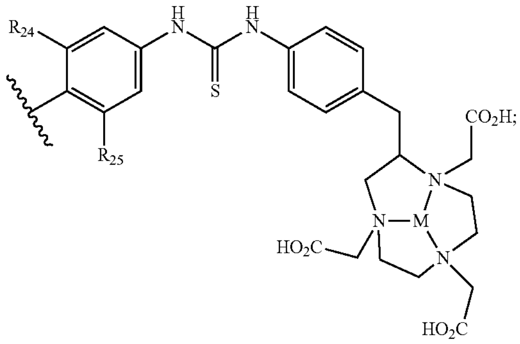

wherein each of $R_{24}$ and $R_{25}$ is independently H or haloalkyl (e.g., H, —$CHF_2$, or —$CH_2F$); and M is $Cu_{64}$ or $AlF_{18}$.

In another aspect, the invention is directed to a method of performing magnetic resonance imaging (MRI) in a subject, the method comprising administering to the subject a compound of any of the formulae presented herein, or a salt thereof. In another aspect, the method further comprises subjecting the subject to the magnetic resonance imaging (MRI) scan. In another aspect, the compound comprises $R_{15}$ =

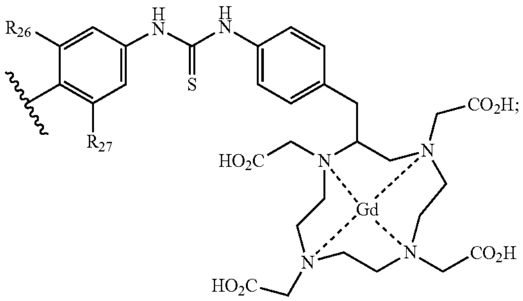

wherein each of $R_{26}$ and $R_{27}$ is independently H or haloalkyl (e.g., H, —$CHF_2$, or —$CH_2F$).

In another aspect, the invention is directed to a kit comprising a compound of any of the formulae presented herein, or a salt thereof, and instructions for screening heparanase inhibitors.

In another aspect, the invention is directed to a kit comprising a compound of any of the formulae presented herein, or a salt thereof, and instructions for performing positron emission tomography (PET) in a subject.

In another aspect, the invention is directed to a kit comprising a compound of any of the formulae presented herein, or a salt thereof, and instructions for performing magnetic resonance imaging (MRI) in a subject.

The details of one or more embodiments of the invention are set forth in the accompanying Figures, the Detailed Description, and the Examples. Other features, objects, and advantages of the invention will be apparent from the description and the claims.

EXAMPLES

The invention is further illustrated by the following examples which are intended to illustrate but not limit the scope of the invention.

The compounds of the invention can be evaluated for their heparanase activity in vitro and in vivo through a variety of assays known in the field. The following examples provide exemplary protocols for evaluating the heparanase activity of the compounds of the invention.

General Methods

Deuterated solvents were purchased from Sigma-Aldrich and Merck Millipore. $^1H$ and $^{13}C$ NMR spectra were recorded on a Bruker instrument (500 and 126 respectively) and internally referenced to the residual solvent signals ($^1H$: δ 7.26; $^{13}C$: δ 77.16 for $CDCl_3$, $^1H$: δ 3.31; $^{13}C$: δ 49.0 for $CD_3OD$ respectively). NMR chemical shifts (δ) and the coupling constants (J) for $^1H$ and $^{13}C$ NMR are reported in parts per million (ppm) and in Hertz, respectively. The following conventions are used for multiplicities: s, singlet; d, doublet; t, triplet; m, multiplet; and dd, doublet of doublet. High resolution mass was recorded on Waters LCT Premier Mass Spectrometer. Absorption spectra were recorded on Shimadzu UV-2700 UV-VIS Spectrophotometer. Fluorescence spectra were recorded on Fluorolog TAU-3 Spectrofluorometer with a xenon lamp (Jobin Yvon-Spex, Instruments S. A., Inc.).

UV-Vis and Fluorescence Methods

To a solution of 20 μL, of 50 μM compound 1 (HADP) and 160 μL 40 mM NaOAc (pH=5.0) was added 20 μL, 0.1 μg/μL heparanase to obtain 5 μM 1 (HADP) with 2 μg heparanase solution. After incubation at 37° C. for 2 h, the reaction solution was transferred to quartz cuvettes to measure absorbance or fluorescence. Absorbance spectrum scan range from 250 nm to 500 nm (1 nm increment). fluorescence spectrum setting: λex=365 nm, Slit Width 2.5 nm. Emission was record from 400 nm to 600 nm, Slit Width 5 nm. Absorption spectra were recorded on Shimadzu UV-2700 UV-VIS Spectrophotometer. Fluorescence spectra were recorded on Fluorolog TAU-3 Spectrofluorometer with a xenon lamp (Jobin Yvon-Spex, Instruments S. A., Inc.)

Time-Dependence of Fluorescence Methods

Fluorescence micro cells was charged with 20 μL, of 50 μM compound 1 (HADP) and 160 μL 40 mM NaOAc (pH=5.0). Then 20 μL, 0.05 μg/μL heparanase was added to the above solution. Fluorescence spectra were recorded from 0 min to 3 h. fluorescence spectrum setting: λex=365 nm, Slit Width 2.5 nm. Emission was record from 400 nm to 600 nm, Slit Width 5 nm.

Fluorescence Response Methods

To a solution of 20 μL, of 50 μM each compound and 160 μL, 40 mM NaOAc (pH=5.0) was added 20 μL, 0.05 μg/μL heparanase to obtain 5 μM each compound with 1 μg heparanase solution in 96-well microplate. Each compound was performed in triplicate. Then the microplate was sealed with sealing film and incubated at 37° C. Fluorescence intensity was recorded on Spectramax M5 Multimode plate reader (Molecular Devices, USA) at each timepoint. λex/em=365 nm/455 nm.

Measurement of Fluorescence Response to Biological Species

5 μM compound 1 (HADP) was incubated with various biological species at the indicated amount/concentration in 96-well microplate. Cysteine (5 mM), Glutathione (5 mM), $H_2O_2$ (100 μM), Esterase, Chondroitinase ABC, Hyaluronidase, Lysozyme, β-Glucuronidase, β-Glucosidase (5 μg each) and heparanase (2 μg). For Chondroitinase ABC and Hyaluronidase, 50 μg was also tested. Each sample was performed in triplicates. Then the microplate was sealed with sealing film and incubated at 37° C. for 4 hours.

Fluorescence intensity was recorded on Spectramax M5 Multimode plate reader (Molecular Devices, USA). λex/em=365 nm/455 nm.

HPLC Analysis Methods of Compounds 1-4 With Heparanase

Heparanase (1 μg, 20 μL) was added to the compounds 1-4 solution (180 μL, 5 μM) in 40 mM NaOAc buffer (pH 5.0) and the mixture was incubated for 4 hours at 37° C. The resulting mixtures were injected into HPLC for analysis. HPLC analysis was performed under the following conditions—mobile phase A: water with 0.1% TFA; B: acetonitrile with 0.1% TFA; 0-20 min: gradient elution, 25-95% B. The trace was monitored by DAD detector at 315 nm.

Method to Measure Inhibition of Heparanase with Suramin

To 37.5 μL 40 mM NaOAc (pH 5.0) in 384-well microplate was added 2.5 μL 0.01 μg/μL, heparanase. Then 5 μL suramin of various concentrations (0.01, 0.03, 0.1, 0.3, 1.0, 3.0, 10, 30, 100, 300, 1000, 3000, 10000 μM) was added. The plates were sealed and incubated at 37° C. for 1 h. Then 5 μL compound 1 (HADP) (50 μM) was added to the microplates. Then the microplates were sealed and incubated at 37° C. from 4 hours. Each compound was performed in triplicates. Fluorescence intensity was recorded on Spectramax M5 Multimode Platereader (Setting: λex=365 nm, λem=455 nm). The relative fluorescent intensity was plotted as a function of logarithm of inhibitor concentrations.

Z'-Factor Determination 48 wells were used as positive controls (5 μM HADP with 0.025 μg hepranase, 50 μL total volume) and other 48 wells were used as positive controls (5 μM HADP only, 50 μL total volume). Then the microplates were sealed and incubated at 37° C. from 4 hours. Fluorescence intensity was recorded on Spectramax M5 Multimode plate reader (Molecular Devices, USA). Then Z'-factor was calculated using $$Z'=1-(3\sigma_p+3\sigma_n)/(|\mu_p-\mu_n|)$$

where $\sigma_p$ and $\sigma_n$ are the standard deviations of the positive and negative controls, respectively and $\mu_p$ and $\mu_n$ are the means of the positive and negative controls, respectively.

Heparanase Screening Methods

A library of 1280 compounds (10 mM, dissolved in DMSO) in 96-well format was purchased from Tocris. Transfer 2 μL of the master library into the daughter library containing 198 μL of water to obtain a daughter library (100 μM for each compound). To 35 μL 40 mM NaOAc (pH 5.0) in 384-well microplates were added 5 μL 0.005 μg/μL, heparanase. Then the daughter library solution (5 μL) was added. The plates were sealed and incubated at 37° C. for 1 h. Then 5 μL compound 1 (HADP) (50 μM) was added to the microplates. Then the microplates were sealed and incubated at 37° C. from 4 hours. Each compound was performed in triplicates. Fluorescence intensity was recorded on Spectramax M5 Multimode Platereader (Setting: λex=365 nm, λem=455 nm).

$IC_{50}$ Measurement

To 40 μL 40 mM NaOAc (pH 5.0) in 384-well microplate was added 5 μL 0.005 μg/μL heparanase. Then 5 μL suramin of various concentrations (0.01, 0.03, 0.1, 0.3, 1.0, 3.0, 10, 30, 100, 300, 1000, 3000, 10000 μM) was added. The plates were sealed and incubated at 37° C. for 1 h. Then 5 μL compound 1 (HADP) (50 μM) was added to the microplates. Then the microplates were sealed and incubated at 37° C. from 4 hours. Each compound was performed in triplicates. Fluorescence intensity was recorded on Spectramax M5 Multimode Platereader (Setting: λex=365 nm, λem=455 nm). The relative fluorescent intensity was plotted as a function of logarithm of inhibitor concentrations.

Buffer Effect Measurement

To a solution of 20 μL, of 50 μM HADP (compound 1) and 160 μL different buffers was added 20 μL, 0.1 μg/μL heparanase to obtain 5 μM each compound with 2 μg heparanase solution in 96-well microplate. Each buffer was performed in triplicates. Then the microplate was sealed with sealing film and incubated at 37° C. Fluorescence intensity was recorded on Spectramax M5 Multimode plate reader (Molecular Devices, USA) at each timepoint. λex/em=365 nm/455 nm. Buffers: 40 mM NaOAc (pH 5.0); 40 mM NaOAc (pH 6.0); 50 mM MES with 10 mM NaCl (pH=6.0).

Time-Dependent Fluorescence Intensity with Varying Amounts of Heparanase

To a solution of 20 μL, of 50 μM HADP (compound 1) and 160 μL 40 mM NaOAc buffer (pH 5.0) buffers was added 20 μL, heparanase with various concentrations (0-0.1 μg/μL) in 96-well microplate. Then final concentration of heparanase is from 0-0.01 μg/μL. Each concentration was performed in triplicates. Then the fluorescence intensity was recorded on Spectramax M5 Multimode plate reader (Molecular Devices, USA) at each timepoint. λex/em=365 nm/455 nm.

Detection Limit Measurement

To calculate the detection limit, plot the fluorescence intensity against heparanase concentration and fit a line with linear regression. The detection limit was estimated with the following formula. LOD=3 σ/s, where σ represents standard deviation of fluorescent intensity of blank sample, s is the calculated slope of linear regression equation.

Preparation of (2-Azido-2-deoxy-1,3,5,6-tetra-O-acetyl-D-glucopyranose)

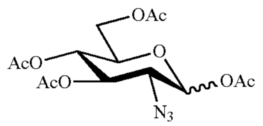

To a solution of D-glucosamine hydrochloride (8.625 g, 40 mmol) in water (40 mL), triethylamine (11 mL, 80 mmol) was added slowly followed by an addition of $CuSO_4 \cdot 5H_2O$ (100 mg, 0.4 mmol). Reaction mixture was then stirred at 0° C. To this solution in situ prepared $TfN_3$ solution (1.2 equiv) was added to it slowly which changed the color of the solution to dark brown. After 0.5 h reaction was stirred at room temperature for next 48 h. Then, reaction was concentrated under rotary-evaporator. In order to facilitate the removal of water, toluene was added and concentrated couple of times as a result of which thick residue was obtained. Thus, obtained crude mixture was directly employed for the next acetylation.

For the acetylation of the crude product, it was dissolved in DCM (80 mL)/$NEt_3$ (40 mL) and stirred at ice-cold temperature. To this solution acetic anhydride (21 mL, 224 mmol) was added slowly followed by DMAP (244 mg, 2 mmol). Reaction was stirred at room temperature for 16 h. After diluting with DCM and water, it was washed with 1N HCl followed by saturated $NaHCO_3$. Thus, obtained organic fraction was dried over anhydrous $Na_2SO_4$, concentrated and purified by column chromatography (Ethyl Acetate:

Hexane=1:5 to 1:2) to give a α/β mixture (α:β=0.39:1) of the desired compound as a viscous oil (7.520 g, 58%).

Preparation of $TfN_3$: To a flask containing sodium azide (3.74 g, 57.6 mmol), anhydrous acetonitrile was added and stirred at 0° C. To this solution triflic anhydride (8.1 mL, 48 mmol) was added and stirred for 2 h at 0° C. After 2 h, the reaction mixture was filtered through celite giving a $TfN_3$ solution in acetonitrile as a filtrate, which was directly added to the azidation transfer reaction.

$^1$H NMR (800 MHz, $CDCl_3$) β-isomer δ 5.51 (d, $J_{1,2}$=8.0 Hz, 1H, H-1), 5.05 (dd, $J_{3,4}$=$J_{3,2}$=9.6 Hz, 1H, H-3), 4.98 (dd, $J_{4,5}$=$J_{4,3}$=9.6 Hz, 1H, H-4), 4.24 (dd, $J_{6a,6b}$=12.0 Hz, $J_{6a,5}$=4.0 Hz, 1H, H-6a), 4.02 (d, J=12.0 Hz, 1H, H-6b), 3.77 (dd, $J_{5,4}$=9.6 Hz, $J_{5,6b}$=1.6 Hz, H-5), 3.61 (dd, $J_{2,3}$=9.6 Hz, 1H, H-2), 2.13 (s, 3H, $OCOCH_3$), 2.03 (s, 3H, $OCOCH_3$), 2.01 (s, 3H, $OCOCH_3$), 1.96 (s, 3H, $OCOCH_3$); $^{13}$C NMR (201 MHz, $CDCl_3$) δ 170.3 ($OCOCH_3$), 169.6 ($OCOCH_3$), 169.5 ($OCOCH_3$), 168.4 ($OCOCH_3$), 92.7 (C-1), 73.0 (C-3, C-5), 68.4 (C-4), 62.9 (C-2), 61.7 (C-6), 20.7 ($COOCH_3$), 20.5 ($COOCH_3$), 20.5 ($COOCH_3$), 20.4 ($COOCH_3$).

α-isomer δ 6.24 (d, J=3.2 Hz, H-1), 5.39 (dd, $J_{3,4}$=$J_{3,2}$=10.4 Hz, H-3), 5.05 (dd, $J_{4,5}$=$J_{4,3}$=9.6 Hz, H-4), 4.23-4.22 (m, H-6a), 3.99 (d, J=12.8 Hz, 1H, H-5), 3.63-3.60 (m, H-2), 2.04 (s, 3H, $OCOCH_3$), 1.98 (s, 3H, $OCOCH_3$). $^{13}$C NMR (201 MHz, $CDCl_3$) δ 169.8 ($OCOCH_3$), 169.4 ($OCOCH_3$), 168.3 ($OCOCH_3$), 90.1 (C-1), 70.9 (C-3), 70.0 (C-5), 68.5 (C-4), 61.7 (C-6), 60.7 (C-2) 20.7 ($COOCH_3$). HRMS (ESI) for $C_{14}H_{19}N_3O_9Na$ [M+Na]$^+$: Calcd: 396.1019, Found: 396.1012.

Preparation of (2-Azido-2-deoxy-3,5,6-tetra-O-D-glucopyranose)

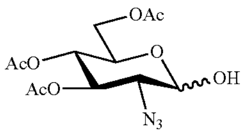

To a solution of 2-Azido-2-deoxy-1,3,5,6-tetra-O-D-glucopyranose (1886 mg, 5 mmol) in diethyl ether (10 mL) was added benzylamine (820 μL, 7.5 mmol, 1.5 equiv). Reaction was stirred at room temperature 4 hours. After the completion of the reaction, it was concentrated and diluted with ethyl acetate. Then it washed with 1N HCl, followed by washing with saturated $NaHCO_3$. Thus obtained crude product was dried over anhydrous $Na_2SO_4$, concentrated and purified by column chromatography (Ethyl Acetate: Hexane=1:3 to 1:2) to afford the desired compound (α:β=1: 0.58) as a yellow oil (1.36 g, 82%).

$^1$H NMR (800 MHz, $CDCl_3$) α-isomer δ 5.51 (dd, $J_{3,4}$=$J_{3,2}$=9.6 Hz, 1H, H-3), 5.38 (d, $J_{1,2}$=1.6 Hz, 1H, H-1), 5.04 (dd, $J_{4,5}$=$J_{4,3}$=9.6 Hz, 1H, H-4), 4.26 (d, $J_{5,4}$=11.2 Hz, 1H, H-5), 4.23 (dd, $J_{6a,6b}$=12.8 Hz, $J_{6a,5}$=4.0 Hz, 1H, H-6a), 4.10 (d, J=12.0 Hz, 1H, H-6b), 3.95 (s, 1H, —OH), 3.40 (dd, $J_{2,3}$=7.2 Hz, $J_{2,1}$=2.4 Hz, 1H, H-2), 2.08 (s, 3H, $OCOCH_3$), 2.07 (s, 6H, 2×$OCOCH_3$); $^{13}$C NMR (201 MHz, $CDCl_3$) δ 170.1 ($OCOCH_3$), 169.9 ($OCOCH_3$), 169.8 ($OCOCH_3$), 92.3 (C-1), 70.8 (C-3), 68.9 (C-4), 67.9 (C-5), 62.4 (C-6), 62.0 (C-2), 20.72 ($COOCH_3$), 20.70 ($COOCH_3$).

β-isomer δ 5.02-4.99 (m, 2H, H-3, H-4), 4.72 (d, $J_{1,2}$=7.2 Hz, 1H, H-1), 4.47 (s, 1H, —OH), 4.21-4.20 (m, 1H, H-6a), 4.13 (d, J=12.0 Hz, 1H, H-6b), 3.70-3.72 (m, 1H, H-5), 3.47 (dd, $J_{2,3}$=$J_{2,1}$=8.0 Hz, 1H, H-2) 2.03 (s, 2×$OCOCH_3$), 2.01 (s, $OCOCH_3$); $^{13}$C NMR (201 MHz, $CDCl_3$) δ 170.8 ($OCOCH_3$), 170.1 ($OCOCH_3$), 96.4 (C-1), 73.0 (C-4), 72.4 (C-5), 68.9 (C-3), 65.4 (C-2), 62.4 (C-6), 20.7 ($OCOCH_3$), 20.5 ($OCOCH_3$), 20.62 ($OCOCH_3$. HRMS (ESI) for $C_{12}H_{17}N_3O_8Na$ [M+Na]$^+$: Calcd: 354.0913, Found: 354.0911.

Preparation of (3, 4, 6-Tri-O-acetyl-2-azido-2-deoxy-α-D-glucopyranosyl trichloroacetimidate)

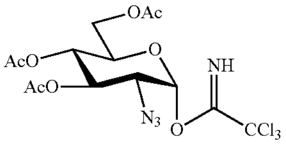

To a solution of 3,4,6-tri-O-acetyl-2-azido-2-deoxy-D-glucopyranose (663 mg, 2 mmol) in anhydrous dichloromethane (5 mL), trichloroacetonitrile (802 μL, 8 mmol) was added and stirred at 0° C. To this solution was added DBU (27.6 μL, 1.23 mmol). Then reaction was allowed to stir at room temperature. After the completion of the reaction (2 h), it was concentrated and purified by column chromatography to afford a white solid in 81% yield (770 mg).

$^1$H NMR (800 MHz, $CDCl_3$) δ 8.81 (s, 1H, =NH), 6.38 (d, $J_{1,2}$=4.0 Hz, 1H, H-1), 5.39 (dd, $J_{3,2}$=$J_{3,4}$=9.6 Hz, 1H, H-3), 5.03 (dd, $J_{4,3}$=$J_{4,5}$=9.6 Hz, 1H, H-4), 4.16 (dd, $J_{6a,6b}$=12.0 Hz, $J_{6a,5}$=4.0 Hz, 1H, H-6a), 4.11-4.10 (m, 1H, H-5), 3.98 (d, J=12.0 Hz, 1H, H-6b), 3.70 (dd, $J_{2,3}$=10.4 Hz, $J_{2,1}$=2.4 Hz, 1H, H-2), 1.99 (s, 3H, $OCOCH_3$), 1.94 (s, 6H, 2×$OCOCH_3$). $^{13}$C NMR (201 MHz, $CDCl_3$) δ 170.1 ($OCOCH_3$), 169.5 ($OCOCH_3$), 169.4 ($OCOCH_3$), 160.4 (C=NH), 94.1 (C-1), 70.7 (C-3), 70.3 (C-5), 68.3 (C-4), 61.5 (C-6), 60.8 (C-2), 20.4 ($OCOCH_3$), 20.3 ($OCOCH_3$), 20.2 ($OCOCH_3$). HRMS (ESI) for $C_{14}H_{17}C_{13}N_4O_8Na$ [M+Na]$^+$: Calcd: 497.0010, Found: 497.0010.

Preparation of D-(+)-Glucose Pentaacetate

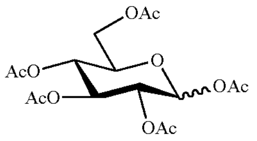

To a solution of D-(+)-Glucose (9 g, 50 mmol), DMAP (305 mg, 2.5 mmol) in pyridine (20 mL) was added Ac2O (28 mL, 300 mmol) slowly at 0° C. Then the reaction was allowed to stir at room temperature for 16 h. After the completion of the reaction, it was diluted with ethyl acetate and washed with 1N HCl for multiple times to remove pyridine which was followed by washing with saturated $NaHCO_3$. Thus, the obtained content was dried over anhydrous $Na_2SO_4$, concentrated and purified by column chromatography (Ethyl Acetate:Hexane=1:2) to afford a white solid (α:β=1:0.14, 18.5 g, 95%).

$^1$H NMR (800 MHz, $CDCl_3$) α-isomer δ 6.27 (d, $J_{1,2}$=4.0 Hz, 1H, H-1), 5.41 (dd, $J_{3,2}$=$J_{3,4}$=9.6 Hz, 1H, H-3), 5.08 (dd, $J_{4,3}$=$J_{4,5}$=9.6 Hz, 1H, H-4), 5.04 (dd, $J_{2,1}$=4.0 Hz, $J_{2,3}$=10.4 Hz, 1H, H-2), 4.21 (dd, $J_{6a,5}$=4.0 Hz, $J_{6a,6b}$=12.8 Hz, 1H, H-6a), 4.06 (ddd, $J_{5,6b}$=1.6 Hz, $J_{5,6a}$=3.2 Hz, $J_{5,4}$=9.6 Hz, 1H, H-5) 4.03 (dd, $J_{6b,5}$=1.6 Hz, $J_{6b,6a}$=12.0 Hz, 1H, H-6a), 2.12 (s, 3H, $COCH_3$), 2.03 (s, 3H, $COCH_3$), 1.98 (s, 3H, $COCH_3$), 1.97 (s, 3H, $COCH_3$), 1.96 (s, 3H, $COCH_3$); $^{13}C$ NMR (201 MHz, $CDCl_3$) α-isomer δ 170.3 ($OCOCH_3$), 170.0 ($OCOCH_3$), 169.5 ($OCOCH_3$), 169.3 ($OCOCH_3$), 168.3 ($OCOCH_3$), 89.4 (C-1), 70.2 (C-5), 70.1 (C-3), 69.6 (C-4), 68.5 (C-2), 61.9 (C-6), 20.7 ($—COCH_3$), 20.5 ($—COCH_3$), 20.4 ($—COCH_3$), 20.3 ($—COCH_3$); $^1H$ NMR (800 MHz, $CDCl_3$) β-isomer δ 5.66 (d, $J_{1,2}$=8.8 Hz, 1H, H-1), 5.20 (dd, $J_{3,4}=J_{3,2}$=9.8 Hz, 1H, H-3), 4.23 (dd, $J_{6a,5}$=4.8 Hz, $J_{6a,6b}$=12.8 Hz, 1H, H-6a), 3.80 (ddd, $J_{5,6b}$=2.4 Hz, $J_{5,6a}$=4.8 Hz, $J_{5,4}$=9.6 Hz, 1H, H-5), 2.05 (s, 3H, $COCH_3$), 2.02 (s, 3H, $COCH_3$), 1.97 (s, 3H, $COCH_3$), 1.95 (s, 3H, $COCH_3$). $^{13}C$ NMR (201 MHz, $CDCl_3$) β-isomer δ 92.1 (C-1), 73.1 (C-3); HRMS (ESI) for $C_{16}H_{22}O_{11}Na$ $[M+Na]^+$: Calcd: 413.1060, Found: 413.1062.

Preparation of p-Tolyl-2,3,4,6-tetra-O-acetyl-1-thio-β-D-glucopyranoside

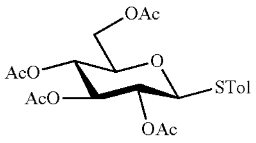

To a solution of α/β mixture of 1,2,3,4,6-penta-O-acetyl-glucopyranose (3.9 g, 10 mmol) and p-thiocresol (2.5 g, 20 mmol) in an anhydrous DCM (50 mL), was added $BF_3 \cdot Et_2O$ (1.9 mL, 15 mmol) and the solution was refluxed at 40° C. for 16 h. The reaction was quenched with sat. $NaHCO_3$, concentrated, washed with brine, dried over $Na_2SO_4$. The crude product was concentrated and purified with column chromatography (Hexanes:Ethyl Acetate=10:1 to 5:1 to 3:1 to 2:1) to provide the desired compound as a white solid (2.44 g, 54%).

$^1H$ NMR (800 MHz, $CDCl_3$) δ 7.36 (d, J=8.0 Hz, 2H, ArH), 7.09 (d, J=8.0 Hz, 2H, ArH), 5.18 (dd, $J_{3,4}=J_{3,2}$=8.8 Hz, 1H, H-3), 4.99 (dd, $J_{4,5}=J_{4,3}$=9.6 Hz, 1H, H-4), 4.90 (dd, $J_{2,1}=J_{2,3}$=9.6 Hz, 1H, H-2), 4.61 (d, $J_{1,2}$=10.4 Hz, 1H, H-1), 4.18 (dd, $J_{6a,6b}$=12.0 Hz, $J_{6a,5}$=4.8 Hz, 1H, H-6a), 4.15 (d, $J_{6b,6a}$=12.0 Hz, 1H, H-6b), 3.67 (ddd, $J_{5,4}$=9.6 Hz, $J_{5,6a}$=4.8 Hz, $J_{5,6b}$=2.4 Hz, 1H, H-5), 2.32 (s, 3H, $—CH_3$), 2.05 (s, 3H, $OCOCH_3$), 2.05 (s, 3H, $OCOCH_3$), 1,98 (s, 3H, $OCOCH_3$), 1.95 (s, 3H, $OCOCH_3$). $^{13}C$ NMR (201 MHz, $CDCl_3$) δ 170.3 ($OCOCH_3$), 170.0 ($OCOCH_3$), 169.3 ($OCOCH_3$), 169.1 ($OCOCH_3$), 138.8 (Ar), 134.0 (Ar), 129.7 (Ar), 128.1 (Ar), 86.1 (C-1), 76.2 (C-5), 74.4 (C-3), 70.5 (C-2), 68.9 (C-4), 62.5 (C-6), 21.1 ($—CH_3$), 20.6 ($OCOCH_3$), 20.5 ($OCOCH_3$), 20.4 ($2 \times OCOCH_3$). HRMS (ESI) for $C_{21}H_{26}O_9SNa$ $[M+Na]^+$: Calcd: 477.1195, Found: 477.1192.

Preparation of p-Tolyl-4,6-O-benzylidene-1-thio-β-D-glucopyranoside

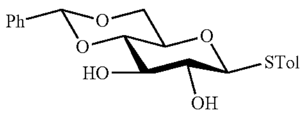

To a solution of p-Tolyl-2,3,4,6-tetra-O-acetyl-1-thio-β-D-glucopyranoside (2.44 mg, 5.37 mmol) in 10 mL of MeOH was added 122 μL of 25% NaOMe in MeOH. The mixture was stirred at room temperature for 1 h. Consumption of the starting material was monitored by TLC. Then, the reaction was quenched and neutralized by adding resin followed by filtration and concentration. The obtained crude product was directly used for next step without purification. To the acetonitrile solution of the crude product in acetonitrile (10 mL), benzaldehyde dimethyl acetal (1.2 mL, 8 mmol) and camphor sulfonic acid (CSA) (124 mg, 0.54 mmol) were added and stirred for 16 h at room temperature. Reaction was quenched with triethyl amine (TEA) and subjected to solvent evaporation. The resulting residue was purified by column chromatography (Hexanes:Ethyl Acetate=2:1 to 5% Methanol in DCM) to give the desired compound as a white solid (1.59 g, 79%).

$^1H$ NMR (800 MHz, $CDCl_3$) δ 7.47-7.46 (m, 2H) 7.43 (d, J=8.0 Hz, 2H), 7.36-7.35 (m, 3H), 7.14 (d, J=8.0 Hz, 2H), 5.48 (s, 1H), 4.52 (d, $J_{1,2}$=9.6 Hz, 1H, H-1), 4.34 (dd, $J_{6a,6b}$=10.4 Hz, $J_{6a,5}$=4.0 Hz, 1H, H-6a), 3.77 (dd, $J_{3,4}=J_{3,2=8.0}$ Hz, 1H, H-3), 3.72 (dd, $J_{6b,6a}=J_{6b,5}$=10.0 Hz, 1H, H-6b), 3.46-3.41 (m, 2H, H-5, H-4), 3.39 (dd, $J_{2,1}=J_{2,3}$=9.2 Hz, 1H, H-2), 3.33 (br, 1H, 3-OH), 3.08 (br, 1H, 2-OH), 2.36 (s, 3H, $—CH_3$). $^{13}C$ NMR (201 MHz, $CDCl_3$) δ 138.9, 137, 133.8, 130.0, 129.4, 128.4, 127.9, 126.5, 102.1, 89.0 (C-1), 80.6 (C-4), 74.9 (C-3), 73.0 (C-2), 70.8 (C-5), 68.8 (C-6), 21.2 ($—CH_3$). HRMS (ESI) for $C_{20}H_{22}O_5SNa$ $[M+Na]^+$: Calcd: 397.1086, Found: 397.1080.

Preparation of p-Tolyl-2,3-di-O-acetyl-4,6-O-benzylidene-1-thio-β-D-glucopyranoside

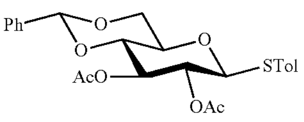

To a solution of p-Tolyl-4,6-benzylidene-1-thio-β-D-glucopyranoside (1.57 g, 4.2 mmol) and DMAP (25.7 mg, 0.21 mmol) in pyridine (5 mL) at 0° C. was added acetic anhydride (1.6 mL, 16.8 mmol). After the completion of reaction, pyridine was removed and ethyl acetate was added to the residue. The mixture was washed with 1N HCl and saturated NaHCO3 followed by brine. It was finally dried over anhydrous $Na_2SO_4$ and concentrated. The residue was subjected to the column chromatography (hexanes:ethyl acetate=2:1) to give the desired compound as a white solid (1.88 g, 98%).

$^1H$ NMR (800 MHz, $CDCl_3$) δ 7.43-7.42 (m, 2H), 7.37 (d, J=8.0 Hz, 2H), 7.35-7.34 (m, 3H), 7.15 (d, J=8.0 Hz, 2H), 5.49 (s, 1H), 5.33 (dd, $J_{3,2}=J_{3,4}$=9.2 Hz, 1H, H-3), 4.98 (dd, $J_{2,1}=J_{2,3}$=9.6 Hz, 1H, H-2), 4.74 (d, $J_{1,2}$=9.6 Hz, 1H, H-1), 4.38 (dd, $J_{6a,6b}$=10.4 Hz, $J_{6a,5}$=4.8 Hz, 1H, H-6a), 3.78 (dd, $J_{6b,6a}=J_{6b,5}$=10.4 Hz, 1H, H-6b), 3.64 (dd, $J_{4,5}=J_{4,3}$=9.2 Hz, 1H, H-4), 3.55 (ddd, $J_{5,4}=J_{5,6b}$=9.6 Hz, $J_{5,6a}$=4.8 Hz, 1H, H-5), 2.36 (s, 3H, $—CH_3$), 2.11 (s, 3H, $OCOCH_3$), 2.03 (s, 3H, $OCOCH_3$). $^{13}C$ NMR (201 MHz, $CDCl_3$) δ 170.0 ($OCOCH_3$), 169.5 ($OCOCH_3$), 138.9, 137.2, 133.9, 129.9, 129.2, 128.3, 128.2, 126.4, 101.8, 87.0 (C-1), 78.5 (C-4), 73.4 (C-3), 71.3 (C-2), 71.0 (C-5), 68.7 (C-6), 21.2 ($—CH_3$), 20.8 ($OCOCH_3$), 20.7 ($OCOCH_3$). HRMS (ESI) for $C_{24}H_{26}O_7S$ $[M+Na]^+$: Calcd: 481.1297, Found: 481.1300.

Preparation of p-Tolyl-2,3-di-O-acetyl-1-thio-β-D-glucopyranoside

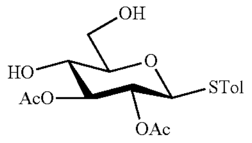

A solution of p-Tolyl-2,3-di-O-acetyl-4,6-benzylidene-1-thio-β-D-glucopyranoside (1.83 g, 4 mmol) in aqueous acetic acid (70%, 20 mL) was stirred at 80° C. for 2 hours. Then the mixture was diluted with ethyl acetate and washed with saturated $NaHCO_3$. The ethyl acetate fraction was washed with saturated NaCl solution and dried over anhydrous $Na_2SO_4$, followed by concentration. The resulting residue was purified by column chromatography (Hexanes: Ethyl Acetate=2:1 to 1:2 to 1:3) to give the desired compound as a white solid (1.38 g, 93%).

$^1$H NMR (800 MHz, $CDCl_3$) δ 7.35 (d, J=8.0 Hz, 2H), 7.12 (d, J=8.0 Hz, 2H), 5.04 (dd, $J_{3,4}$=$J_{3,2}$=9.2 Hz, 1H, H-3), 4.88 (dd, $J_{2,3}$=$J_{2,1}$=9.6 Hz, 1H, H-2), 4.67 (d, $J_{1,2}$=10.4 Hz, 1H, H-1), 3.90 (ddd, $J_{6a,6b}$=12.0 Hz, $J_{6a,6\text{-}OH}$=5.6 Hz, $J_{6a,5}$=3.2 Hz, 1H, H-6a), 3.79 (ddd, $J_{6b,6a}$=12.0 Hz, $J_{6b,6\text{-}OH}$=7.2 Hz, $J_{6b,5}$=4.0 Hz, 1H, H-6b), 3.69 (ddd, $J_{4,5}$=$J_{4,3}$=9.6 Hz, $J_{4,4\text{-}OH}$=5.6 Hz, 1H, H-4), 3.42 (ddd, $J_{5,4}$=9.6 Hz, $J_{5,6b}$=4.8 Hz, $J_{5,6a}$=3.2 Hz, 1H, H-5), 3.27 (d, J=5.6 Hz, 1H, 4-OH), 2.43 (dd, $J_{6\text{-}OH,6a}$=$J_{6\text{-}OH,6b}$=6.4 Hz, 1H, 6-OH), 2.33 (s, 3H, Ar—$CH_3$), 2.08 (s, 3H, $OCOCH_3$), 2.06 (s, 3H, $OCOCH_3$). $^{13}$C NMR (201 MHz, $CDCl_3$) δ 171.6 ($OCOCH_3$), 169.6 ($OCOCH_3$), 138.8, 133.5, 130.0, 128.4, 86.2 (C-1), 79.9 (C-5), 77.5 (C-3), 70.5 (C-2), 69.5 (C-4), 62.5 (C-6), 21.2 (Ar—$CH_3$), 20.9 ($OCOCH_3$), 20.8 ($OCOCH_3$) HRMS (ESI) for $C_{17}H_{22}O_7SNa$ [M+Na]$^+$: Calcd: 393.0984, Found: 393.0982.

Preparation of Methyl p-Tolyl (2,3-di-O-acetyl-1-thio-β-D-glucopyranosyluronate)

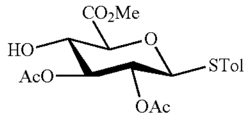

To the solution of p-tolyl-2,3-di-O-acetyl-1-thio-β-D-glucopyranoside (3.7 g, 10 mmol) and TEMPO (312.5 mg, 2 mmol) was added iodobenzene diacetate (8.0 g, 25 mmol) in DCM/$^t$BuOH/$H_2O$ (4:4:1, 45 mL). The reaction was stirred at room temperature for 5 h to afford uronic acid. Then reaction was quenched with saturated $Na_2S_2O_3$ and extracted with ethyl acetate followed by concentration. The residue was dissolved in DMF (40 mL). then $K_2CO_3$ (1.38 g, 10 mmol) and methyl iodide (1.6 mL, 25 mmol) were added to above solution. The reaction mixture was stirred at room temperature for 5 h. After the completion of reaction, the mixture was added with cold water, extracted with ethyl acetate and washed with water for multiple times and then with brine, followed by drying over anhydrous $Na_2SO_4$. The organic fraction was then concentrated and purified by column chromatography (Hexanes:Ethyl Acetate=5:1 to 2:1) to give the desired compound as a white solid (3.37 g, 85%).

$^1$H NMR (800 MHz, $CDCl_3$) δ 7.37 (d, J=8.0 Hz, 2H), 7.11 (d, J=8.0 Hz, 2H), 5.12 (dd, $J_{3,2}$=$J_{3,4}$=9.2 Hz, 1H, H-3), 4.88 (dd, J=9.6 Hz, 1H, H-2), 4.68 (d, $J_{1,2}$=9.6 Hz, 1H, H-1), 3.92 (d, $J_{5,4}$=9.6 Hz, 1H, H-5), 3.89 (ddd, $J_{4,5}$=$J_{4,3}$=10.4 Hz, $J_{4,4\text{-}OH}$=4.0 Hz, 1H, H-4), 3.82 (s, 3H, —$OCH_3$), 3.29 (d, $J_{4\text{-}OH,4}$=4.0 Hz, 1H, 4-OH), 2.32 (s, 3H, —$CH_3$), 2.07 (s, 3H, $OCOCH_3$), 2.04 (s, 3H, $OCOCH_3$). $^{13}$C NMR (201 MHz, $CDCl_3$) δ 170.7 ($OCOCH_3$), 169.3 ($OCOCH_3$), 168.9 ($COOCH_3$), 138.8, 133.7, 129.9, 128.2, 87.0 (C-1), 78.2 (C-5), 75.9 (C-3), 70.2 (C-2,4), 52.8 ($COOCH_3$), 21.2 (—$CH_3$), 20.7 (2×$OCOCH_3$). HRMS (ESI) for $C_{18}H_{22}O_8SNa$ [M+Na]$^+$: Calcd: 421.0933, Found: 421.0939.

Preparation of Intermediate 6 (Methyl p-Tolyl (2,3-di-O-acetyl-1-thio-β-D-glucopyranosyluronate)

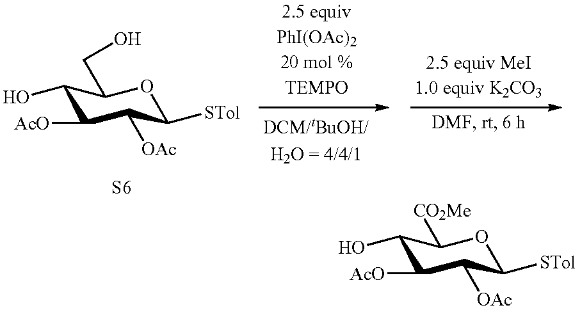

S6

6

To a solution of p-tolyl-2,3-di-O-acetyl-1-thio-β-D-glucopyranoside (S6, 3.7 g, 10 mmol) and TEMPO (312.5 mg, 2 mmol) was added iodobenzene diacetate (8.0 g, 25 mmol) in DCM/$^t$BuOH/$H_2O$ (4:4:1, 45 mL). The reaction was stirred at room temperature for 5 h to afford uronic acid. Then reaction was quenched with saturated $Na_2S_2O_3$ and extracted with ethyl acetate followed by concentration. The residue was dissolved in DMF (40 mL). then $K_2CO_3$ (1.38 g, 10 mmol) and methyl iodide (1.6 mL, 25 mmol) were added to above solution. The reaction mixture was stirred at room temperature for 5 h. After the completion of reaction, the mixture was added with cold water, extracted with ethyl acetate and washed with water for multiple times and then with brine, followed by drying over anhydrous $Na_2SO_4$. The organic fraction was then concentrated and purified by column chromatography (Hexanes:Ethyl Acetate=5:1 to 2:1) to give the desired compound as a white solid (3.37 g, 85%).

$^1$H NMR (800 MHz, $CDCl_3$) δ 7.37 (d, J=8.0 Hz, 2H), 7.11 (d, J=8.0 Hz, 2H), 5.12 (dd, $J_{3,2}$=$J_{3,4}$=9.2 Hz, 1H, H-3), 4.88 (dd, J=9.6 Hz, 1H, H-2), 4.68 (d, $J_{1,2}$=9.6 Hz, 1H, H-1), 3.92 (d, $J_{5,4}$=9.6 Hz, 1H, H-5), 3.89 (ddd, $J_{4,5}$=$J_{4,3}$=10.4 Hz, $J_{4,4\text{-}OH}$=4.0 Hz, 1H, H-4), 3.82 (s, 3H, —$OCH_3$), 3.29 (d, $J_{4\text{-}OH,4}$=4.0 Hz, 1H, 4-OH), 2.32 (s, 3H, —$CH_3$), 2.07 (s, 3H, $OCOCH_3$), 2.04 (s, 3H, $OCOCH_3$). $^{13}$C NMR (201 MHz, $CDCl_3$) δ 170.7 ($OCOCH_3$), 169.3 ($OCOCH_3$), 168.9 ($COOCH_3$), 138.8, 133.7, 129.9, 128.2, 87.0 (C-1), 78.2 (C-5), 75.9 (C-3), 70.2 (C-2,4), 52.8 ($COOCH_3$), 21.2 (—$CH_3$), 20.7 (2×$OCOCH_3$). HRMS (ESI) for $C_{18}H_{22}O_8SNa$ [M+Na]$^+$: Calcd: 421.0933, Found: 421.0939.

Preparation of Intermediate 7 (Methyl p-Tolyl (3',4',6'-tri-O-acetyl-2'-azido-2'-deoxy-α-D-glucopyranosyl)-(1→4)-(2,3-di-O-acetyl-1-thio-β-D-glucopyranosyluronate)

7

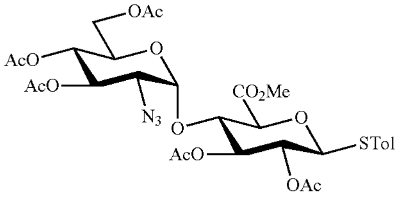

6-Tri-O-acetyl-2-azido-2-deoxy-α-D-glucopyranosyl trichloroacetimidate (951 mg, 2 mmol) and Methyl p-Tolyl (2,3-di-O-acetyl-1-thio-β-D-glucopyranosyluronate (398.4 mg, 1 mmol) were added into a dry round bottom flask and kept under high vacuum for 0.5 h. Then the flask was flushed with nitrogen and sealed with a rubber septum. Anhydrous toluene (4 mL) and dioxane (2 mL) were added and stirred for 30 min. The reaction mixture was then maintained at 0° C. for addition of TMSOTf (18 μL, 0.1 mmol). After 0.5 h the reaction was allowed to stir at room temperature for next 2 h. The reaction was quenched with triethyl amine (TEA) and filtered, concentrated. Then residue was purified by column chromatography (Hexane:Ethyl Acetate=3:1 to 2:1) to give the desired compound as a white solid (560.8 mg, 79%).

$^1$H NMR (800 MHz, $CDCl_3$) δ 7.33 (d, J=8.0 Hz, 2H), 7.11 (d, J=7.2 Hz, 2H), 5.30-5.27 (m, 2H, H-3, H-3'), 5.14 (d, $J_{1',2'}$=3.2 Hz, 1H, H-1'), 4.98 (dd, $J_{4',3'}$=$J_{4',5'}$=10.4 Hz, 1H, H-4'), 4.80 (dd, $J_{2,3}$=9.6 Hz, 1H, H-2), 4.69 (d, $J_{1,2}$=10.4 Hz, 1H, H-1), 4.23 (dd, $J_{6a',6b'}$=12.8 Hz, $J_{6d,5'}$=3.2 Hz, 1H, H-6a'), 4.12 (dd, $J_{4,3}$=$J_{4,5}$=9.6 Hz, 1H, H-4), 4.06 (d, J=12 Hz, 1H, H-6b'), 3.99 (d, $J_{5,4}$=9.6 Hz, 1H, H-5), 3.79-3.77 (m, 4H, $COOCH_3$, H-5'), 3.34 (dd, $J_{2,3}$=10.4 Hz, $J_{2,1}$=3.2 Hz, 1H, H-2'), 2.33 (s, 3H, —$CH_3$), 2.06 (s, 3H, $COCH_3$), 2.05 (s, 3H, $COCH_3$), 2.03 (s, 3H, $COCH_3$), 2.01 (s, 3H, $COCH_3$), 1.99 (s, 3H, $COCH_3$). $^{13}$C NMR (201 MHz, $CDCl_3$) δ 170.5 ($OCOCH_3$), 169.7 ($OCOCH_3$), 169.5 (2×$OCOCH_3$), 169.4 ($OCOCH_3$), 167.7 ($COOCH_3$), 138.9, 133.9, 129.9, 127.7, 98.7 (C-1'), 86.7 (C-1), 78.0 (C-5), 76.0 (C-4), 75.3 (C-3), 70.6 (C-3'), 70.5 (C-2), 68.8 (C-5'), 68.6 (C-4'), 61.3 (C-6'), 61.3 (C-2'), 52.8 (—$COOCH_3$), 21.2 (—$CH_3$), 20.7 (2×$COCH_3$), 20.6 (2×$COCH_3$), 20.5 (—$COCH_3$). HRMS (ESI) for $C_{30}H_{37}N_3O_{15}SNa$ $[M+Na]^+$: Calcd: 734.1843, Found: 734.1859.

Preparation of Intermediate 8 (Methyl (3',4',6'-Tri-O-acetyl-2'-azido-2'-deoxy-α-D-glucopyranosyl)-(1→4)-(1-bromo-1-deoxyl-2,3-di-O-acetyl-β-D-glucopyranosyluronate)

8

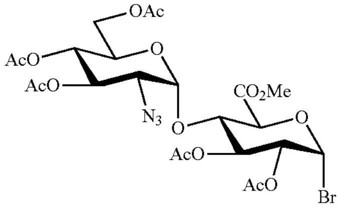

To a solution of Intermediate 7 (569 mg, 0.8 mmol) in anhydrous dichloromethane (5 mL), freshly prepared 1M IBr solution (0.9 mL, 0.90 mmol, prepared in anhydrous dichloromethane) was added and stirred at room temperature for 0.5 h under dark condition. After the completion of the reaction it was quenched with saturated $Na_2S_2O_3$ and extracted with DCM. Thus, the organic fraction was concentrated and subjected to column chromatography (Hexane:Ethyl Acetate=2:1) for purification to give the desired compound as a white solid (394 mg, 74%).

$^1$H NMR (800 MHz, $CDCl_3$) δ $^1$H NMR (800 MHz, $CDCl_3$) δ 6.52 (d, $J_{1,2}$=4.0 Hz, 1H, H-1), 5.65 (dd, $J_{3,2}$=$J_{3,4}$=9.6 Hz, 1H, H-3), 5.34 (dd, $J_{3',4'}$=$J_{3',2'}$=9.6 Hz, 1H, H-3'), 5.16 (d, $J_{1',2'}$=4.0 Hz, 1H, H-1'), 5.01 (dd, $J_{4',5'}$=$J_{4',3'}$=9.6 Hz, 1H, H-4'), 4.78 (dd, $J_{2,3}$=9.6 Hz, $J_{2,1}$=4.0 Hz, 1H, H-2), 4.53 (d, $J_{5,4}$=9.6 Hz, 1H, H-5), 4.24-4.21 (m, 2H, H-4, H-6a'), 4.08 (dd, $J_{6b',6a'}$=12.8 Hz, $J_{6b',5'}$=1.6 Hz, 1H, H-6b'), 3.87 (d, J=9.6 Hz, 1H, H-5'), 3.81 (s, 3H, —$COOCH_3$), 3.45 (dd, $J_{2',3'}$=10.4, $J_{2'1'}$=4.0 Hz, 1H, H-2'), 2.08 (s, 9H, $COCH_3$), 2.06 (s, 3H, $COCH_3$), 2.02 (s, 3H, $COCH_3$). $^{13}$C NMR (201 MHz, $CDCl_3$) δ 170.6 ($OCOCH_3$), 169.9 ($OCOCH_3$), 169.7 ($OCOCH_3$), 169.6 ($OCOCH_3$), 169.0 ($OCOCH_3$), 167.6 ($COOCH_3$), 98.8 (C-1'), 85.5 (C-1), 75.9 (C-4), 74.1 (C-5), 71.1 (C-2), 70.8 (C-3), 70.6 (C-3'), 69.1 (C-5'), 68.5 (C-4'), 61.5 (C-6'), 61.4 (C-2'), 53.2 (—$COOCH_3$), 20.7 (2×$COCH_3$), 20.6 (3×$COCH_3$). HRMS (ESI) for $C_{23}H_{30}BrN_3O_{15}Na$ $[M+Na]^+$: Calcd: 690.0758, Found: 690.0771.

Preparation of Intermediate 9a (4'-methylumbelliferyl-3,4,6-Tri-O-acetyl-2-azido-2-deoxy-α-D-glucopyranosyl-(1→4)-methyl 2,3-di-O-acetyl-β-D-glucopyranosyluronate)

9a

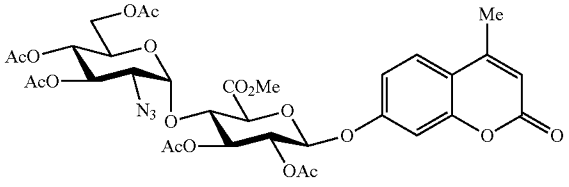

General Procedure for the glycosylation of disaccharide and fluorescent tag. To the solution of the disaccharide bromide and fluorescent tag in anhydrous MeCN was added silver oxide (2 equiv or 17 equiv) at room temperature under dark condition. After the completion of the reaction it was filtered and concentrated. The residue was purified with column chromatography (Hexane:Ethyl Acetate=1:1 to 1:3) to give the desired compound.

$^1$H NMR (500 MHz, $CDCl_3$) δ 7.55 (d, J=8.5 Hz, 1H), 6.96-6.92 (m, 2H), 6.22 (s, 1H), 5.41 (t, J=8.5 Hz, 1H, H-3), 5.38 (t, J=10.0 Hz, 1H, H-3'), 5.34 (d, J=6.5 Hz, 1H, H-1), 5.27 (d, J=3.5 Hz, 1H, H-1'), 5.20 (dd, J=8.5, 6.5 Hz, 1H, H-2), 5.04 (t, J=10.0 Hz, 1H, H-4'), 4.43 (t, J=8.5 Hz, 1H, H-4), 4.30 (d, J=9.0 Hz, 1H, H-5), 4.27 (dd, J=9.0 Hz, 3.5 Hz, 1H, H-6'), 4.11 (dd, J=12.5, 1.5 Hz, 1H, H-6'), 3.90 (ddd, J=10.5, 2.0, 2.0 Hz, 1H, H-5'), 3.72 (s, 3H), 3.43 (dd, J=11.0, 4.0 Hz, 1H, H-2'), 2.42 (s, 3H), 2.12 (s, 3H), 2.10 (s, 3H), 2.09 (s, 6H), 2.05 (s, 3H). $^{13}$C NMR (126 MHz, $CDCl_3$) δ 170.75, 169.97, 169.74, 169.73, 169.68, 167.52, 160.97, 158.98, 154.81, 152.33, 125.88, 115.68, 113.61, 113.32, 104.28, 98.90, 98.19, 75.11, 74.04, 72.96, 71.30, 70.11, 68.57, 68.03, 61.22, 60.86, 53.09, 20.82, 20.75, 20.70, 18.83.

Preparation of Intermediate 9c (8'-formyl-4'-methylumbelliferyl-3,4,6-Tri-O-acetyl-2-azido-2-deoxy-α-D-glucopyranosyl-(1→4)-methyl 2,3-di-O-acetyl-β-D-glucopyranosyluronate)

9c

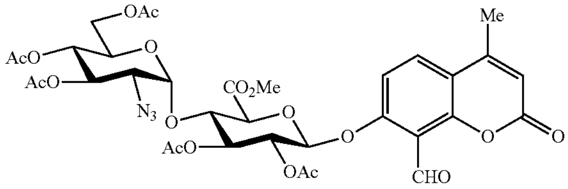

Intermediate 9c was prepared according to the procedure to prepare Intermediate 9a.

$^1$H NMR (800 MHz, $CDCl_3$) δ 10.50 (s, 1H, —CHO), 7.69 (d, J=8.8 Hz, 1H), 7.06 (d, J=8.8 Hz, 1H), 6.20 (s, 1H), 5.36 (d, $J_{1,2}$=5.6 Hz, 1H, H-1), 5.32 (dd, $J_{3',2'}$=$J_{3',4'}$=10.0 Hz, 1H, H-3'), 5.28 (dd, $J_{3,2}$=$J_{3,4}$=7.6 Hz, 1H, H-3), 5.19 (d, $J_{1',2'}$=4.0 Hz, 1H, H-1'), 5.17 (dd, $J_{2,1}$=6.0 Hz, $J_{2,3}$=7.6 Hz, 1H, H-2), 4.97 (dd, $J_{4',5'}$=$J_{4',3'}$=10.0 Hz, 1H, H-4'), 4.43 (dd, $J_{4,5}$=$J_{4,3}$=8.0 Hz, 1H, H-4), 4.31 (d, $J_{5,4}$=8.0 Hz, 1H, H-5), 4.17 (dd, $J_{6d,6b'}$=12.0 Hz, $J_{6a',5}$=4.0 Hz, 1H, H-6a'), 4.05 (dd, $J_{6b',6a'}$=12.8 Hz, $J_{6a',5}$=1.6 Hz, 1H, H-6b'), 3.87 (d, $J_{5',4'}$=9.6 Hz, 1H, H-5'), 3.62 (s, 3H, $CO_2CH_3$), 3.36 (dd, $J_{2',3'}$=10.8 Hz, $J_{2',1'}$=3.6 Hz, 1H, H-2'), 2.37 (s, 3H, $CH_3$), 2.07 (s, 3H, $OCOCH_3$), 2.06 (s, 3H, $OCOCH_3$), 2.02 (s, 3H, $OCOCH_3$), 2.01 (s, 3H, $OCOCH_3$), 1.97 (s, 3H, $OCOCH_3$). $^{13}$C NMR (201 MHz, $CDCl_3$) δ 186.1 (CHO), 170.5 ($OCOCH_3$), 169.9 ($OCOCH_3$), 169.7 ($OCOCH_3$), 169.6 (2×$OCOCH_3$), 167.8 ($CO_2$Me), 159.2 (=$CHCO_2$Ar), 159.0, 155.3, 151.4, 130.1, 116.1, 115.0, 114.2, 112.1, 98.8 (C-1'), 98.6 (C-1), 74.8 (C-4), 74.4 (C-5), 72.1 (C-3), 70.9 (C-2), 70.6 (C-3'), 69.1 (C-5'), 68.8 (C-4'), 61.8 (C-6'), 61.5 (C-2'), 52.9 ($CO_2CH_3$), 20.8 ($OCOCH_3$), 20.7 (3×$OCOCH_3$), 20.6 ($OCOCH_3$), 18.8. HRMS (ESI) for $C_{34}H_{37}N_3O_{19}Na$ $[M+Na]^+$: Calcd: 814.1919, Found: 814.1913.

Preparation of Intermediate 9d ((2R,3S,4R,5R,6R)-2-(acetoxymethyl)-5-azido-6-(((2S,3S,5R,6S)-4,5-diacetoxy-6-((8-(difluoromethyl)-4-methyl-2-oxo-2H-chromen-7-yl)oxy)-2-(methoxycarbonyl) tetrahydro-2H-pyran-3-yl)oxy)tetrahydro-2H-pyran-3,4-diyl diacetate)

9d

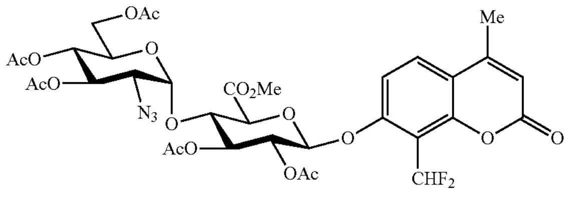

To a solution of 8'-formyl-4'-methylumbelliferyl-3,4,6-Tri-O-acetyl-2-azido-2-deoxy-α-D-glucopyranosyl-(1→4)-methyl 2,3-di-O-acetyl-β-D-glucopyranosyluronate. (67 mg, 0.085 mmol) in dry DCM (2 mL) was added DAST (37 μL, 0.255 mmol, 3 equiv) at room temperature under argon, the reaction mixture was stirred at room temperature for 18 h. Then the mixture was quenched with ice water. After separation, the aqueous phase was extracted with DCM, and the combined organic phases were dried over $Na_2SO_4$ and concentrated. The resulting residue was purified by column chromatography ((Hexanes:Ethyl Acetate=1/1-1/2)) to give the desired compound as a white solid (62.1 mg, 90%).

$^1$H NMR (800 MHz, $CDCl_3$) δ 7.62 (d, J=8.8 Hz, 1H), 7.14 (t, $J_{H,F}$=51.2 Hz, 1H), 7.06 (d, J=8.8 Hz, 1H), 6.17 (s, 1H), 5.33-5.32 (m, 2H, H-1, H-3'), 5.27 (dd, $J_{3,2}$=$J_{3,4}$=7.6 Hz, 1H, H-3), 5.18 (d, 1H, $J_{1',2'}$=3.2 Hz, H-1'), 5.16 (dd, $J_{2,3}$=$J_{2,1}$=7.2 Hz, H-2), 4.96 (dd, $J_{4',3'}$=$J_{4',5'}$=10.0 Hz, 1H, H-4'), 4.41 (dd, $J_{4,3}$=$J_{4,5}$=7.6 Hz, 1H, H-4), 4.33 (d, $J_{5,4}$=7.2 Hz, 1H, H-5), 4.17 (dd, $J_{6a',6b'}$=12.8 Hz, $J_{6a',5}$=2.4 Hz, 1H, H-6a'), 4.06 (d, $J_{6b',6a'}$=12.0 Hz, 1H, H-6b'), 3.89 (dd, $J_{5',4'}$=8.8 Hz, $J_{5',6a'}$=1.6 Hz, 1H, H-5'), 3.62 (s, 3H, $CO_2CH_3$), 3.36 (dd, $J_{2',3'}$=10.4, $J_{2',1'}$=1.6 Hz, 1H, H-2'), 2.36 (s, 3H, $CH_3$), 2.04 (s, 6H, 2×$OCOCH_3$), 2.02 (s, 6H, 2×$OCOCH_3$), 1.97 (s, 3H, $OCOCH_3$). $^{13}$C NMR (201 MHz, $CDCl_3$) δ 170.5 ($OCOCH_3$), 169.8 ($OCOCH_3$), 169.6 ($OCOCH_3$), 169.5 ($OCOCH_3$), 169.4 ($OCOCH_3$), 167.7 ($CO_2CH_3$), 159.0, 157.9, 153.0, 151.6, 128.2, 116.0, 114.1, 111.9, 110.04 (t, $J_{CF}$=239.4 Hz, $CHF_2$), 98.8 (C-1'), 98.6 (C-1), 74.9 (C-4), 74.3 (C-5), 72.0 (C-3), 70.6 (C-3', C-2), 69.1 (C-5'), 68.9 (C-4'), 61.8 (C-6'), 61.5 (C-2'), 52.9 ($CO_2CH_3$), 20.7 ($OCOCH_3$), 20.6 (2×$OCOCH_3$), 20.5 (2×$OCOCH_3$), 18.7. HRMS (ESI) for $C_{34}H_{37}F_2N_3O_{18}Na$ $[M+Na]^+$: Calcd: 836.1938, Found: 836.1961.

Preparation of Intermediate 9e ((2R,3S,4R,5R,6R)-2-(acetoxymethyl)-5-azido-6-(((2S,3S,5R,6S)-4,5-diacetoxy-6-((6,8-difluoro-4-methyl-2-oxo-2H-chromen-7-yl)oxy)-2-(methoxycarbonyl)tetrahydro-2H-pyran-3-yl)oxy)tetrahydro-2H-pyran-3,4-diyl diacetate)

9e

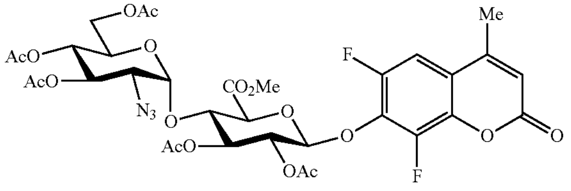

Intermediate 9e was prepared according to the procedure to prepare Intermediate 9a.

$^1$H NMR (500 MHz, $CDCl_3$) δ 7.15 (d, $J_{H-F}$=10.5 Hz, 1H), 6.34 (s, 1H), 5.36 (m, 2H, H-3, H-3'), 5.31 (d, J=7.5 Hz, 1H, H-1), 5.25 (t, J=7.5 Hz, 1H, H-2), 5.22 (d, J=3.0 Hz, 1H, H-1'), 5.03 (t, J=9.5 Hz, 1H, H-4'), 4.39 (t, J=9.0 Hz, 1H, H-4), 4.26 (dd, J=12.5, 2.6 Hz, 1H, H-6'), 4.13 (d, J=9.4 Hz, 1H, H-5), 4.09 (d, J=12.5 Hz, 1H, H-6'), 3.86-3.81 (m, 1H, H-5'), 3.79 (s, 3H), 3.42 (dd, J=10.6, 3.0 Hz, 1H), 2.40 (s, 3H), 2.12 (s, 3H), 2.11 (s, 3H), 2.09 (s, 3H), 2.07 (s, 3H), 2.02 (s, 3H). $^{13}$C NMR (126 MHz, $CDCl_3$) δ 170.73, 169.94, 169.71, 169.67, 167.30, 158.77, 151.29 (dd, J=248.2, 2.5 Hz), 151.14, 143.37 (d, J=257.0, 4.8 Hz), 139.65 (dd, J=10.2, 2.5 Hz), 135.17 (dd, J=11.5, 16.0 Hz), 116.89 (d, J=8.7 Hz), 116.01, 105.99 (dd, J=21.9, 3.7 Hz), 101.45, 98.90, 75.66, 74.43, 73.28, 71.39, 70.20, 68.67, 68.08, 61.21, 60.97, 53.16, 20.79, 20.74, 20.68, 18.87.

General Procedure for Global Deacetylation, Saponification, Reduction, and Sulfation To a solution of disaccharide with fluorescent tag in MeOH was added NaOMe (25% w/w NaOMe in MeOH, 0.2 equiv). Then reaction process was monitored with HPLC. When all the acetyl group was removed, 20 wt % Pd/C was added to the mixture. Then evacuate and back-fill the flask with hydrogen balloon. After completion of hydrogenation monitored with HPLC, the methanol was removed. Then the flask was charged with THF/$H_2O$=1/2, the pH of the solution was adjusted to 11 with 1M NaOH and maintained until the methyl group was removed. Finally, Py•$SO_3$ (10 equiv) was added in portions to above solution and the pH of the solution was maintained between 9-10. After completion of sulfation, the mixture was purified with HPLC to afford desired product after lyophilization.

Preparation of Compound 2 ((2S,3S,4R,5R,6S)-3-(((2R,3R,4R,5S,6R)-3-((hydrosulfonyloxy)amino)-4,5-dihydroxy-6-(hydroxymethyl)tetrahydro-2H-pyran-2-yl)oxy)-4,5-dihydroxy-6-((4-methyl-2-oxo-2H-chromen-7-yl)oxy)tetrahydro-2H-pyran-2-carboxylic acid)

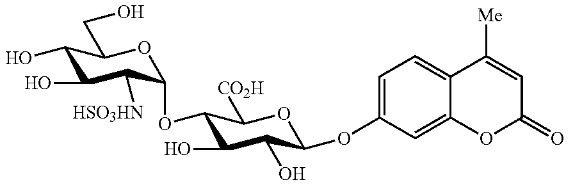

2

The titled compound was prepared according to the General Procedure for Global Deacetylation, Saponification, Reduction, and Sulfation above.

$^1$H NMR (600 MHz, $D_2O$) δ 7.67 (d, J=8.9 Hz, 1H), 7.09 (dd, J=8.9, 2.2 Hz, 1H), 7.05 (s, 1H), 6.21 (s, 1H), 5.70 (d, J=3.4 Hz, 1H), 5.27 (d, J=7.9 Hz, 1H), 4.05 (d, J=9.6 Hz, 1H), 4.01 (t, J=9.1 Hz, 1H), 3.93 (t, J=9.3 Hz, 1H), 3.89-3.79 (m, 2H), 3.78-3.74 (m, 1H), 3.72 (t, J=8.7 Hz, 1H), 3.65 (t, J=9.8 Hz, 1H), 3.52 (t, J=9.6 Hz, 1H), 3.28 (dd, J=10.4, 3.6 Hz, 1H), 2.41 (s, 3H). $^{13}$C NMR (151 MHz, $D_2O$) δ 174.51, 164.56, 163.36, 163.13, 162.89, 162.66, 159.38, 156.25, 153.81, 126.70, 119.22, 117.29, 115.36, 115.28, 113.85, 113.42, 111.23, 103.59, 99.40, 97.34, 76.79, 76.12, 75.96, 72.46, 71.62, 71.20, 69.60, 60.08, 58.04, 17.96.

$^1$H NMR (500 MHz, $D_2O$) δ 7.75 (d, J=8.7 Hz, 1H), 7.13 (d, J=11.3 Hz, 2H), 6.28 (s, 1H), 5.67 (d, J=3.6 Hz, 1H), 5.33 (d, J=7.8 Hz, 1H), 4.25 (d, J=9.4 Hz, 1H), 4.02 (t, J=9.0 Hz, 1H), 3.97 (t, J=9.1 Hz, 1H), 3.85-3.76 (m, 2H), 3.73 (t, J=8.5 Hz, 1H), 3.67-3.59 (m, 2H), 3.53 (t, J=9.5 Hz, 1H), 3.28 (dd, J=10.3, 3.7 Hz, 1H), 2.46 (s, 3H). $^{13}$C NMR (126 MHz, $D_2O$) δ 172.57, 164.53, 159.10, 156.14, 153.82, 126.60, 115.43, 113.67, 111.28, 103.58, 99.25, 97.58, 76.03, 75.41, 74.98, 72.19, 71.82, 70.97, 69.24, 59.83, 57.80, 17.81.

Preparation of Compound 4 ((2S,3S,4R,5R,6S)-3-(((2R,3R,4R,5S,6R)-4,5-dihydroxy-6-((sulfooxy)methyl)-3-(((E)-trioxidaneyl-14-sulfaneylidene)amino)tetrahydro-2H-pyran-2-yl)oxy)-4,5-dihydroxy-6-((4-methyl-2-oxo-2H-chromen-7-yl)oxy)tetrahydro-2H-pyran-2-carboxylic acid)

4

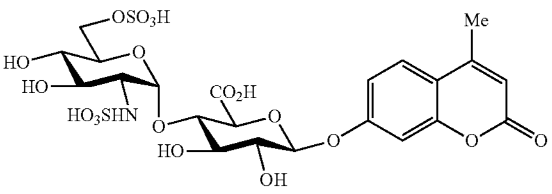

The titled compound was prepared according to the General Procedure For Global Deacetylation, Saponification, Reduction, and Sulfation above.

$^1$H NMR (500 MHz, $D_2O$) δ 7.80 (d, J=9.0 Hz, 1H), 7.19-7.15 (m, 2H), 6.32 (s, 1H), 5.68 (d, J=3.5 Hz, 1H), 5.32 (d, J=8.0 Hz, 1H), 4.34 (dd, J=11.0, 2.0 Hz, 1H), 4.21-4.17 (m, 2H), 4.03-3.94 (m, 2H), 3.84 (d, J=9.0 Hz, 1H), 3.73 (t, J=8.0 Hz, 1H), 3.65-3.56 (m, 2H), 3.31 (d, J=10.0, 3.0 Hz, 1H), 2.49 (s, 3H).

Preparation of Compound 1 (HADP) ((2S,3S,4R,5R,6S)-6-((6,8-difluoro-4-methyl-2-oxo-2H-chromen-7-yl)oxy)-3-(((2R,3R,4R,5S,6R)-3-((hydrosulfonyloxy)amino)-4,5-dihydroxy-6-(hydroxymethyl)tetrahydro-2H-pyran-2-yl)oxy)-4,5-dihydroxytetrahydro-2H-pyran-2-carboxylic acid)

1

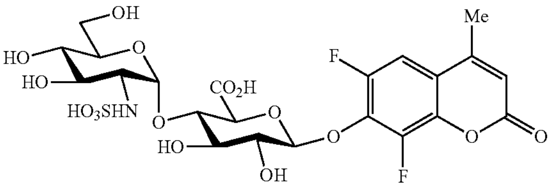

The titled compound was prepared according to the General Procedure For Global Deacetylation, Saponification, Reduction, and Sulfation above.

$^1$H NMR (500 MHz, $D_2O$) δ 7.47 (d, J=11.0 Hz, 1H), 6.44 (s, 1H), 5.65 (d, J=2.5 Hz, 1H, H-1'), 5.26 (d, J=7.5 Hz, 1H, H-1), 4.05 (d, J=8.0 Hz, 1H, H-5), 3.99-3.93 (m, 2H, H-3, H-4), 3.82-3.73 (m, 3H, H-2), 3.60-3.52 (m, 3H, H-3'), 3.26 (dd, J=10.5, 3.5 Hz, 1H, H-2'), 2.44 (s, 3H).

Preparation of Compound 3 ((2S,3S,4R,5R,6S)-6-((8-(difluoromethyl)-4-methyl-2-oxo-2H-chromen-7-yl)oxy)-3-(((2R,3R,4R,5S,6R)-3-((hydrosulfonyloxy)amino)-4,5-dihydroxy-6-(hydroxymethyl) tetrahydro-2H-pyran-2-yl)oxy)-4,5-dihydroxytetrahydro-2H-pyran-2-carboxylic acid)

3

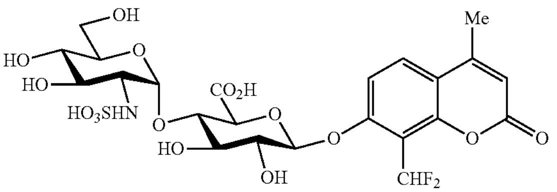

The titled compound was prepared according to the General Procedure For Global Deacetylation, Saponification, Reduction, and Sulfation above.

$^{1}H$ NMR (500 MHz, $D_2O$) δ 7.68 (d, J=9.0 Hz, 1H), 7.25 (t, J=52.9 Hz, 2H), 7.11 (d, J=9.0 Hz, 1H), 6.18 (s, 1H), 5.63 (d, J=4.0 Hz, 1H), 5.32 (d, J=7.5 Hz, 1H), 4.31-4.29 (m, 1H), 4.00-3.98 (m, 2H), 3.79-3.74 (m, 3H), 3.60-3.52 (m, 3H), 3.25 (dd, J=10.0 Hz, 3.5 Hz, 1H), 2.30 (s, 3H). $^{13}C$ NMR (126 MHz, $D_2O$) δ 171.4, 162.7, 156.9, 155.4, 151.3, 129.3, 115.3, 111.8, 111.6, 110.3 (t, J=234 Hz), 109.7 (t, 22.7 Hz) 99.5, 97.9, 76.2, 75.1, 74.1, 72.0, 71.9, 70.90, 69.1, 59.7, 57.7, 17.8.

Activation of Compounds 1-4 By Recombinant Heparanase

Figure 4A:
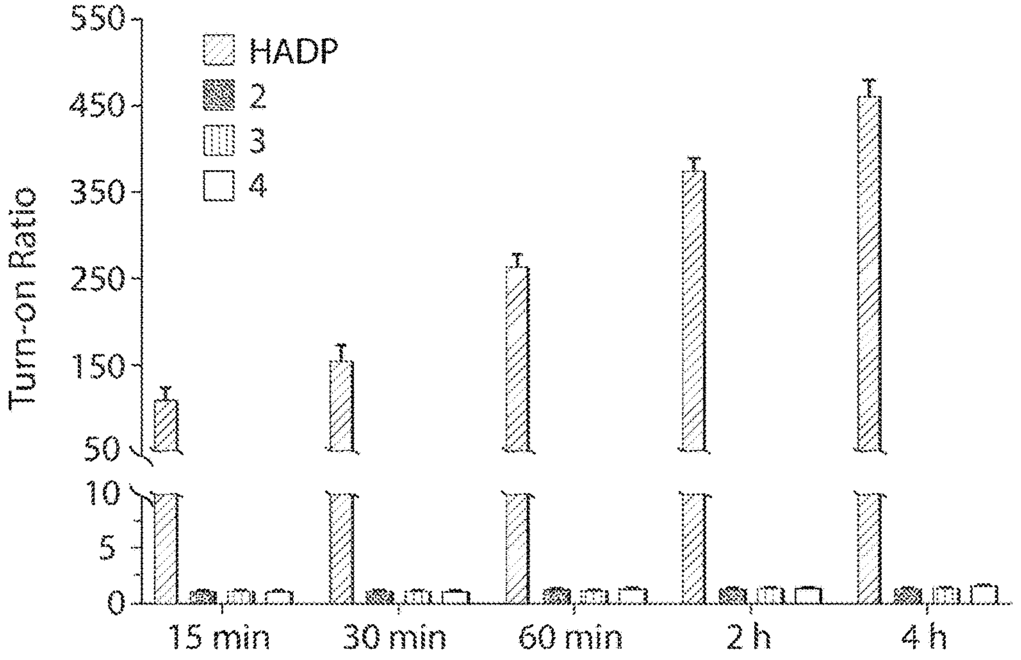
FIG. 4A shows fluorescence responses of probe HADP (also referred to as compound 1) and compounds 2-4 (each 5 μM) towards heparanase (1 g) in 40 mM NaOAc buffer (pH 5.0) over time at 37° C.

The response of compounds 2, 3 and 4 towards heparanase were examined. The results indicated that probes 2 and 4 could not be activated by heparanase, while compound 3 produced very slight fluorescence enhancement with long-time incubation. Compared with the structures of compound 2 and 3, one explanation is that the compound 3 bears an electron-withdrawing group at the ortho position of glyosidic bond. Based on this hypothesis, enhancement of the leaving ability of fluorophore (aglycone) was investigated instead of increasing the affinity to heparanase. Electron-withdrawing groups such as fluorine were introduced on the phenol ring of 4-methyl coumarin for increasing the leaving ability. Therefore, 6,8-difluoro-7-hydroxy-4-methylcoumarin (DiFMU) was selected as the fluorophore due to its high quantum yield and photostability to synthesize Compound 1 as shown in FIG. 1. The reactivity of Compound 1 towards heparanase was studied (FIG. 4A). A significant fluorescence enhancement was observed over the background, making it a heparanase activatable difluorocoumarin-based probe (HADP). Interestingly, compounds 2-4 barely show a fluorescence change under the same condition, demonstrating that the importance of the substituent effect.

Then, reaction conditions of Compound 1 (HADP) with heparanase were optimized, such as reaction buffer, pH. The reported working buffer for heparanase included 50 mM 2-(N-morpholino)ethanesulfonic acid (MES) buffer (pH 6.0) 29 and 40 mM sodium acetate (NaOAc) buffer (pH 5.0). Heparanase activity was tested in these listed buffer and 40 mM NaOAc (pH 6.0) buffer. A contrasting behavior manifested: the reactivity of heparanase at pH 5.0 in NaOAc buffer was higher than that at pH 6.0, which was consistent with the previous findings that the optimal pH for heparanase activity was at 5.1. At the same pH value, the reactivity in NaOAc buffer exhibited a faster rate. Thus, chose 40 mM NaOAc (pH 5.0) was chosen as the working buffer for the following experiments.

Spectroscopic Properties of Compound 1 (HADP)

Figure 3A:
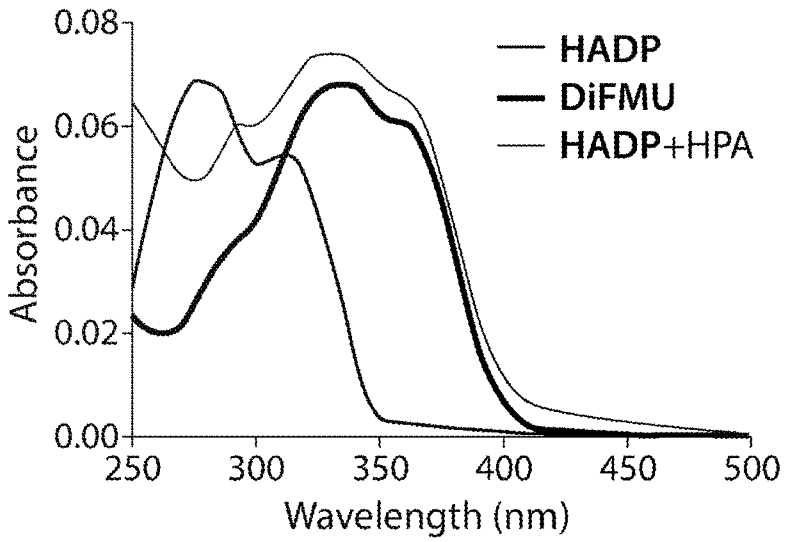
FIG. 3 shows the UV-vis absorption (FIG. 3A) and fluorescence (λex=365 nm) (FIG. 3B) spectra of probe HADP (5 M) before (blue line) and after (red line) incubation with heparanase (2 μg) in 40 mM NaOAc buffer (pH 5.0) for 2 h at 37° C.
FIG. 3C shows the fluorescent quantification of FIG. 3B.
FIG. 3D shows the relationship of fluorescence vs. time.
Figure 3B:
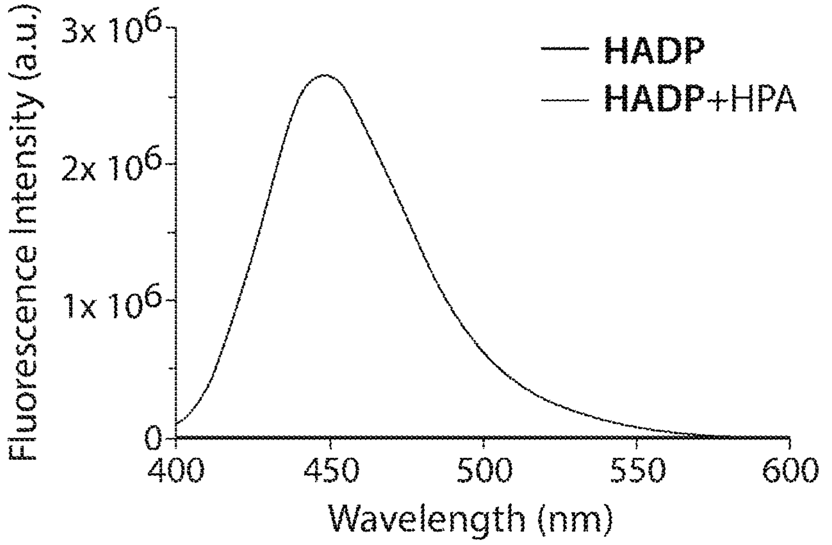
Figure 3C:
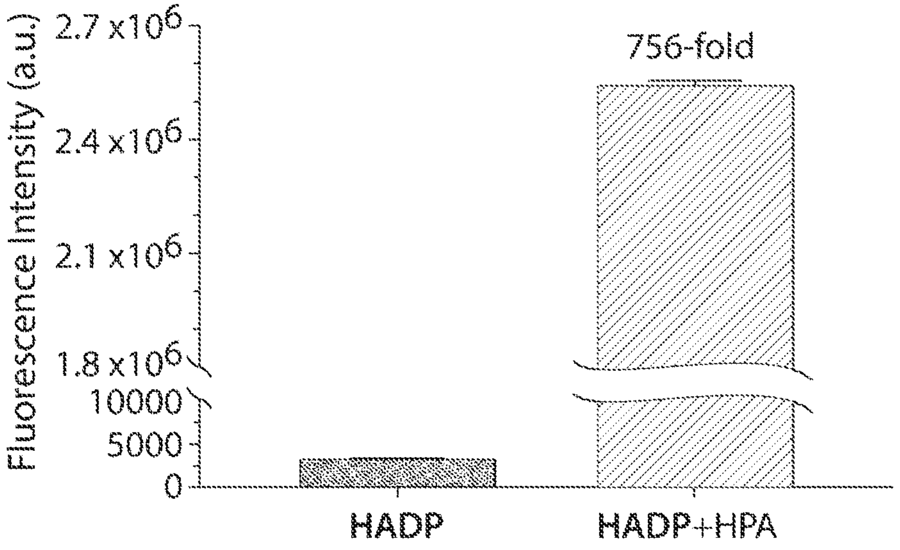
Figure 3D:
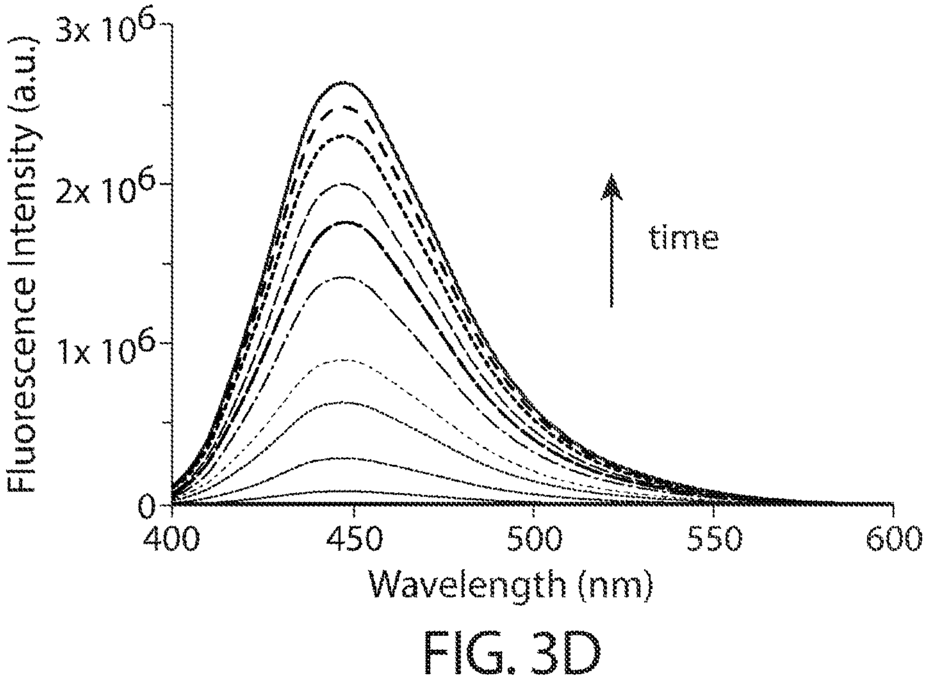

Compound 1 displayed the maximum absorption at 277 nm and 313 nm of the caged α-geminal difluoro coumarin (FIG. 3A). Upon treatment with HPSE, a remarkable bathochromic shift was observed with an absorption bump ranging from 320 nm to 365 nm, which is consistent with the absorption of uncaged difluorocoumarin in NaOAc buffer (pH 5.0). Compound 1 (HADP) itself is nonfluorescent (FIG. 3B). Upon addition of heparanase (2 μg, 0.01 μgμl-1), an extremely high fluorescence enhancement up to 756-fold turn-on ratio (the turn-on ratio is slightly various with different instruments) at 450 nm was detected (FIG. 3C) after 2 hours (to ensure the completion of reaction. In fact, based on kinetic studies, the enzymatic reaction was completed at 40 min after the addition of heparanase, indicating that 1 (HADP) can serve as an ultrasensitive probe for heparanase detection. This turn-on response can be attributed to the enzyme-triggered cleavage of glycosylic bond to liberate the free hydroxyl group of coumarin as a strong electron donor in the D-π-A system, thereby recovering ICT process and lighting up fluorescence. Then the time dependence of fluorescence spectra of HADP (5 μM) with heparanase (1 μg) were investigated (FIG. 3D). The fluorescence increased dramatically in the initial stage and reached a plateau at 2.5 h. The reaction rate was slower compared to that with 2 μg heparanase (FIG. 3A). More importantly, the fluorescence intensity exhibited a good linearity to time in the initial 15 minutes, facilitating the determination of enzyme kinetics combined the standard curve of DiFMU, which is not achievable by other heparanase assays.

Validation of Activation by Chromatography

Figure 5A:
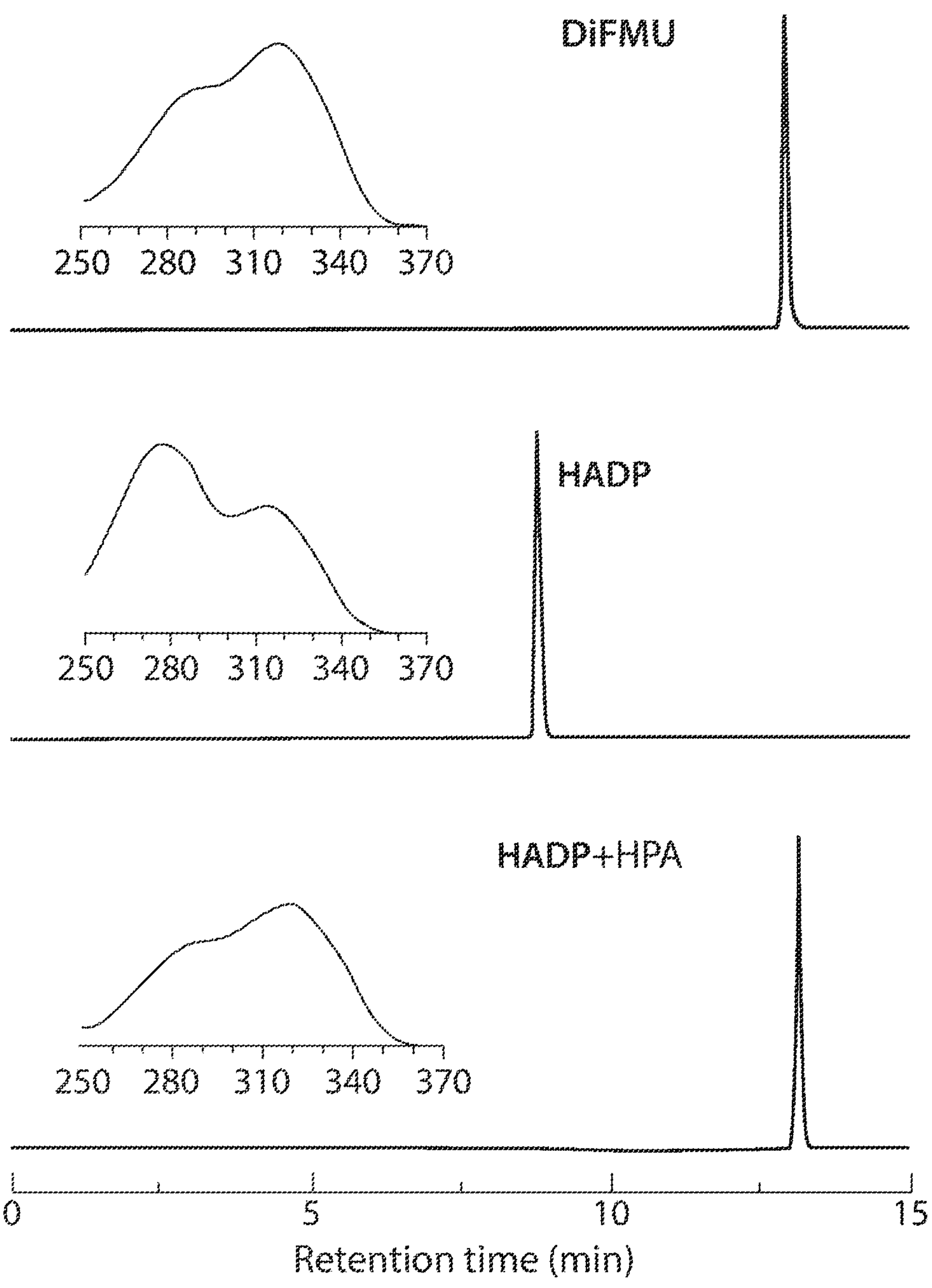
FIG. 5A shows HPLC traces of DiFMU (blue line), HADP (black line) and HADP with heparanase (red line). Inset: absorption of each peak.
Figure 5B:
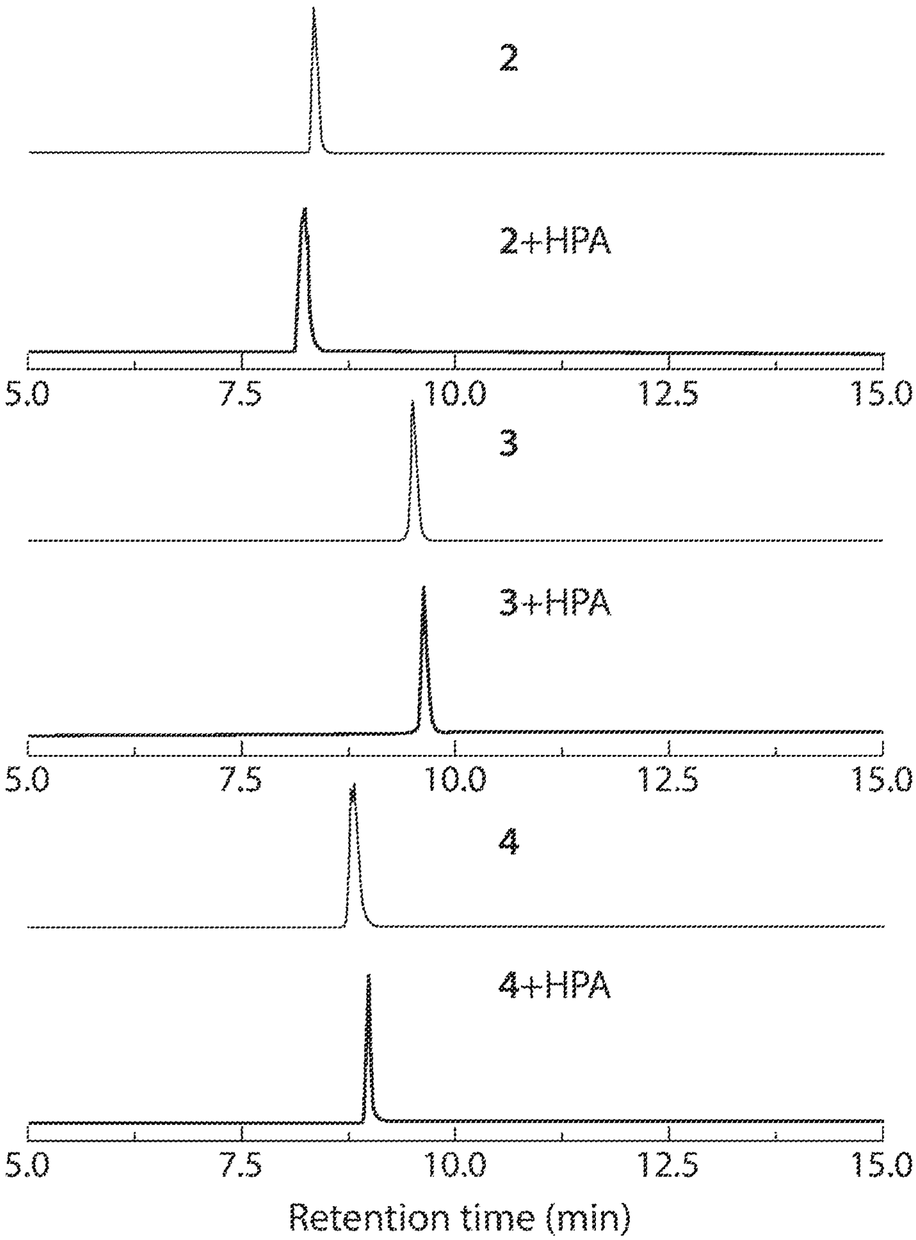
FIG. 5B shows HPLC traces of compounds 2-4 without (black line)/with (red line) heparanase.

To verify this mechanism, HPLC equipped with a DAD detector and ESI mass spectrometry was utilized to monitor this enzymatic hydrolysis process and analyze the hydrolytic product (FIGS. 5A-B). A clean conversion was observed and produced a new peak at 13.1 min in the HPLC trace after incubation of 5 μM probe with heparanase (1 μg) for 4 hours (red line), which was consistent with retention time of DiFMU (black line). Moreover, the absorption of this new peak is as same as that of DiFMU. Furthermore, this new peak was collected and subjected to high-resolution electrospray ionization (HR-ESI) mass analysis. Two signals at m/z 213.0359 and 235.0181 were observed for the protonated and sodiated adducts, respectively (Theoretical [M+H]+=213.0358, [M+Na]+=235.01777). These results substantiated the liberation of difluorocoumarin upon treatment with heparanase, leading to the fluorescent enhancement. Compared with Compound 1 (HADP), HPLC traces of compounds 2, 3 and 4 with heparanase did not display any new peaks, verifying compounds 2, 3 and 4 could not be cleaved by heparanase.

Computational Validation of Activation

Figure 6A:
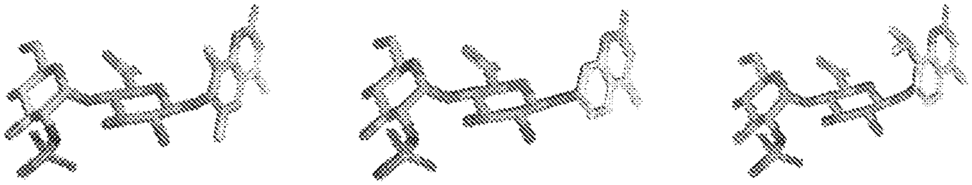
FIG. 6A shows 3D models of compounds 1-3.
Figure 6B:
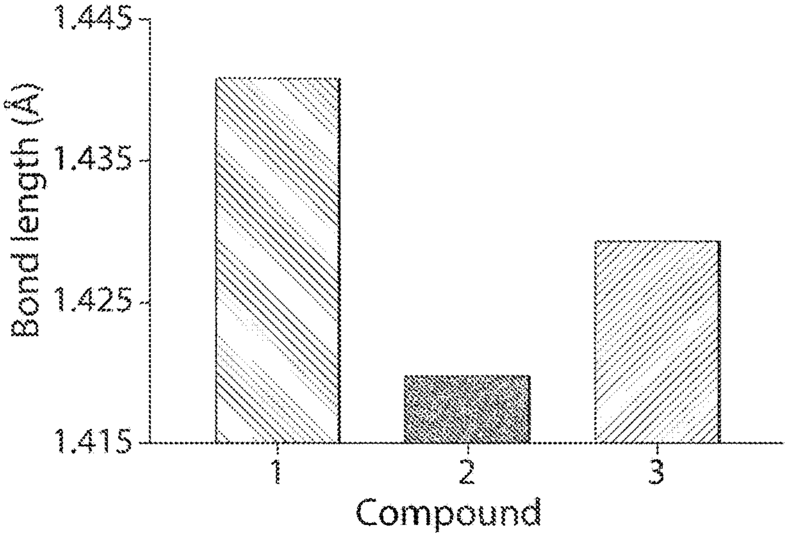
FIG. 6B shows the glycosidic bond length of compounds 1-3.
Figure 6C:
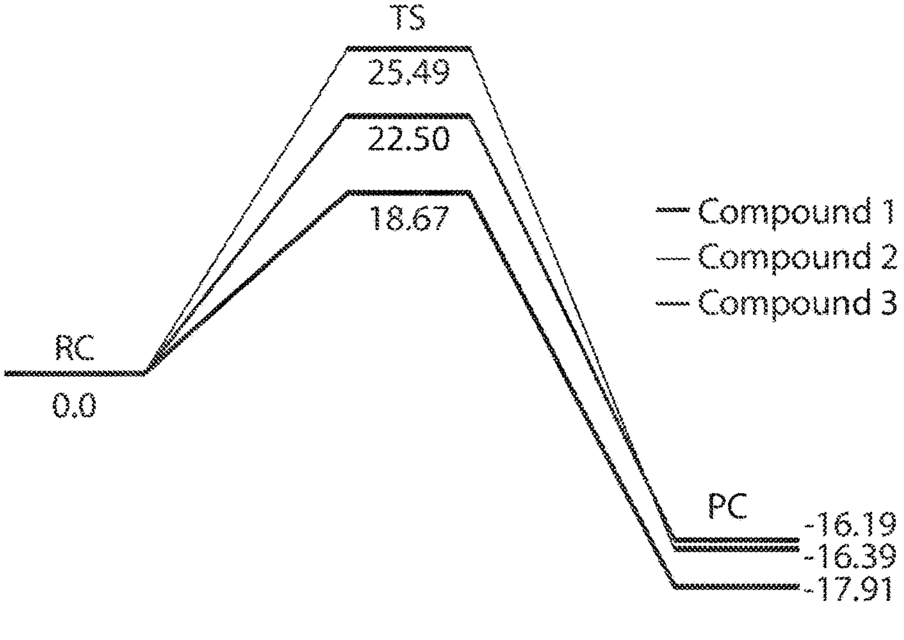
FIG. 6C shows the relative free energy (in Kcal/mol) profile of reaction pathways for the compounds 1-3.

To gain an insight into the reactivities of these compounds bearing various substituents with heparanase, (density functional theory) DFT was performed with GAUSSIAN 09 program using 6−31+G(d) basis set (FIG. 6A). The length of glycosidic bond in Compound 1 (HADP) is slightly longer than that of compound 2 or 3, indicating the glycosidic bond in Compound 1 was more prone to cleavage (FIG. 6B). Also, it was found that the energy barrier for Compound 1 (HADP) (18.67 kcal/mol) in transition state is much lower than that compound 2 or 3 due to the presence of two electron-withdrawing fluorines at the ortho position of phenoxyl group, leading to an expedited glycosidic cleavage (FIG. 6C). These results are consistent with experimental findings.

Evaluation of Selectivity

Figure 4B:
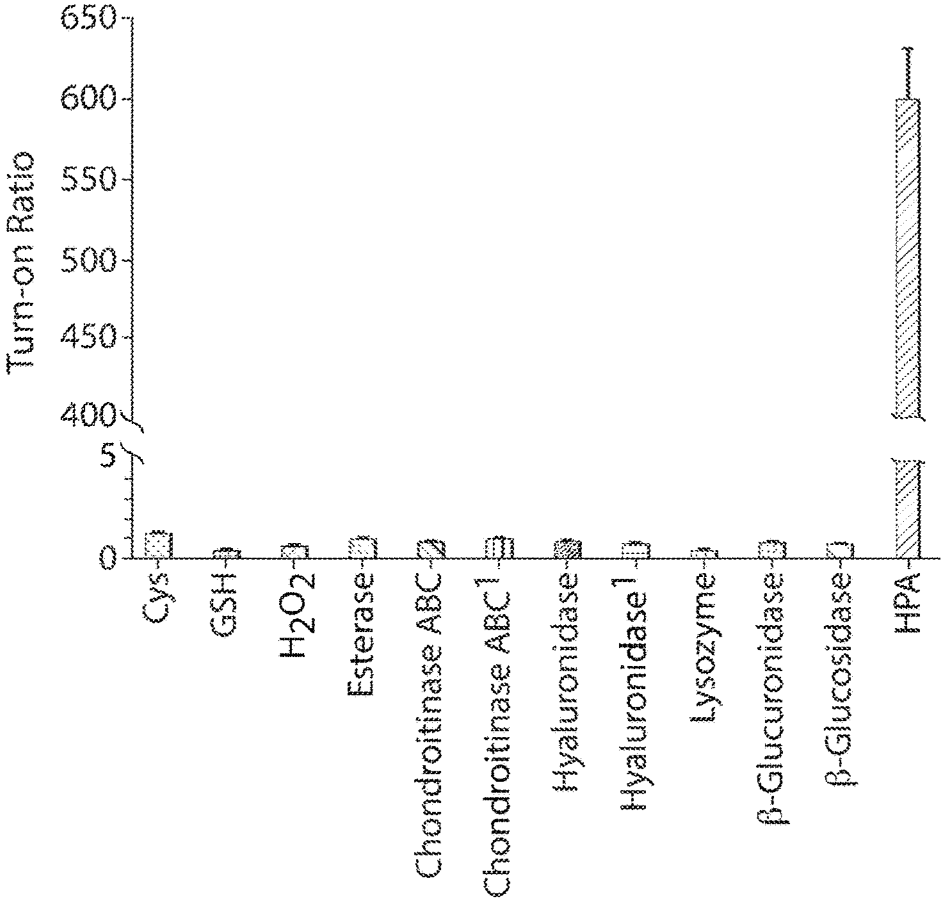
FIG. 4B shows fluorescence responses of probe HADP to Cys (5 mM), GSH (5 mM), $H_2O_2$ (100 μM), Esterase, Chondroitinase ABC, Hyaluronidase, Lysozyme, β-Glucuronidase, β-Glucosidase (5 μg each) and HPA (2 μg) for 4 h. 50 μg enzyme was used. λex/em=365 nm/455 nm.

The selectivity of Compound 1 (HADP) was evaluated toward heparanase against a series of possible interfering biological molecules and enzymes at relatively high levels (FIG. 4B). Heparanase exhibited the largest "off-on" response, while no fluorescence increase was observed upon addition of other molecules and enzymes even at super-physiological levels. For instance, Compound 1 (HADP) was treated with 100 μM H2O2, 5 mM glutathione (GSH) and cysteine (Cys), commonly co-existing biological oxidizing and reducing species in cells. No fluorescence change was observed. Hyaluronidase and chondroitinase, which are polysaccharide lyases that catalyze the cleavage of glyosidic bond of N-acetyl-D-glucosamine and D-glucuronic acid in hyaluronic acid and D-hexosaminyl and D-glucuronic acid in chondroitin respectively, did not afford obvious fluorescence change. Likewise, β-glucuronidase did not trigger fluorescence response either since Compound 1 (HADP) possesses a glycosyl substituent on 4-position of glucuronic residue. Taken together, Compound 1 (HADP) manifested excellent selectivity for heparanase over other competitive analytes.

Evaluation of pH Effect on Activation

The fluorescent intensity was significantly affected by the pH. So, pH profiles of the fluorophore DiFMU and Compound 1 (HADP) were evaluated. There was no remarkable fluorescence change at 455 nm for Compound 1 (HADP) in the pH range from 1 to 13 upon excitation. However, the hydrolytic product of HADP demonstrated a dependent manner over pH, and the pKa was determined to be ca. 4.7, which is consistent with previous reports. The introduction of the fluorine substituents at the ortho position significantly reduced the pKa of the fluorophore molecule, rendering the proportion of phenoxy ion enriched at the optimal pH of heparanse activity without basification, rendering the assay simple and rapid for hepranase detection. In contrast, the pKa of 4-methylumbelliferone is ca. 7.8. Therefore, Compound 2 could not serve as an ideal probe for heparanase because the fluorescence intensity of released 4-methylumbelliferone substantially decreased at the optimal pH of heparanse activity, far below its pKa even if it can be activated by heparanase. Moreover, the introduction of the fluorine substituents increased the quantum yield and improved the photostability, enabling highly sensitive detection for heparanase.

Kinetics and Detection Limit of Heparanase by Compound 1 (HADP)

To determine the detection limit of Compound 1 (HADP) probe for heparanse, concentration-dependent studies with various concentrations of heparanse over time were performed with 5 μM 1 (HADP). The concentration increases of heparanse led to higher fluorescent intensities at the same time point due to the expedited cleavage of glyosidic bond, releasing more fluorophores. A good linear relationship was obtained in the heparanse concentration range of 0-0.01 μgμl-1 with an equation of F455 nm=650443[HPA]+12.03 ($R^2$=0.9968). Based on 3σ/s method, the limit of detection (LOD) of Compound 1 for heparanse was calculated to be 0.35 ng/mL (67 pM), indicating the ultra-sensitivity of Compound 1 (HADP) to detect heparanase activity. The kinetic parameters for the enzymatic cleavage of Compound 1 (HADP) were determined via time-dependent fluorescence intensity in the presence of heparanase and probe 1 (HADP) at different concentration. Thus, the Michaelis constant (Km), the catalytic efficiency constant (kcat/Km) and the turnover number (kcat) were calculated as 8.3 μM, 0.29 μM-1 min-1 and 2.4 min-1, respectively. Compared with the Km of fondaparinux, 46 μM, a pentasaccharide substrate for heparanase, Compound 1 (HADP) exhibited a significantly high affinity to heparanase.

Compound 1-Assisted High-Throughput Screening

Figure 7:
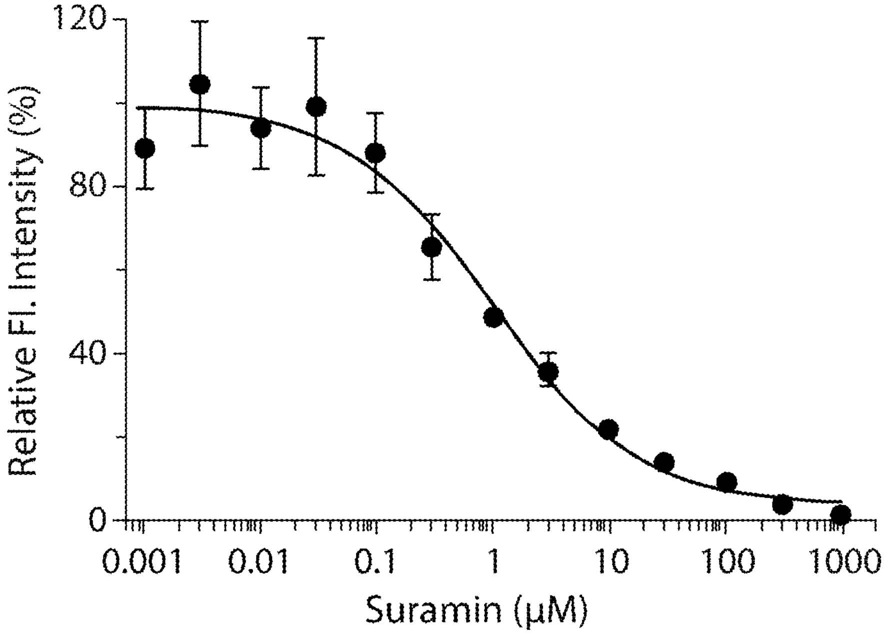
FIG. 7 shows the inhibition assay results of heparanase with suramin in 40 mM NaOAc buffer (pH 5.0) for 2 h at 37° C.
Figure 8A:
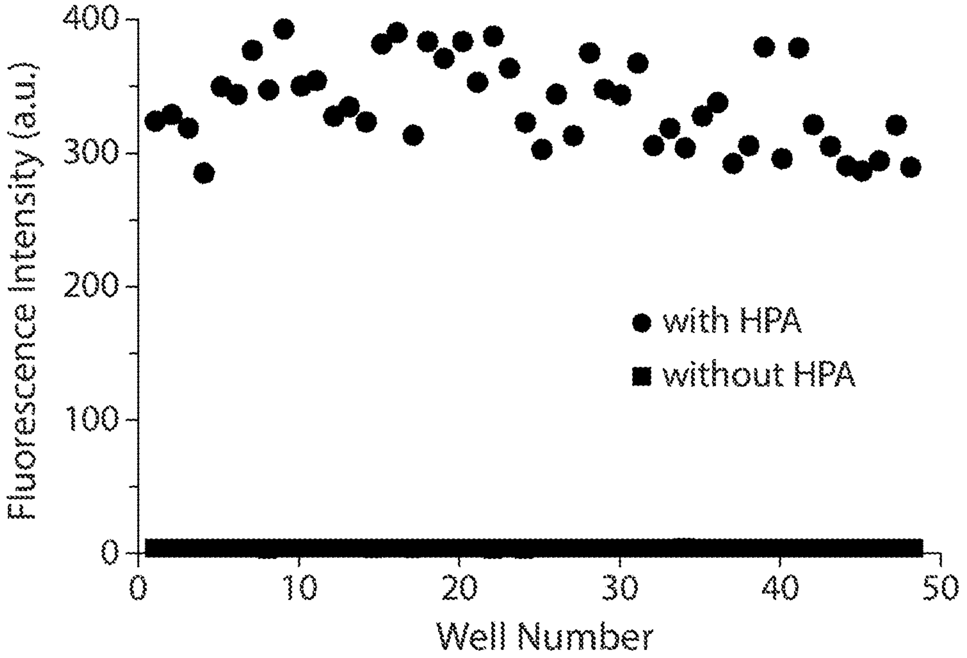
FIG. 8A shows the Z'-factor determination for heparanase inhibitor screening.
Figure 8B:
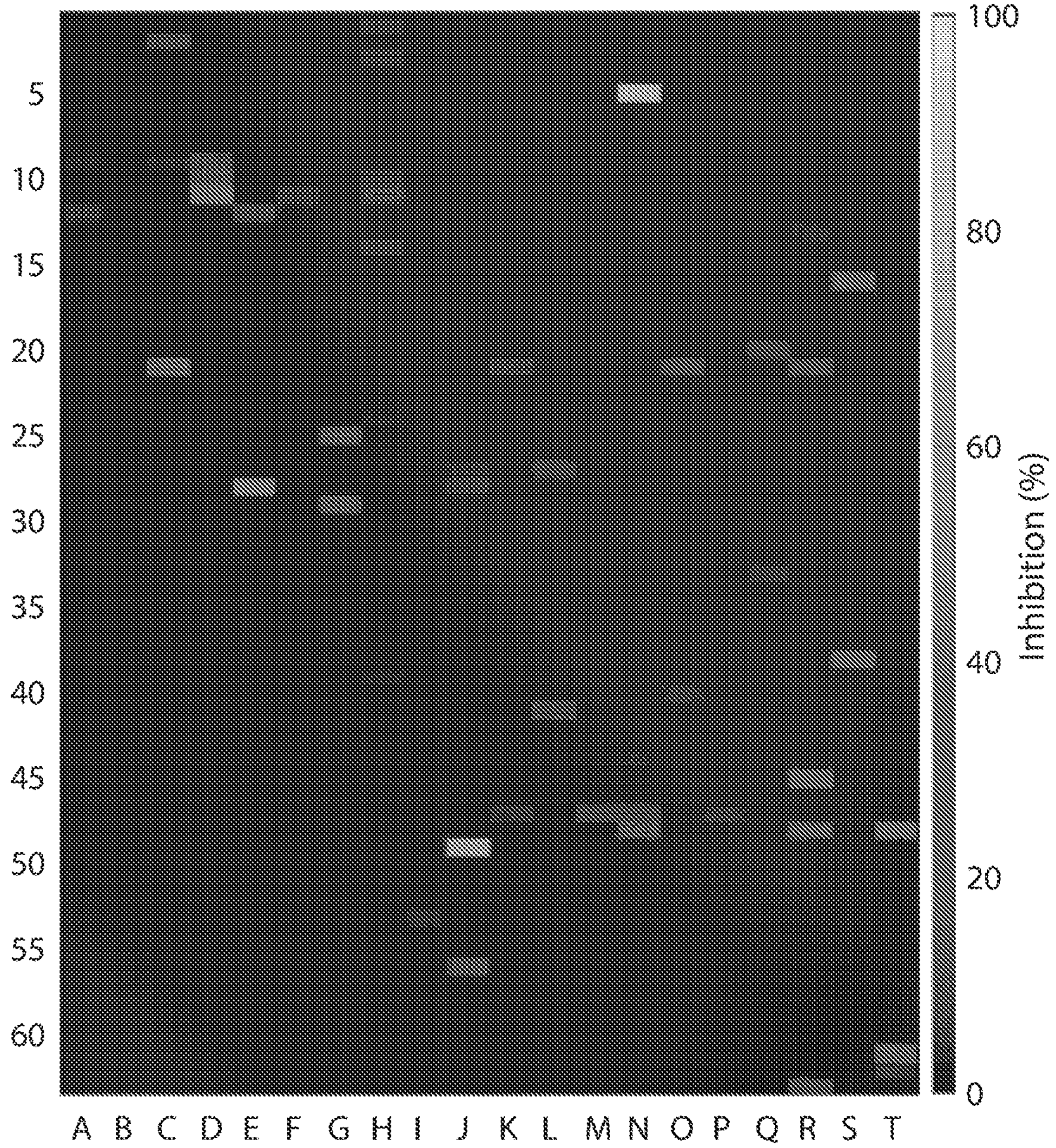
FIG. 8B shows the results of fluorescence-based HTS for heparanase inhibitor screening.
Figure 8C:
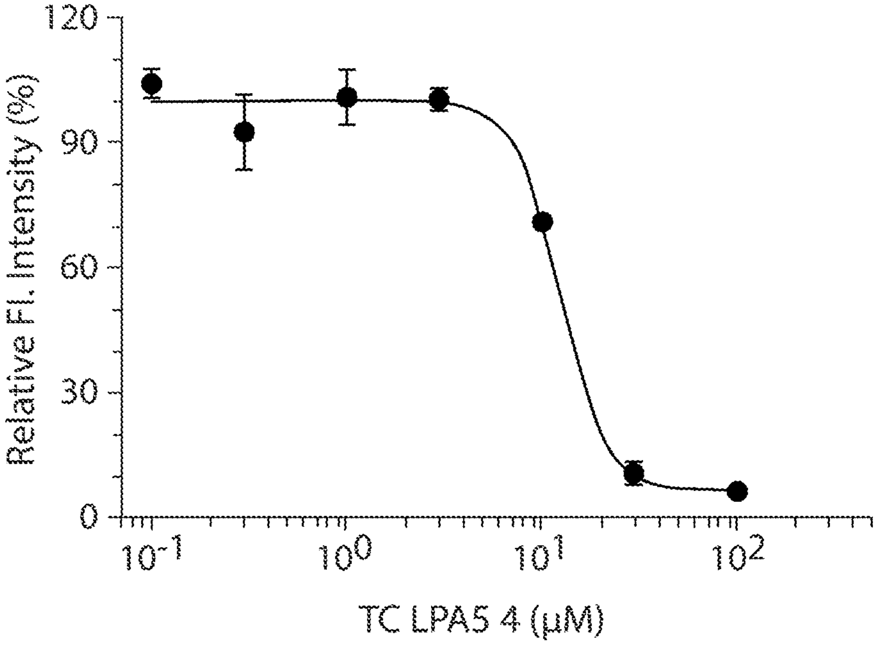
FIG. 8C shows the $IC_{50}$ plot of TC LPA5 4.

First, a known heparanase inhibitor, suramin, was tested to examine the screening efficacy using Compound 1. Heparanase (0.025 μg) was incubated for 60 min with suramin at various concentrations ranging from 1 nM to 1 mM in 384-well plate. Then the probe (5 μM) was added to the mixture of heparanase and inhibitor for an additional 4 hours. The fluorescence was measured and plotted. The $IC_{50}$ value of suramin was calculated to be 1.0 μM (FIG. 7, which was is in good agreement with that determined by a commercial assay. Next, the performance of Compound 1 was evaluated in a high-throughput throughput assay. First, the quality of this assay was evaluated with a Z'-factor of approximately 0.7, indicating this assay is considered as an excellent format (FIG. 8A). Subsequently, a commercial library containing 1280 compounds in a 384-well format was screened against heparanase, which identified several hits (FIG. 8B). Further validation confirmed that one compound exhibited inhibitory activity on heparanase with $IC_{50}$ values of 12 μM (FIG. 8C). These results unambiguously demonstrated that Compound 1 was capable of screening inhibitors for heparanase.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Where ranges are given herein, embodiments are provided in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, embodiments that relate analogously to any intervening value or range defined by any two values in the series are provided, and that the lowest value may be taken as a minimum and the greatest value may be taken as a maximum. Where a phrase such as "at least", "up to", "no more than", or similar phrases, precedes a series of numbers herein, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated where applicable. A reasonable lower or upper limit may be selected or determined by one of ordinary skill in the art based, e.g., on factors such as convenience, cost, time, effort, availability (e.g., of samples, agents, or reagents), statistical considerations, etc. In some embodiments an upper or lower limit differs by a factor of 2, 3, 5, or 10, from a particular value. Numerical values, as used herein, include values expressed as percentages. For each embodiment in which a numerical value is prefaced by "about" or "approximately", embodiments in which the exact value is recited are provided. For each embodiment in which a numerical value is not prefaced by "about" or "approximately", embodiments in which the value is prefaced by "about" or "approximately" are provided. "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. Individuals or entities performing different step(s) may or may not interact.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The disclosure also comprises the following clauses:

1. A compound of Formula (I):

(I)

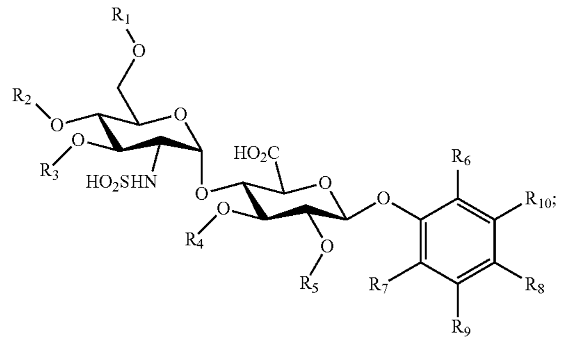

or a salt thereof;

wherein each of $R_1$, $R_2$, $R_3$, $R_4$, and $R_5$ is independently H, $-SO_3H$, or $-PO_3H$;

each of $R_6$ and $R_7$ is independently H, fluoro, chloro, bromo, nitro, cyano, trifluoromethyl, $-CO_2H$, $-OSO_3H$, or $-SO_3H$;

$R_8$ is optionally substituted alkyl, optionally substituted alkenyl, or optionally substituted alkynyl;

each $R_9$ and $R_{10}$ is independently H or alkyl;

or $R_8$ and $R_9$, and the carbon atoms to which they are attached form an optionally substituted heterocyclic or heteroaryl moiety;

or $R_8$ and $R_{10}$, and the carbon atoms to which they are attached form an optionally substituted heterocyclic or heteroaryl moiety;

provided that the compound is not:

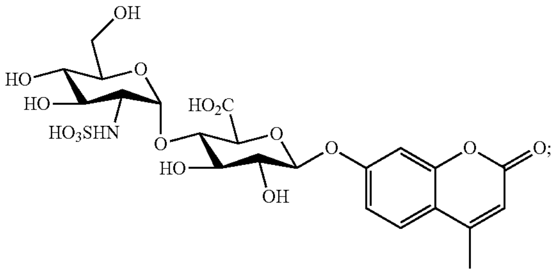

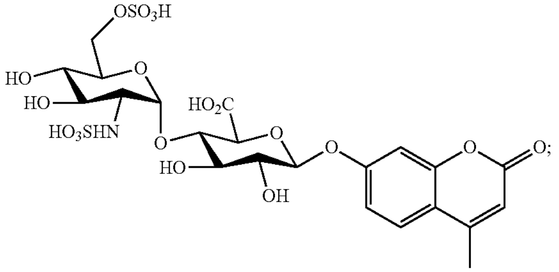

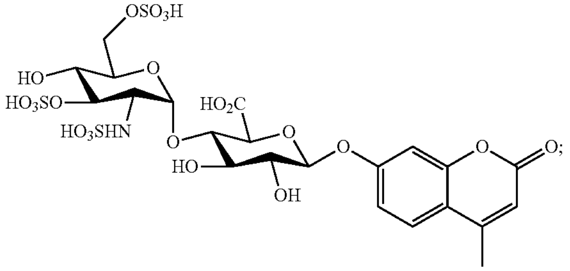

or a salt thereof.

2. The compound of clause 1, or a salt thereof, according to Formula (II):

(II)

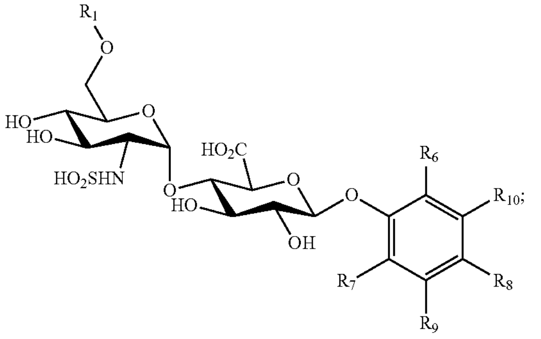

or a salt thereof.

3. The compound of clause 1 or 2, or a salt thereof, wherein $R_1$ is H or —$SO_3H$.

4. The compound of clause 3, or a salt thereof, wherein $R_6$ and $R_7$ are each independently H, fluoro, chloro, or bromo.

5. The compound of clause 3, or a salt thereof, wherein $R_6$ and $R_7$ are each independently H or fluoro.

6. The compound of clause 3, or a salt thereof, wherein $R_6$ is fluoro.

7. The compound of clause 3, or a salt thereof, wherein $R_7$ is fluoro.

8. The compound of clause 3, or a salt thereof, wherein $R_6$ and $R_7$ are fluoro.

9. The compound of any one of clauses 1-8, or a salt thereof, wherein

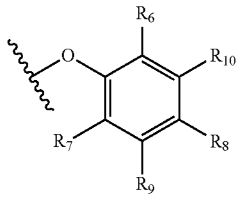

is

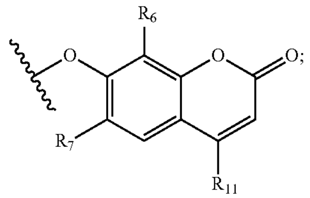

wherein $R_{11}$ is H or alkyl.

10. The compound of clause 9, wherein $R_{11}$ is methyl.

11. The compound of any one of clauses 1-8, or a salt thereof, wherein

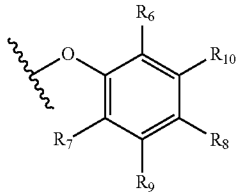

is

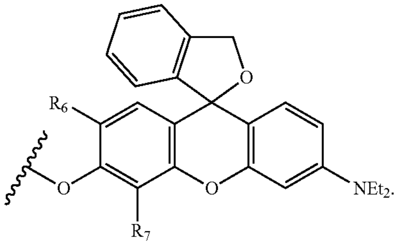

12. The compound of any one of clauses 1-8, or a salt thereof, wherein

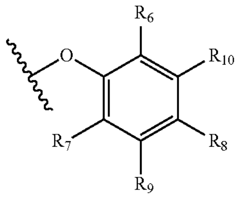

is

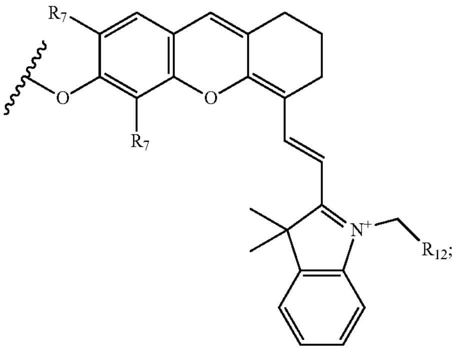

wherein $R_{12}$ is H, alkyl, or alkyl substituted with —$SO_3H$.

13. The compound of clause 12, or a salt thereof, wherein $R_{12}$ is H, ethyl, or —$CH_2CH_2SO_3H$.

14. The compound of any one of clauses 1-8, or a salt thereof, wherein

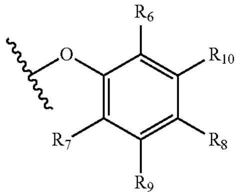

is

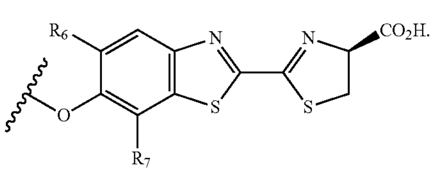

15. The compound of any one of clauses 1-8, or a salt thereof, wherein $R_8$ is

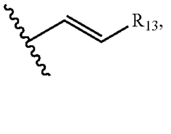

wherein $R_{13}$ is optionally substituted heterocyclyl.

16. The compound of clause 15, or a salt thereof, wherein $R_{13}$ is

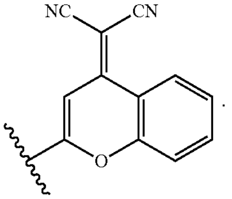 [SMILES: *C1=CC(=C(C#N)C#N)c2ccccc2O1]

17. The compound of clause 15, or a salt thereof, wherein $R_{13}$ is

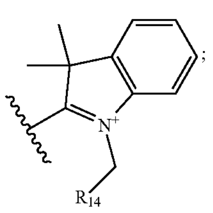

wherein $R_{14}$ is H, alkyl, or alkyl substituted with $SO_3H$.

18. The compound of clause 17, or a salt thereof, wherein $R_{14}$ is H, ethyl, or —$CH_2CH_2SO_3H$.

19. The compound of any one of clauses 1-8, or a salt thereof, wherein $R_8$ is

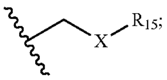

X is O or NH; and $R_{15}$ is optionally substituted aryl or heteroaryl.

20. The compound of clause 19, or a salt thereof, wherein $R_{15}$ is

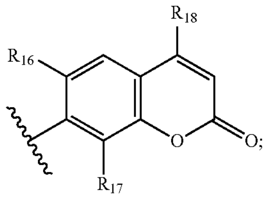

wherein each of $R_{16}$ and $R_{17}$ is independently H or haloalkyl; and $R_{18}$ is H or alkyl.

21. The compound of clause 20, or a salt thereof, wherein each of $R_{16}$ and $R_{17}$ is independently H, —$CHF_2$, or —$CH_2F$.

22. The compound of clause 20, or a salt thereof, wherein $R_{18}$ is methyl.

23. The compound of clause 20, or a salt thereof, wherein each of $R_{16}$ and $R_{17}$ is independently H, —$CHF_2$, or —$CH_2F$; and $R_{18}$ is methyl.

24. The compound of clause 19, or a salt thereof, wherein $R_{15}$ is

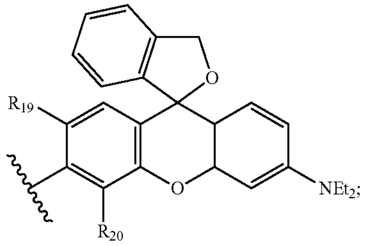

wherein each of $R_{19}$ and $R_{20}$ is independently H or haloalkyl.

25. The compound of clause 24, or a salt thereof, wherein each of $R_{19}$ and $R_{20}$ is independently H, —$CHF_2$, or —$CH_2F$.

26. The compound of clause 19, or a salt thereof, wherein $R_{15}$ is

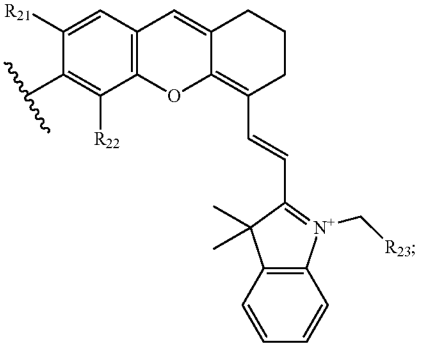

wherein each of $R_{21}$ and $R_{22}$ is independently H or haloalkyl; and $R_{23}$ is H, alkyl, or alkyl substituted with $SO_3H$.

27. The compound of clause 26, or a salt thereof, wherein each of $R_{21}$ and $R_{22}$ is independently H, —$CHF_2$, or —$CH_2F$.

28. The compound of clause 26, or a salt thereof, wherein $R_{23}$ is H, ethyl, or —$CH_2CH_2SO_3H$.

29. The compound of clause 26, or a salt thereof, wherein each of $R_{21}$ and $R_{22}$ is independently H, —$CHF_2$, or —$CH_2F$; and $R_{23}$ is H, ethyl, or —$CH_2CH_2SO_3H$.

30. The compound of clause 19, or a salt thereof, wherein $R_{15}$ is

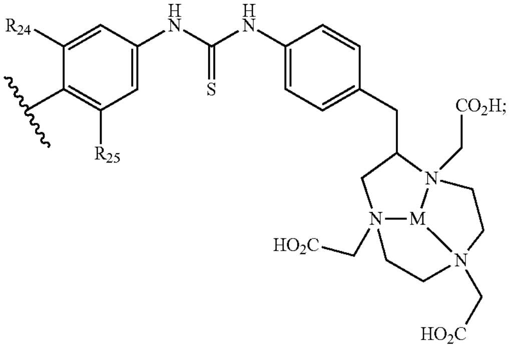

wherein each of $R_{24}$ and $R_{25}$ is independently H or haloalkyl; and

M is $Cu_{64}$ or $AlF_{18}$.

31. The compound of clause 30, or a salt thereof, wherein each of $R_{24}$ and $R_{25}$ is independently H, —$CHF_2$, or —$CH_2F$.

32. The compound of clause 19, or a salt thereof, wherein $R_{15}$ is

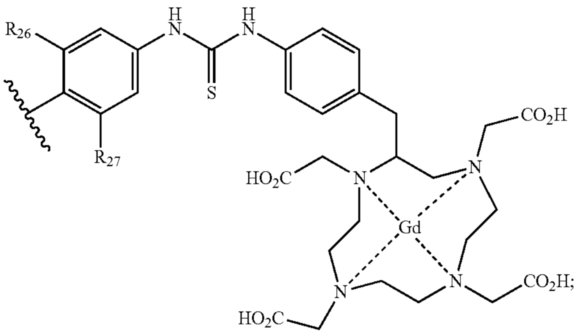

wherein each of $R_{26}$ and $R_{27}$ is independently H or haloalkyl.

33. The compound of clause 32, wherein each of $R_{26}$ and $R_{27}$ is independently H, —$CHF_2$, or —$CH_2F$.

34. The compound of any one of clauses 1-8, or a salt thereof, wherein $R_8$ is

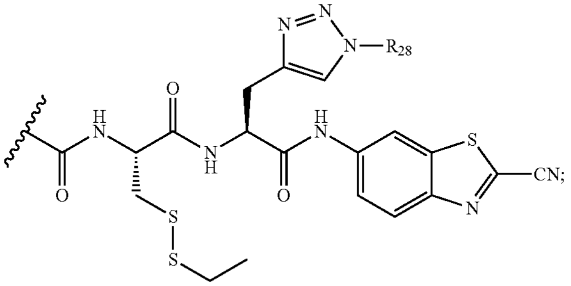

wherein $R_{28}$ is H, alkyl, or an imaging agent.

35. The compound of clause 34, or a salt thereof, wherein the imaging agent is:

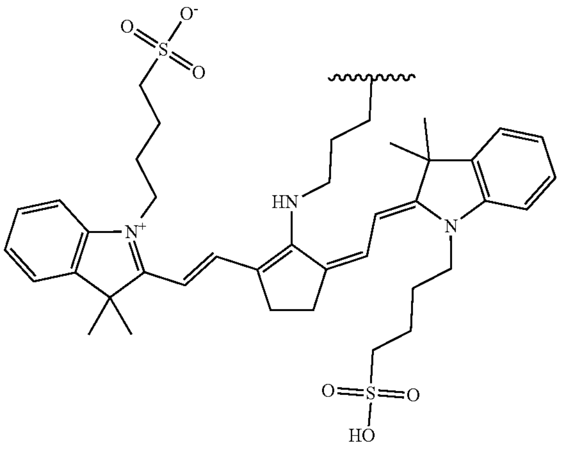
;
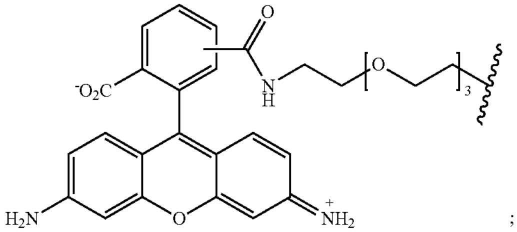
;
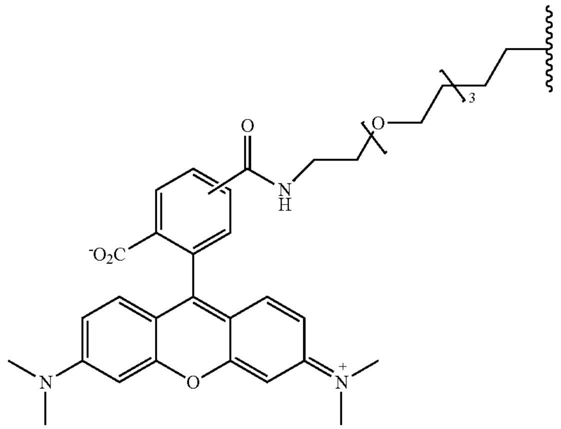
;
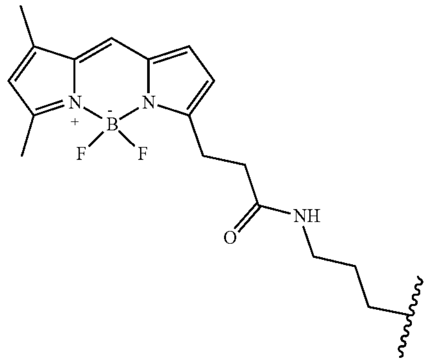
;
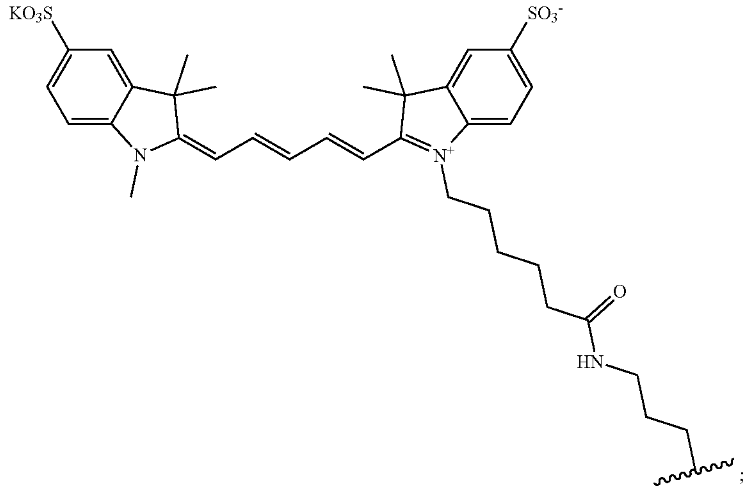
;

-continued
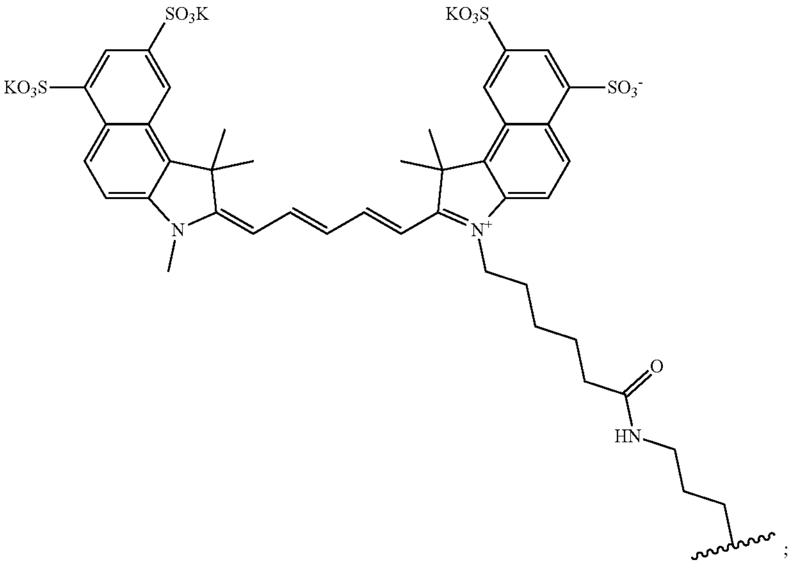
;
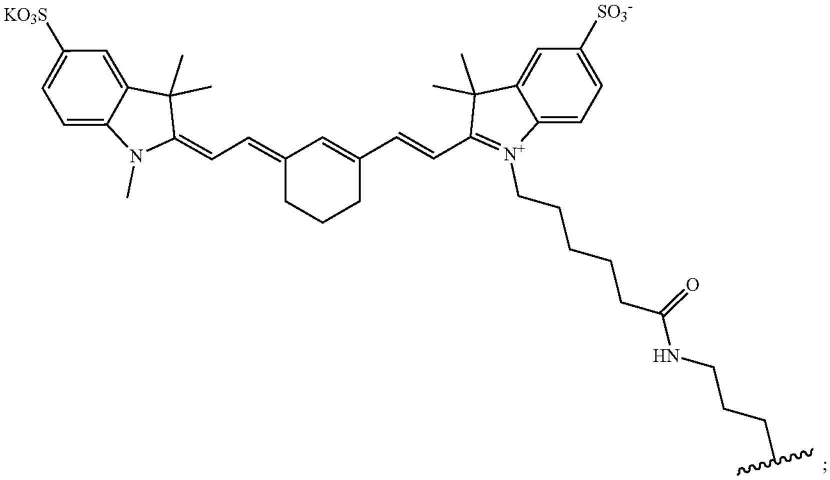
;
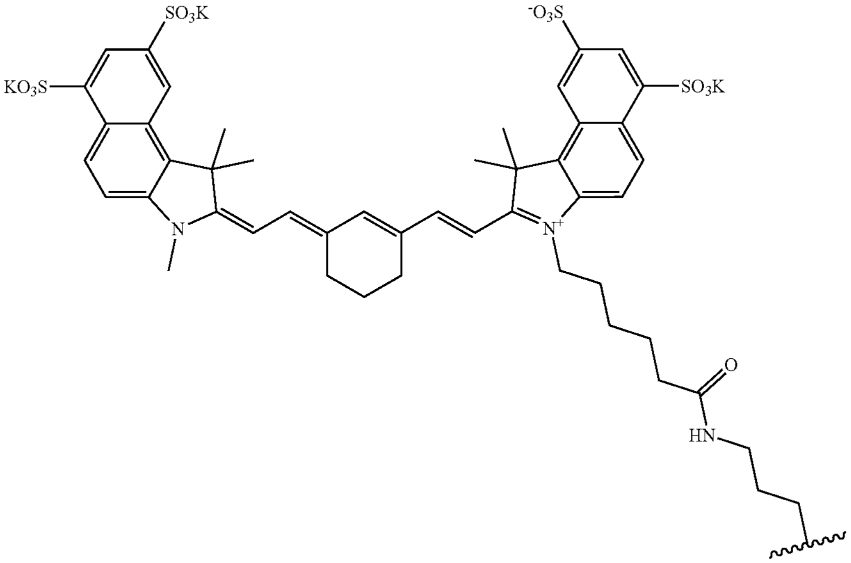
;

-continued
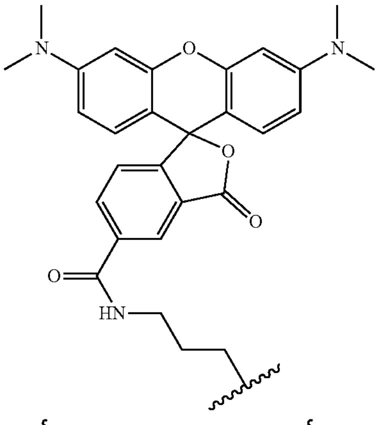
;
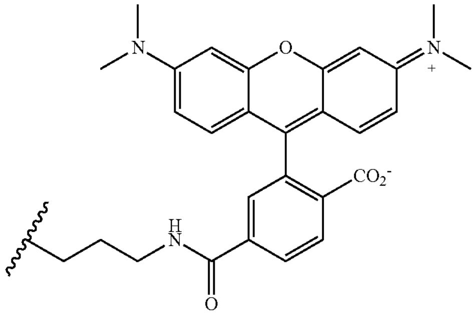
;
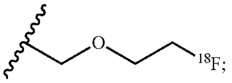
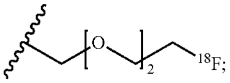
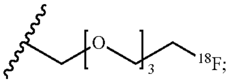
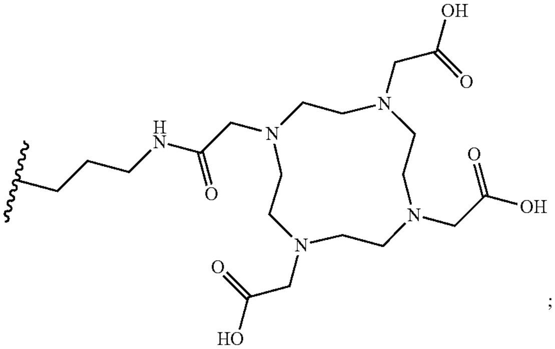
; or
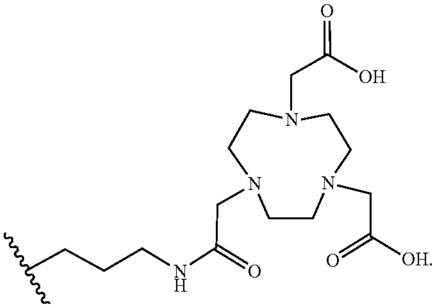
36. The compound of any one of clauses 1-35, or a salt thereof, wherein the compound is:
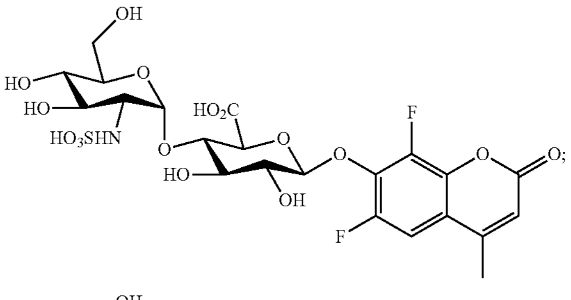
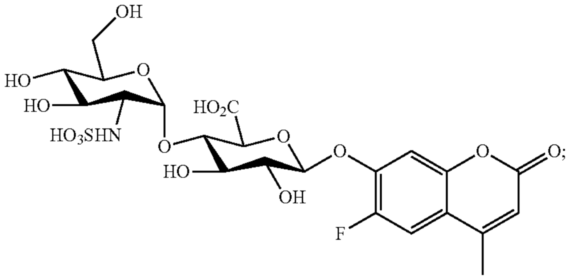
-continued
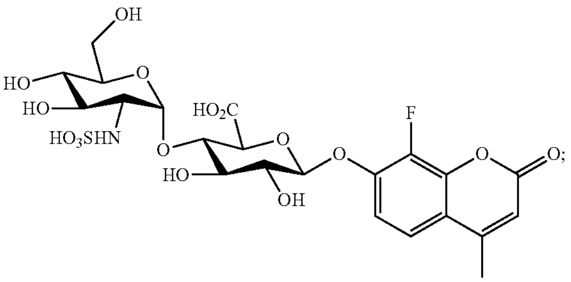
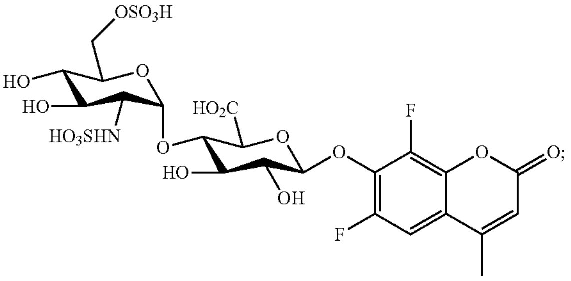

-continued

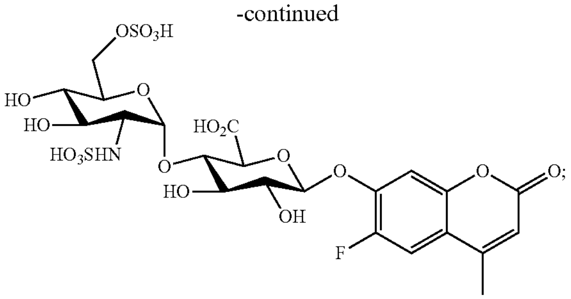

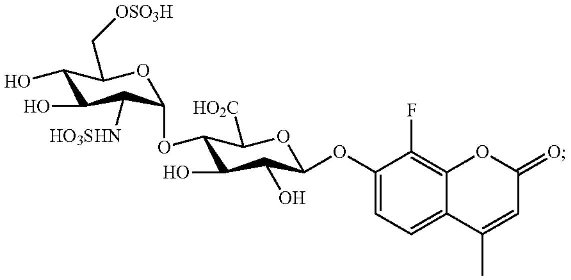

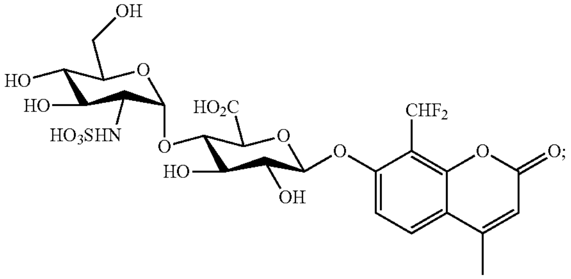

or a salt thereof.

37. A composition comprising a compound of any one of clauses 1-36, or a salt thereof.

38. A method for screening heparanase inhibitors, the method comprising:
  a. incubating heparanase with a heparanase inhibitor;
  b. adding a compound of any one of clauses 1-36, or a salt thereof; and
  c. measuring the fluorescence of the mixture from step b.

39. The method of clause 38, further comprising plotting the fluorescence from step c. of clause 38.

40. A method of performing positron emission tomography (PET) in a subject, the method comprising administering to the subject a compound of any one of clauses 1-36, or a salt thereof.

41. The method of clause 40, wherein the compound is the compound of clause 30 or 31, or a salt thereof.

42. A method of performing magnetic resonance imaging (MRI) in a subject, the method comprising administering to the subject a compound of any one of clauses 1-36, or a salt thereof.

43. The method of clause 42, wherein the compound is the compound of clause 32 or 33, or a salt thereof.

44. A kit comprising a compound of any one of clauses 1-36, or a salt thereof, and instructions for screening heparanase inhibitors.

45. A kit comprising a compound of any one of clauses 1-36, or a salt thereof, and instructions for administering a compound of any one of clauses 1-36, or a salt thereof, for performing positron emission tomography (PET) in a subject.

46. A kit comprising a compound of any one of clauses 1-36, or a salt thereof, and instructions for administering a compound of any one of clauses 1-36, or a salt thereof, for performing magnetic resonance imaging (MRI) in a subject.

What is claimed is:

1. A compound of Formula (I):

(I)

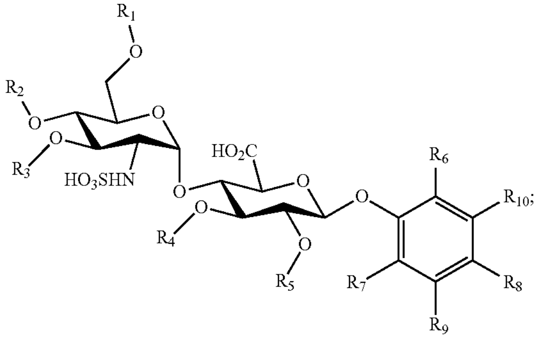

or a salt thereof;

wherein each of $R_1$, $R_2$, $R_3$, $R_4$, and $R_5$ is independently H, —$SO_3H$, or —$PO_3H$;

each of $R_6$ and $R_7$ is independently H, haloalkyl, fluoro, chloro, bromo, nitro, cyano, $CO_2H$, —$OSO_3H$, or —$SO_3H$, wherein at least one of $R_6$ and $R_7$ is haloalkyl, fluoro, chloro, bromo, nitro, cyano, $CO_2H$, —$OSO_3H$, or —$SO_3H$;

$R_8$ is optionally substituted alkyl, optionally substituted alkynyl, or

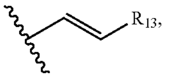

wherein $R_{13}$ is optionally substituted heterocyclyl; and each $R_9$ and $R_{10}$ is independently H, fluoro, chloro, bromo, nitro, cyano, trifluoromethyl, —$OSO_3H$, or —$SO_3H$;

or $R_8$ and $R_9$, and the carbon atoms to which they are attached form an optionally substituted heterocyclic or heteroaryl moiety;

or $R_8$ and $R_{10}$, and the carbon atoms to which they are attached form an optionally substituted heterocyclic or heteroaryl moiety;

provided that the compound is not:

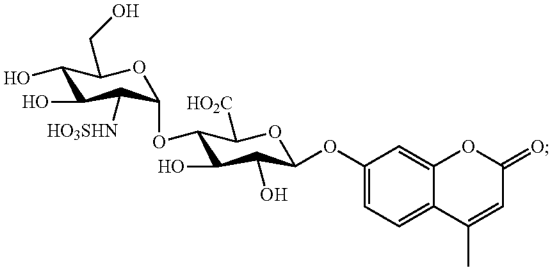

-continued

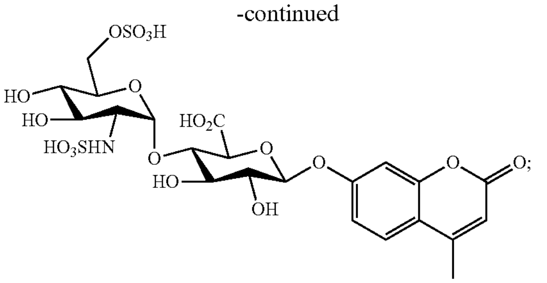

or

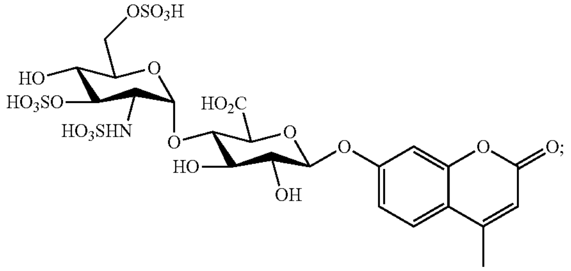

or a salt thereof.

2. The compound of claim 1, or a salt thereof, according to Formula (II):

(II)

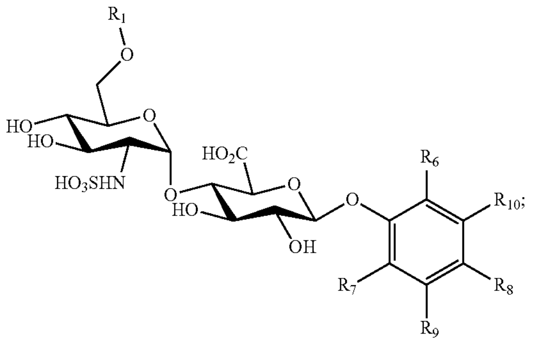

or a salt thereof.

3. The compound of claim 1, or a salt thereof, wherein $R_1$ is H or —$SO_3H$.

4. The compound of claim 3, or a salt thereof, wherein $R_6$ and $R_7$ are each independently H, fluoro, chloro, or bromo.

5. The compound of claim 3, or a salt thereof, wherein $R_6$ and $R_7$ are each independently H or fluoro.

6. The compound of claim 3, or a salt thereof, wherein $R_6$ and $R_7$ are fluoro.

7. The compound of claim 1, or a salt thereof, wherein

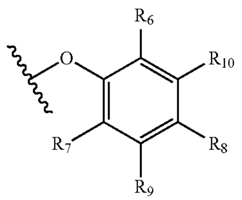

is:

(a)

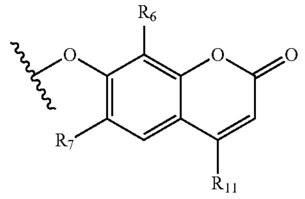

wherein $R_{11}$ is H or alkyl;

(b)

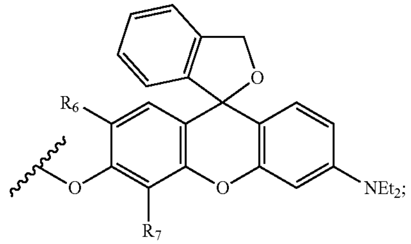

(c)

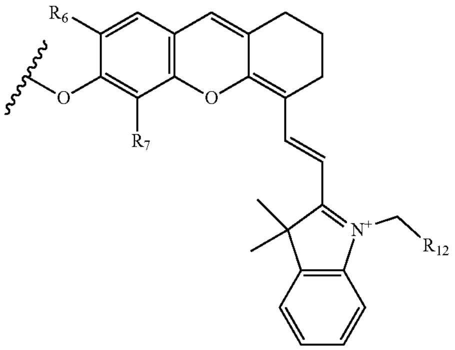

wherein $R_{12}$ is H, alkyl, or alkyl substituted with —$SO_3H$; or (d)

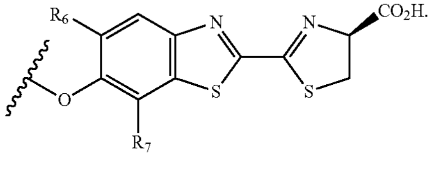

8. The compound of claim 1, or a salt thereof, wherein $R_{13}$ is:

(a)

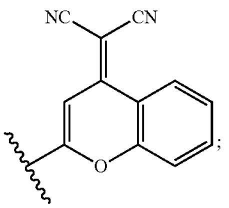 [SMILES: *C1=CC(=C(C#N)C#N)c2ccccc2O1]

or (b) $R_{13}$ is

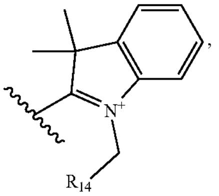

wherein $R_{14}$ is H, alkyl, or alkyl substituted with $SO_3H$.

9. The compound of claim 1, or a salt thereof, wherein $R_8$ is

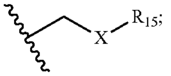

X is O or NH; and $R_{15}$ is optionally substituted aryl, heteroaryl, or —(C═O)N($R^{102}$)$_2$ wherein each $R^{102}$ is independently hydrogen or optionally substituted alkyl.

10. The compound of claim 9, or a salt thereof, wherein $R_{15}$ is:

(a)

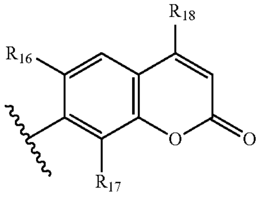

wherein each of $R_{16}$ and $R_{17}$ is independently H or haloalkyl; and $R_{18}$ is H or alkyl;

(b)

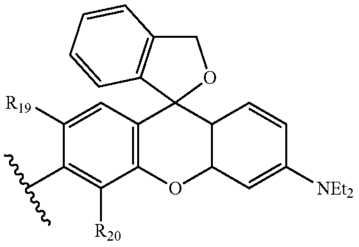

wherein each of $R_{19}$ and $R_{20}$ is independently H or haloalkyl;

(c)

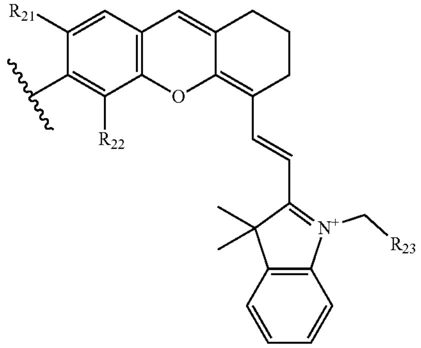

wherein each of $R_{21}$ and $R_{22}$ is independently H or haloalkyl; and $R_{23}$ is H, alkyl, or alkyl substituted with $SO_3H$;

(d)

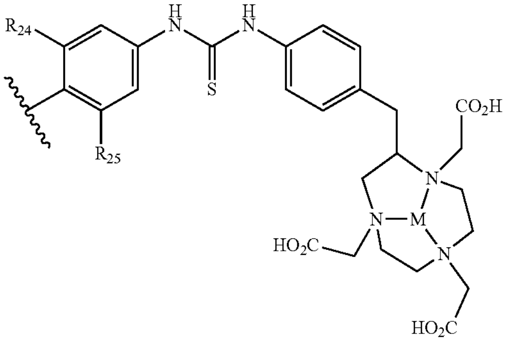

wherein each of $R_{24}$ and $R_{25}$ is independently H or haloalkyl; and M is $Cu_{64}$ or $AlF_{18}$;

(e)
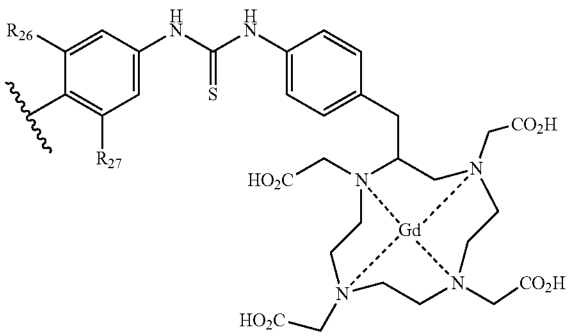
wherein each of $R_{26}$ and $R_{27}$ is independently H or haloalkyl; or
(f)
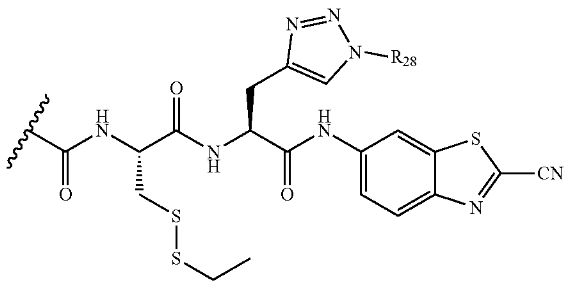
wherein $R_{28}$ is H, alkyl, or an imaging agent.
11. The compound of claim 10, or a salt thereof, wherein the imaging agent is:
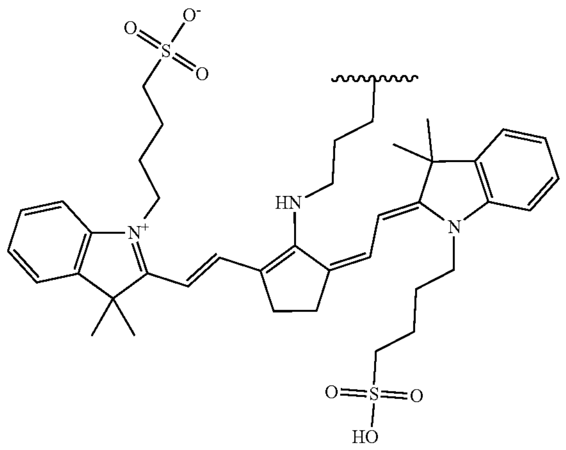
;
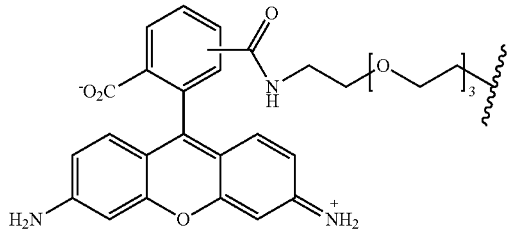
;
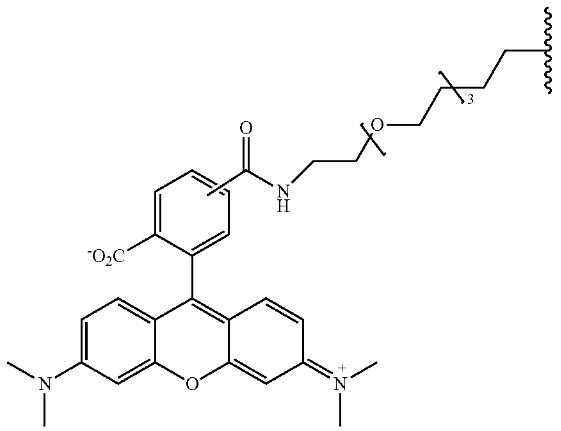
;
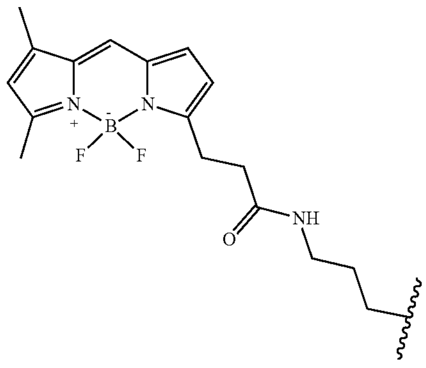
;

-continued
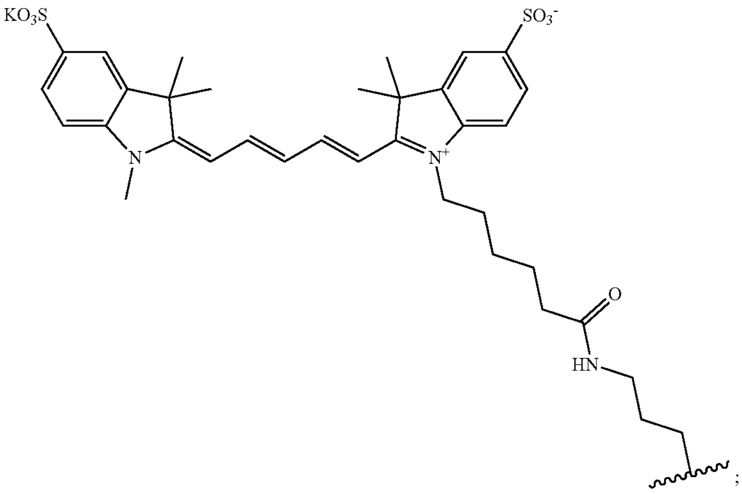
;
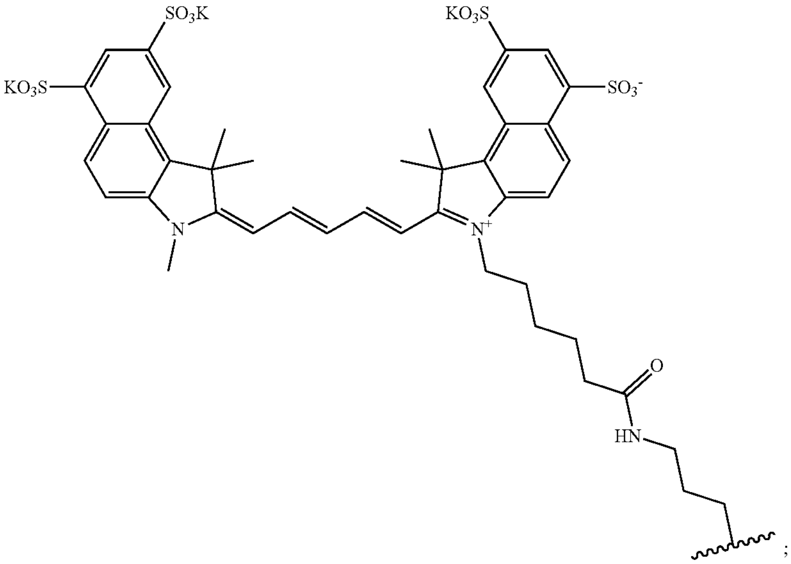
;
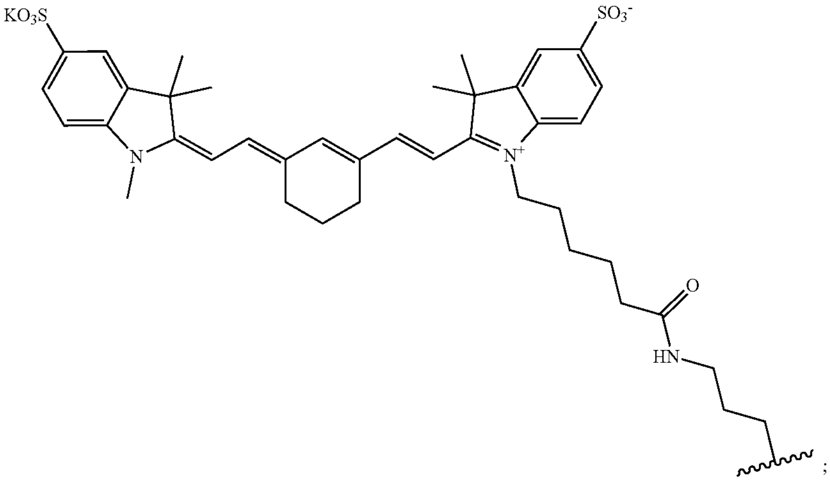
;

-continued
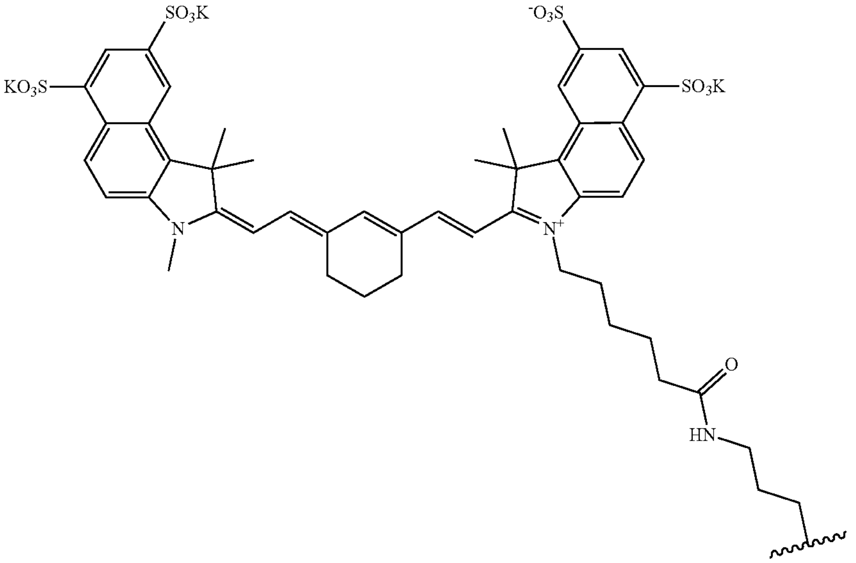
;
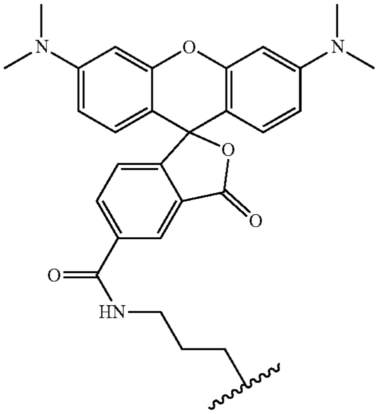
;
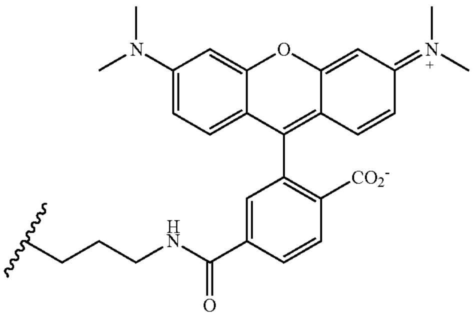
;
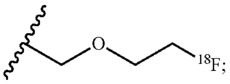
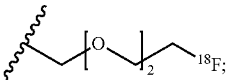
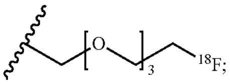
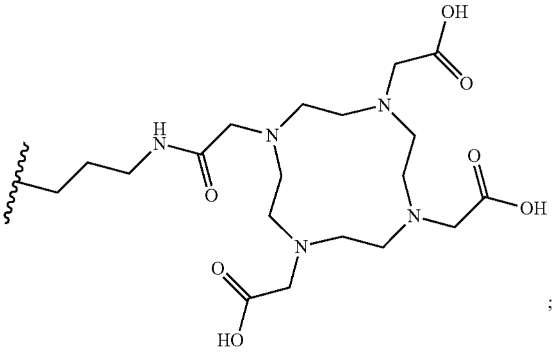
; or
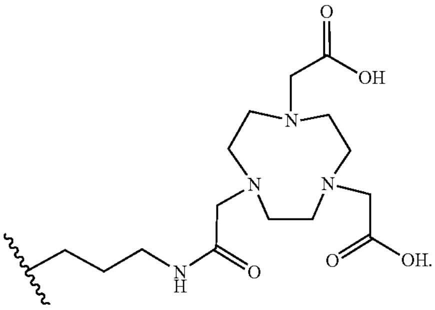

12. The compound of claim 1, or a salt thereof, wherein the compound is:

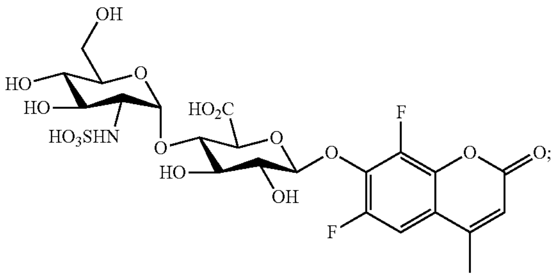

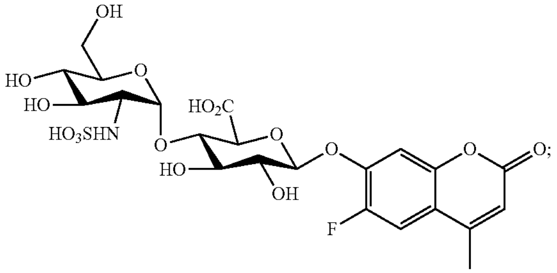

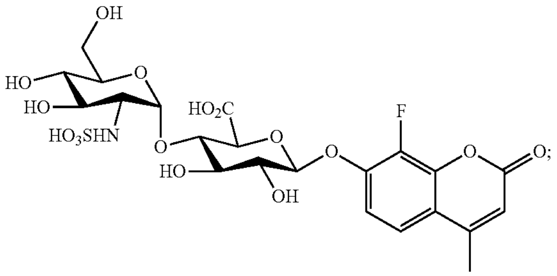

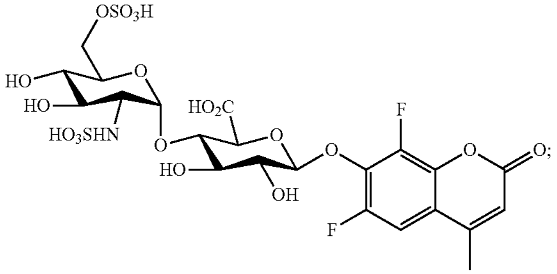

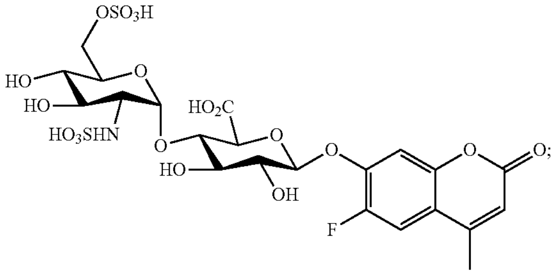

-continued

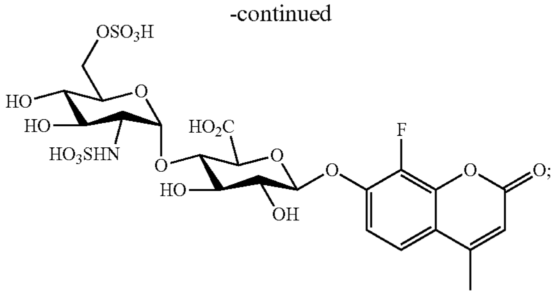

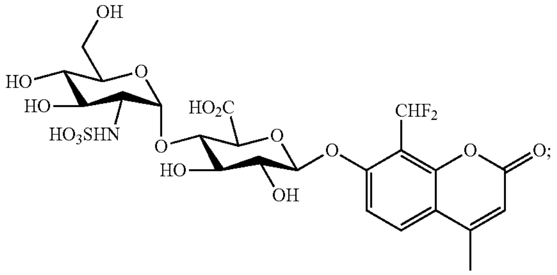

or a salt thereof.

13. A composition comprising a compound of claim 1, or a salt thereof.

14. A method for screening heparanase inhibitors, the method comprising:

a. incubating heparanase with a heparanase inhibitor;

b. adding a compound of claim 1, or a salt thereof; and c. measuring the fluorescence of the mixture from step b.

15. A method of performing positron emission tomography (PET) in a subject, the method comprising administering to the subject a compound of claim 1, or a salt thereof.

16. A method of performing magnetic resonance imaging (MRI) in a subject, the method comprising administering to the subject a compound of claim 1, or a salt thereof.

17. A kit comprising a compound of claim 1, or a salt thereof, and instructions for screening heparanase inhibitors.

18. A kit comprising a compound of claim 1, or a salt thereof, and instructions for administering a compound of claim 1, or a salt thereof, for performing positron emission tomography (PET) in a subject.

19. A kit comprising a compound of claim 1, or a salt thereof, and instructions for administering a compound of claim 1, or a salt thereof, for performing magnetic resonance imaging (MRI) in a subject.

* * * * *